(12) United States Patent
Stiehl et al.

(10) Patent No.: US 10,507,144 B2
(45) Date of Patent: Dec. 17, 2019

(54) ABSORBENT ARTICLES WITH IMPROVED STRENGTH

(71) Applicant: The Procter & Gamble Company, Cincinnati, OH (US)

(72) Inventors: Gabriele Stiehl, Bad Soden (DE); Matthias Morand, Schwalbach am Taunus (DE)

(73) Assignee: The Procter & Gamble Company, Cincinnati, OH (US)

( * ) Notice: Subject to any disclaimer, the term of this patent is extended or adjusted under 35 U.S.C. 154(b) by 690 days.

(21) Appl. No.: 15/070,090

(22) Filed: Mar. 15, 2016

(65) Prior Publication Data

US 2016/0270986 A1 Sep. 22, 2016

Related U.S. Application Data

(60) Provisional application No. 62/158,009, filed on May 7, 2015, provisional application No. 62/133,572, filed on Mar. 16, 2015.

(51) Int. Cl.
*A61F 13/15* (2006.01)
*A61F 13/53* (2006.01)
(Continued)

(52) U.S. Cl.
CPC .............. *A61F 13/53* (2013.01); *A61F 13/45* (2013.01); *A61F 13/534* (2013.01); *A61F 13/539* (2013.01); *A61F 2013/4587* (2013.01); *A61F 2013/5395* (2013.01); *A61F 2013/530131* (2013.01); *A61F 2013/53463* (2013.01); *A61F 2013/530481* (2013.01); *A61F 2013/53908* (2013.01)

(58) Field of Classification Search
CPC ........ A61F 13/53; A61F 13/45; A61F 13/534; A61F 13/539; A61F 2013/4587; A61F 2013/530131; A61F 2013/530481; A61F 2013/53463; A61F 2013/53908; A61F 2013/5395

See application file for complete search history.

(56) References Cited

U.S. PATENT DOCUMENTS 1,733,997 A 10/1929 Marr
1,734,499 A 11/1929 Marinsky
(Continued)

FOREIGN PATENT DOCUMENTS

CA 2001370 4/1990
CA 2291997 6/2000
(Continued)

OTHER PUBLICATIONS

International Search Report, PCT/US2016/022440, dated Jun. 23, 2016, 13 pages.

*Primary Examiner* — Jacqueline F Stephens
(74) *Attorney, Agent, or Firm* — Andrew J. Hagerty; Kathleen Y. Carter

(57) ABSTRACT

An absorbent structure for an absorbent article, comprising a first substrate and an absorbent layer supported thereon, said absorbent layer comprising an absorbent material comprising a superabsorbent polymer material; wherein said absorbent structure comprises a fiberized net structure to at least partially immobilize said absorbent layer onto said first substrate, and whereby said fiberized net structure has a storage modulus (G') at 21° C. of greater than about $1.2 \times 10^6$ Pa.

26 Claims, 10 Drawing Sheets

(51) Int. Cl.
  *A61F 13/534* (2006.01)
  *A61F 13/539* (2006.01)
  *A61F 13/45* (2006.01)

(56) References Cited

U.S. PATENT DOCUMENTS

| | | |
|---|---|---|
| 1,989,283 A | 1/1935 | Limacher |
| 2,058,509 A | 10/1936 | Rose |
| 2,271,676 A | 2/1942 | Bjornbak |
| 2,450,789 A | 10/1948 | Frieman |
| 2,508,811 A | 5/1950 | Best et al. |
| 2,568,910 A | 9/1951 | Condylis |
| 2,570,796 A | 10/1951 | Gross |
| 2,570,963 A | 10/1951 | Mesmer |
| 2,583,553 A | 1/1952 | Faure |
| 2,705,957 A | 4/1955 | Mauro |
| 2,788,003 A | 4/1957 | Morin |
| 2,788,786 A | 4/1957 | Dexter |
| 2,798,489 A | 7/1957 | Behrman |
| 2,807,263 A | 9/1957 | Newton |
| 2,830,589 A | 4/1958 | Doner |
| 2,890,700 A | 6/1959 | Lönberg-Holm |
| 2,890,701 A | 6/1959 | Weinman |
| 2,898,912 A | 8/1959 | Adams |
| 2,931,361 A | 4/1960 | Sostsrin |
| 2,977,957 A | 4/1961 | Clyne |
| 3,071,138 A | 1/1963 | Garcia |
| 3,180,335 A | 4/1965 | Duncan et al. |
| 3,207,158 A | 9/1965 | Yoshitake et al. |
| 3,227,160 A | 1/1966 | Joy |
| 3,386,442 A | 6/1968 | Sabee |
| 3,561,446 A | 2/1971 | Jones |
| 3,572,342 A | 3/1971 | Lindquist et al. |
| 3,572,432 A | 3/1971 | Burton |
| 3,575,174 A | 4/1971 | Mogor |
| 3,578,155 A | 5/1971 | Small et al. |
| 3,606,887 A | 9/1971 | Roeder |
| 3,610,244 A | 10/1971 | Jones |
| 3,618,608 A | 11/1971 | Brink |
| 3,642,001 A | 2/1972 | Sabee |
| 3,653,381 A | 4/1972 | Warnken |
| 3,670,731 A | 6/1972 | Harmon |
| 3,688,767 A | 9/1972 | Goldstein |
| 3,710,797 A | 1/1973 | Marsan |
| 3,731,688 A | 5/1973 | Litt et al. |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand et al. |
| 3,828,784 A | 10/1974 | Sabee |
| 3,840,418 A | 10/1974 | Sabee |
| 3,847,702 A | 11/1974 | Jones |
| 3,848,594 A | 11/1974 | Buell |
| 3,848,595 A | 11/1974 | Endres |
| 3,848,597 A | 11/1974 | Endres |
| 3,860,003 A | 1/1975 | Buell |
| 3,863,637 A | 2/1975 | MacDonald et al. |
| 3,882,870 A | 5/1975 | Hathaway |
| 3,884,234 A | 5/1975 | Taylor |
| 3,900,032 A | 8/1975 | Heurlen |
| 3,911,173 A | 10/1975 | Sprague, Jr. |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,055,180 A | 10/1977 | Karami |
| 4,074,508 A | 2/1978 | Reid |
| 4,079,739 A | 3/1978 | Whitehead |
| 4,084,592 A | 4/1978 | Tritsch |
| 4,100,922 A | 7/1978 | Hernandez |
| 4,232,674 A | 11/1980 | Melican |
| 4,257,418 A | 3/1981 | Hessner |
| 4,259,220 A | 3/1981 | Bunnelle et al. |
| 4,296,750 A | 10/1981 | Woon et al. |
| 4,315,508 A | 2/1982 | Bolick |
| 4,324,246 A | 4/1982 | Mullane et al. |
| 4,340,706 A | 7/1982 | Obayashi et al. |
| 4,341,216 A | 7/1982 | Obenour |
| 4,342,314 A | 8/1982 | Radel et al. |
| 4,360,021 A | 11/1982 | Stima |
| 4,381,783 A | 5/1983 | Elias |
| 4,388,075 A | 6/1983 | Mesek et al. |
| 4,410,571 A | 10/1983 | Korpman |
| 4,461,621 A | 7/1984 | Karami et al. |
| 4,463,045 A | 7/1984 | Ahr et al. |
| 4,469,710 A | 9/1984 | Bielley et al. |
| 4,475,912 A | 10/1984 | Coates |
| 4,490,148 A | 12/1984 | Beckeström |
| 4,507,438 A | 3/1985 | Obayashi et al. |
| 4,515,595 A | 5/1985 | Kievie |
| 4,527,990 A | 7/1985 | Sigl |
| 4,541,871 A | 9/1985 | Obayashi et al. |
| 4,551,191 A | 11/1985 | Kock et al. |
| 4,573,986 A | 3/1986 | Minetola et al. |
| 4,578,072 A | 3/1986 | Lancaster |
| 4,578,702 A | 3/1986 | Campbell |
| 4,585,448 A | 4/1986 | Enloe |
| 4,585,450 A | 4/1986 | Rosch et al. |
| 4,589,878 A | 5/1986 | Mitrani |
| 4,596,568 A | 6/1986 | Flug |
| 4,601,717 A | 7/1986 | Blevins |
| 4,606,964 A | 8/1986 | Wideman |
| 4,609,518 A | 9/1986 | Curro et al. |
| 4,610,678 A | 9/1986 | Weisman et al. |
| 4,623,342 A | 11/1986 | Ito et al. |
| 4,624,666 A | 11/1986 | Derossett |
| 4,629,643 A | 12/1986 | Curro et al. |
| 4,636,207 A | 1/1987 | Buell |
| 4,641,381 A | 2/1987 | Heran et al. |
| 4,646,510 A | 3/1987 | McIntyre |
| 4,662,875 A | 5/1987 | Hirotsu et al. |
| 4,666,983 A | 5/1987 | Tsubakimoto et al. |
| 4,670,011 A | 6/1987 | Mesek |
| 4,670,012 A | 6/1987 | Johnson |
| 4,680,030 A | 7/1987 | Coates et al. |
| 4,681,579 A | 7/1987 | Toussant et al. |
| 4,681,581 A | 7/1987 | Coates |
| 4,681,793 A | 7/1987 | Linman et al. |
| 4,690,680 A | 9/1987 | Higgins |
| 4,695,278 A | 9/1987 | Lawson |
| 4,699,622 A | 10/1987 | Toussant et al. |
| 4,704,115 A | 11/1987 | Buell |
| 4,704,116 A | 11/1987 | Enloe |
| 4,710,189 A | 12/1987 | Lash |
| 4,720,321 A | 1/1988 | Smith |
| 4,731,066 A | 3/1988 | Korpman |
| 4,731,070 A | 3/1988 | Koci |
| RE32,649 E | 4/1988 | Brandt et al. |
| 4,741,941 A | 5/1988 | Englebert et al. |
| 4,747,846 A | 5/1988 | Boland et al. |
| 4,753,648 A | 6/1988 | Jackson |
| 4,773,905 A | 9/1988 | Molee |
| 4,784,892 A | 11/1988 | Storey et al. |
| 4,785,996 A | 11/1988 | Ziecker et al. |
| 4,787,896 A | 11/1988 | Houghton et al. |
| 4,795,454 A | 1/1989 | Dragoo |
| 4,800,102 A | 1/1989 | Takada |
| 4,802,884 A | 2/1989 | Fröidh et al. |
| 4,806,598 A | 2/1989 | Morman |
| 4,808,176 A | 2/1989 | Kielpikowski |
| 4,808,178 A | 2/1989 | Aziz |
| 4,826,880 A | 5/1989 | Lesniak et al. |

(56) References Cited

U.S. PATENT DOCUMENTS

| | | |
|---|---|---|
| 4,834,735 A | 5/1989 | Alemany et al. |
| 4,834,740 A | 5/1989 | Suzuki et al. |
| 4,834,742 A | 5/1989 | Wilson et al. |
| 4,838,886 A | 6/1989 | Kent |
| 4,842,666 A | 6/1989 | Werenicz |
| 4,846,815 A | 7/1989 | Scripps |
| 4,846,825 A | 7/1989 | Enloe et al. |
| 4,848,815 A | 7/1989 | Molloy |
| 4,861,652 A | 8/1989 | Lippert et al. |
| 4,869,724 A | 9/1989 | Scripps |
| 4,886,697 A | 12/1989 | Perdelwitz, Jr. et al. |
| 4,888,231 A | 12/1989 | Angstadt |
| 4,892,528 A | 1/1990 | Suzuki et al. |
| 4,892,535 A | 1/1990 | Bjornberg |
| 4,892,536 A | 1/1990 | DesMarais et al. |
| 4,894,060 A | 1/1990 | Nestegard |
| 4,894,277 A | 1/1990 | Akasaki |
| 4,904,251 A | 2/1990 | Igaue et al. |
| 4,900,317 A | 3/1990 | Buell |
| 4,909,802 A | 3/1990 | Ahr et al. |
| 4,909,803 A | 3/1990 | Aziz et al. |
| 4,936,839 A | 6/1990 | Molee |
| 4,940,463 A | 7/1990 | Leathers et al. |
| 4,940,464 A | 7/1990 | Van Gompel et al. |
| 4,946,527 A | 8/1990 | Battrell |
| 4,950,264 A | 8/1990 | Osborn |
| 4,960,477 A | 10/1990 | Mesek |
| 4,963,140 A | 10/1990 | Robertson et al. |
| 4,966,809 A | 10/1990 | Tanaka et al. |
| 4,968,313 A | 11/1990 | Sabee |
| 4,990,147 A | 2/1991 | Freeland |
| 4,994,053 A | 2/1991 | Lang |
| 5,006,394 A | 4/1991 | Baird |
| 5,019,063 A | 5/1991 | Marsan et al. |
| 5,019,072 A | 5/1991 | Polski |
| 5,021,051 A | 6/1991 | Hiuke |
| 5,030,314 A | 7/1991 | Lang |
| 5,032,120 A | 7/1991 | Freeland et al. |
| 5,034,008 A | 7/1991 | Breitkopf |
| 5,037,416 A | 8/1991 | Allen et al. |
| 5,071,414 A | 8/1991 | Elliott |
| 5,072,687 A | 12/1991 | Mitchell |
| 5,085,654 A | 2/1992 | Buell |
| 5,087,255 A | 2/1992 | Sims et al. |
| 5,092,861 A | 3/1992 | Nomura et al. |
| 5,102,597 A | 4/1992 | Roe et al. |
| 5,114,420 A | 5/1992 | Igaue et al. |
| 5,124,188 A | 6/1992 | Roe et al. |
| 5,135,522 A | 8/1992 | Fahrenkrug et al. |
| 5,137,537 A | 8/1992 | Herron et al. |
| D329,697 S | 9/1992 | Fahrenkrug et al. |
| 5,143,679 A | 9/1992 | Weber et al. |
| 5,147,343 A | 9/1992 | Kellenberger |
| 5,147,345 A | 9/1992 | Young et al. |
| 5,149,334 A | 9/1992 | Roe et al. |
| 5,149,335 A | 9/1992 | Kellenberger et al. |
| 5,151,091 A | 9/1992 | Glaug |
| 5,151,092 A | 9/1992 | Buell et al. |
| 5,156,793 A | 10/1992 | Buell et al. |
| 5,167,653 A | 12/1992 | Igaue et al. |
| 5,167,897 A | 12/1992 | Weber et al. |
| 5,175,046 A | 12/1992 | Nguyen |
| 5,180,622 A | 1/1993 | Berg et al. |
| 5,190,563 A | 3/1993 | Herron et al. |
| 5,190,606 A | 3/1993 | Merkatoris et al. |
| 5,204,997 A | 4/1993 | Suzuki et al. |
| 5,213,817 A | 5/1993 | Pelley |
| 5,221,274 A | 6/1993 | Buell et al. |
| 5,235,515 A | 8/1993 | Ungpiyakul et al. |
| 5,242,436 A | 9/1993 | Weil et al. |
| 5,246,431 A | 9/1993 | Minetola et al. |
| 5,246,432 A | 9/1993 | Suzuki et al. |
| 5,246,433 A | 9/1993 | Hasse et al. |
| 5,248,309 A | 9/1993 | Serbiak et al. |
| 5,260,345 A | 11/1993 | DesMarais et al. |
| 5,269,775 A | 12/1993 | Freeland et al. |
| 5,281,683 A | 1/1994 | Yano et al. |
| H1298 H | 4/1994 | Ahr |
| 5,300,565 A | 4/1994 | Berg et al. |
| 5,312,386 A | 5/1994 | Correa et al. |
| 5,331,059 A | 7/1994 | Engelhardt et al. |
| 5,336,552 A | 8/1994 | Strack et al. |
| 5,348,547 A | 9/1994 | Payne et al. |
| 5,358,500 A | 10/1994 | LaVon et al. |
| 5,366,782 A | 11/1994 | Curro et al. |
| 5,382,610 A | 1/1995 | Harada et al. |
| 5,387,207 A | 2/1995 | Dyer et al. |
| 5,387,208 A | 2/1995 | Ashton et al. |
| 5,387,209 A | 2/1995 | Yamamoto et al. |
| 5,389,095 A | 2/1995 | Suzuki |
| 5,397,316 A | 3/1995 | LaVon et al. |
| 5,397,317 A | 3/1995 | Thomas |
| 5,399,175 A | 3/1995 | Glaug |
| 5,401,792 A | 3/1995 | Babu et al. |
| 5,409,771 A | 4/1995 | Dahmen et al. |
| H1440 H | 5/1995 | New et al. |
| 5,411,497 A | 5/1995 | Tanzer et al. |
| 5,415,644 A | 5/1995 | Enloe |
| 5,425,725 A | 6/1995 | Tanzer et al. |
| 5,429,630 A | 7/1995 | Beal et al. |
| 5,433,715 A | 7/1995 | Tanzer et al. |
| 5,451,219 A | 9/1995 | Suzuki |
| 5,451,442 A | 9/1995 | Pieniak |
| 5,460,622 A | 10/1995 | Dragoo et al. |
| 5,462,541 A | 10/1995 | Bruemmer et al. |
| 5,476,458 A | 12/1995 | Glaug et al. |
| 5,486,166 A | 1/1996 | Bishop et al. |
| 5,486,167 A | 1/1996 | Dragoo et al. |
| 5,490,846 A | 2/1996 | Ellis et al. |
| 5,492,962 A | 2/1996 | Lahrman et al. |
| 5,494,622 A | 2/1996 | Heath et al. |
| 5,499,978 A | 3/1996 | Buell et al. |
| 5,507,736 A | 4/1996 | Clear et al. |
| 5,507,895 A | 4/1996 | Suekane |
| 5,509,915 A | 4/1996 | Hanson et al. |
| 5,514,104 A | 5/1996 | Cole |
| 5,518,801 A | 5/1996 | Chappell et al. |
| 5,520,674 A | 5/1996 | Hines et al. |
| 5,522,810 A | 6/1996 | Allen, Jr. |
| 5,527,300 A | 6/1996 | Sauer |
| 5,531,730 A | 7/1996 | Dreier |
| 5,532,323 A | 7/1996 | Yano et al. |
| 5,542,943 A | 8/1996 | Sageser |
| 5,549,592 A | 8/1996 | Fries et al. |
| 5,549,593 A | 8/1996 | Ygge et al. |
| 5,549,791 A | 8/1996 | Herron et al. |
| 5,554,145 A | 9/1996 | Roe et al. |
| 5,559,335 A | 9/1996 | Zing et al. |
| 5,560,878 A | 10/1996 | Dragoo et al. |
| 5,562,634 A | 10/1996 | Flumene et al. |
| 5,562,646 A | 10/1996 | Goldman et al. |
| 5,569,234 A | 10/1996 | Buell et al. |
| 5,571,096 A | 11/1996 | Dobrin et al. |
| 5,574,121 A | 11/1996 | Irie et al. |
| 5,580,411 A | 12/1996 | Nease et al. |
| 5,584,829 A | 12/1996 | Lavash et al. |
| 5,586,979 A | 12/1996 | Thomas |
| 5,591,152 A | 1/1997 | Buell et al. |
| 5,591,155 A | 1/1997 | Nishikawa et al. |
| 5,593,399 A | 1/1997 | Tanzer et al. |
| 5,599,335 A | 2/1997 | Goldman et al. |
| 5,601,542 A | 2/1997 | Melius et al. |
| 5,607,414 A | 3/1997 | Richards et al. |
| 5,607,537 A | 3/1997 | Johnson et al. |
| 5,607,760 A | 3/1997 | Roe |
| 5,609,587 A | 3/1997 | Roe |
| 5,609,588 A | 3/1997 | DiPalma et al. |
| 5,611,879 A | 3/1997 | Morman |
| 5,613,959 A | 3/1997 | Roessler et al. |
| 5,613,960 A | 3/1997 | Mizutani |
| 5,614,283 A | 3/1997 | Potnis et al. |
| 5,622,589 A | 4/1997 | Johnson et al. |
| 5,624,423 A | 4/1997 | Anjur |
| 5,624,424 A | 4/1997 | Saisaka et al. |

(56) References Cited

U.S. PATENT DOCUMENTS

| | | |
|---|---|---|
| 5,625,222 A | 4/1997 | Yoneda et al. |
| 5,607,416 A | 5/1997 | Yamamoto et al. |
| 5,626,571 A | 5/1997 | Young et al. |
| 5,628,741 A | 5/1997 | Buell et al. |
| 5,628,845 A | 5/1997 | Murray et al. |
| 5,635,191 A | 6/1997 | Roe et al. |
| 5,635,271 A | 6/1997 | Zafiroglu |
| 5,637,106 A | 6/1997 | Mitchell |
| 5,643,238 A | 7/1997 | Baker |
| 5,643,243 A | 7/1997 | Klemp |
| 5,643,588 A | 7/1997 | Roe et al. |
| 5,649,914 A | 7/1997 | Glaug |
| 5,650,214 A | 7/1997 | Anderson |
| H1674 H | 8/1997 | Ames et al. |
| 5,658,268 A | 8/1997 | Johns et al. |
| 5,662,634 A | 9/1997 | Yamamoto et al. |
| 5,662,638 A | 9/1997 | Johnson et al. |
| 5,662,758 A | 9/1997 | Hamilton et al. |
| 5,669,894 A | 9/1997 | Goldman et al. |
| 5,674,215 A | 10/1997 | Ronnberg |
| 5,681,300 A | 10/1997 | Ahr |
| 5,683,374 A | 11/1997 | Yamamoto |
| 5,685,874 A | 11/1997 | Buell et al. |
| 5,690,627 A | 11/1997 | Clear et al. |
| 5,691,035 A | 11/1997 | Chappell et al. |
| 5,691,036 A | 11/1997 | Chappell et al. |
| 5,695,488 A | 12/1997 | Sosalla |
| 5,700,254 A | 12/1997 | McDowall et al. |
| 5,702,376 A | 12/1997 | Glaug |
| 5,714,156 A | 2/1998 | Schmidt et al. |
| 5,723,087 A | 3/1998 | Chappell et al. |
| 5,733,275 A | 3/1998 | Davis et al. |
| 5,749,866 A | 5/1998 | Roe et al. |
| 5,752,947 A | 5/1998 | Awolin |
| 5,756,039 A | 5/1998 | Mcfall et al. |
| H1732 H | 6/1998 | Johnson |
| 5,762,641 A | 6/1998 | Bewick-Sonntag et al. |
| 5,766,388 A | 6/1998 | Pelley |
| 5,766,389 A | 6/1998 | Brandon et al. |
| 5,772,825 A | 6/1998 | Schmitz |
| 5,776,121 A | 7/1998 | Roe et al. |
| 5,779,831 A | 7/1998 | Schmitz |
| 5,788,684 A | 8/1998 | Abuto et al. |
| 5,795,345 A | 8/1998 | Mizutani |
| 5,797,892 A | 8/1998 | Glaug |
| 5,797,894 A | 8/1998 | Cadieux et al. |
| 5,807,365 A | 9/1998 | Luceri |
| 5,810,796 A | 9/1998 | Kimura et al. |
| 5,810,800 A | 9/1998 | Hunter et al. |
| 5,814,035 A | 9/1998 | Gryskiewicz et al. |
| 5,820,618 A | 10/1998 | Roberts et al. |
| 5,827,257 A | 10/1998 | Fujioka |
| 5,830,202 A | 11/1998 | Bogdanski et al. |
| 5,833,678 A | 11/1998 | Ashton et al. |
| 5,837,789 A | 11/1998 | Stockhausen et al. |
| 5,840,404 A | 11/1998 | Graff |
| 5,843,059 A | 12/1998 | Niemeyer et al. |
| 5,846,231 A | 12/1998 | Fujioka et al. |
| 5,846,232 A | 12/1998 | Serbiak et al. |
| 5,849,816 A | 12/1998 | Suskind et al. |
| 5,851,204 A | 12/1998 | Mitzutani |
| 5,855,572 A | 1/1999 | Schmidt |
| 5,858,013 A | 1/1999 | Kling |
| 5,865,823 A | 2/1999 | Curro |
| 5,865,824 A | 2/1999 | Chen |
| 5,873,868 A | 2/1999 | Nakahata |
| 5,876,391 A | 3/1999 | Roe et al. |
| 5,879,751 A | 3/1999 | Bogdanski |
| 5,891,118 A | 4/1999 | Toyoshima |
| 5,891,544 A | 4/1999 | Chappell et al. |
| 5,897,545 A | 4/1999 | Kline et al. |
| 5,904,673 A | 5/1999 | Roe et al. |
| 5,925,439 A | 7/1999 | Haubach |
| 5,928,184 A | 7/1999 | Etheredge |
| 5,931,825 A | 8/1999 | Kuen et al. |
| 5,938,648 A | 8/1999 | Lavon et al. |
| 5,938,650 A | 8/1999 | Baer et al. |
| 5,941,862 A | 8/1999 | Haynes et al. |
| 5,944,706 A | 8/1999 | Palumbo et al. |
| 5,947,949 A | 9/1999 | Inoue et al. |
| 5,951,536 A | 9/1999 | Osborn, III et al. |
| 5,957,908 A | 9/1999 | Kline et al. |
| 5,968,025 A | 10/1999 | Roe et al. |
| 5,968,029 A | 10/1999 | Chappell et al. |
| 5,980,500 A | 11/1999 | Shimizu et al. |
| 5,981,824 A | 11/1999 | Luceri |
| 5,989,236 A | 11/1999 | Roe et al. |
| 6,004,306 A | 12/1999 | Robles et al. |
| 6,022,430 A | 2/2000 | Blenke et al. |
| 6,022,431 A | 2/2000 | Blenke et al. |
| 6,042,673 A | 3/2000 | Johnson et al. |
| 6,050,984 A | 4/2000 | Fujioka |
| 6,054,631 A | 4/2000 | Gent |
| 6,056,732 A | 5/2000 | Fujioka et al. |
| 6,060,115 A | 5/2000 | Borowski et al. |
| 6,068,620 A | 5/2000 | Chmielewski |
| 6,080,909 A | 6/2000 | Osterdahl et al. |
| 6,083,210 A | 7/2000 | Young et al. |
| 6,090,994 A | 7/2000 | Chen |
| 6,091,336 A | 7/2000 | Zand |
| 6,093,474 A | 7/2000 | Sironi |
| 6,099,515 A | 8/2000 | Sugito |
| 6,102,892 A | 8/2000 | Putzer et al. |
| 6,103,814 A | 8/2000 | Van Drongelen et al. |
| 6,107,537 A | 8/2000 | Elder et al. |
| 6,110,157 A | 8/2000 | Schmidt |
| 6,117,121 A | 9/2000 | Faulks et al. |
| 6,117,803 A | 9/2000 | Morman et al. |
| 6,120,486 A | 9/2000 | Toyoda et al. |
| 6,120,487 A | 9/2000 | Ashton |
| 6,120,489 A | 9/2000 | Johnson et al. |
| 6,120,866 A | 9/2000 | Arakawa et al. |
| 6,121,509 A | 9/2000 | Ashraf et al. |
| 6,129,717 A | 10/2000 | Fujioka et al. |
| 6,129,720 A | 10/2000 | Blenke et al. |
| 6,132,411 A | 10/2000 | Huber et al. |
| 6,139,912 A | 10/2000 | Onuschak |
| 6,143,821 A | 11/2000 | Houben |
| 6,152,908 A | 11/2000 | Widlund |
| 6,156,023 A | 12/2000 | Yoshioka |
| 6,156,424 A | 12/2000 | Taylor |
| 6,160,197 A | 12/2000 | Lassen |
| 6,165,160 A | 12/2000 | Suzuki et al. |
| 6,174,302 B1 | 1/2001 | Kumasaka |
| 6,177,606 B1 | 1/2001 | Etheredge |
| 6,177,607 B1 | 1/2001 | Blaney et al. |
| 6,186,996 B1 | 2/2001 | Martin |
| 6,210,386 B1 | 4/2001 | Inoue |
| 6,210,390 B1 | 4/2001 | Karlsson |
| 6,231,556 B1 | 5/2001 | Osborn, III |
| 6,231,566 B1 | 5/2001 | Lai |
| 6,238,380 B1 | 5/2001 | Sasaki |
| 6,241,716 B1 | 6/2001 | Rönnberg |
| 6,254,294 B1 | 7/2001 | Muhar |
| 6,258,996 B1 | 7/2001 | Goldman |
| 6,265,488 B1 | 7/2001 | Fujino et al. |
| 6,290,686 B1 | 9/2001 | Tanzer et al. |
| 6,306,122 B1 | 10/2001 | Narawa et al. |
| 6,315,765 B1 | 11/2001 | Datta |
| 6,319,239 B1 | 11/2001 | Daniels et al. |
| 6,322,552 B1 | 11/2001 | Blenke et al. |
| 6,325,787 B1 | 12/2001 | Roe et al. |
| 6,326,525 B1 | 12/2001 | Hamajima |
| 6,330,735 B1 | 12/2001 | Hahn et al. |
| 6,334,858 B1 | 1/2002 | Rönnberg et al. |
| 6,336,922 B1 | 1/2002 | Van Gompel et al. |
| 6,340,611 B1 | 1/2002 | Shimizu |
| 6,342,715 B1 | 1/2002 | Shimizu |
| 6,402,731 B1 | 1/2002 | Suprise et al. |
| 6,350,332 B1 | 2/2002 | Thomas et al. |
| 6,368,687 B1 | 4/2002 | Joseph et al. |
| 6,371,948 B1 | 4/2002 | Mizutani |
| 6,372,952 B1 | 4/2002 | Lash et al. |
| 6,375,644 B2 | 4/2002 | Mizutani |

(56) References Cited

U.S. PATENT DOCUMENTS

| | | |
|---|---|---|
| 6,376,034 B1 | 4/2002 | Brander |
| 6,383,431 B1 | 5/2002 | Dobrin et al. |
| 6,383,960 B1 | 5/2002 | Everett et al. |
| 6,394,989 B2 | 5/2002 | Mizutani |
| 6,403,857 B1 | 6/2002 | Gross et al. |
| 6,409,883 B1 | 6/2002 | Makolin |
| 6,410,820 B1 | 6/2002 | McFall et al. |
| 6,410,822 B1 | 6/2002 | Mizutani |
| 6,402,729 B1 | 7/2002 | Boberg et al. |
| 6,413,248 B1 | 7/2002 | Mizutani |
| 6,413,249 B1 | 7/2002 | Turi et al. |
| 6,414,214 B1 | 7/2002 | Engelhardt et al. |
| 6,416,502 B1 | 7/2002 | Connelly et al. |
| 6,416,697 B1 | 7/2002 | Venturino et al. |
| 6,419,667 B1 | 7/2002 | Avalon et al. |
| 6,423,046 B1 | 7/2002 | Fujioka et al. |
| 6,423,048 B1 | 7/2002 | Suzuki et al. |
| 6,423,884 B1 | 7/2002 | Oehmen |
| 6,429,350 B1 | 8/2002 | Tanzer et al. |
| 6,432,094 B1 | 8/2002 | Fujioka et al. |
| 6,432,098 B1 | 8/2002 | Kline et al. |
| 6,432,099 B2 | 8/2002 | Rönnberg |
| 6,437,214 B1 | 8/2002 | Everett et al. |
| 6,441,268 B1 | 8/2002 | Edwardsson |
| 6,443,933 B1 | 9/2002 | Suzuki et al. |
| 6,444,064 B1 | 9/2002 | Henry et al. |
| 6,447,496 B1 | 9/2002 | Mizutani |
| 6,458,111 B1 | 10/2002 | Onishi et al. |
| 6,458,877 B1 | 10/2002 | Ahmed et al. |
| 6,459,016 B1 | 10/2002 | Rosenfeld et al. |
| 6,461,034 B1 | 10/2002 | Schaefer et al. |
| 6,461,342 B2 | 10/2002 | Tanji et al. |
| 6,461,343 B1 | 10/2002 | Schaefer et al. |
| 6,472,478 B1 | 10/2002 | Funk et al. |
| 6,475,201 B2 | 11/2002 | Saito et al. |
| 6,494,872 B1 | 12/2002 | Suzuki et al. |
| 6,494,873 B2 | 12/2002 | Karlsson et al. |
| 6,500,159 B1 | 12/2002 | Carvalho |
| 6,503,233 B1 | 1/2003 | Chen |
| 6,503,979 B1 | 1/2003 | Funk et al. |
| 6,506,186 B1 | 1/2003 | Roessler |
| 6,506,961 B1 | 1/2003 | Levy |
| 6,515,195 B1 | 2/2003 | Lariviere |
| 6,517,525 B1 | 2/2003 | Berthou |
| 6,518,479 B1 | 2/2003 | Graef |
| 6,520,947 B1 | 2/2003 | Tilly et al. |
| 6,521,811 B1 | 2/2003 | Lassen |
| 6,521,812 B1 | 2/2003 | Graef |
| 6,524,294 B1 | 2/2003 | Hilston et al. |
| 6,525,240 B1 | 2/2003 | Graef |
| 6,528,698 B2 | 3/2003 | Mizutani et al. |
| 6,529,860 B1 | 3/2003 | Strumolo et al. |
| 6,531,025 B1 | 3/2003 | Lender et al. |
| 6,531,027 B1 | 3/2003 | Lender et al. |
| 6,534,149 B1 | 3/2003 | Daley et al. |
| 6,559,081 B1 | 5/2003 | Erspamer |
| 6,559,239 B1 | 5/2003 | Riegel et al. |
| 6,562,168 B1 | 5/2003 | Schmitt et al. |
| 6,562,192 B1 | 5/2003 | Hamilton |
| 6,569,137 B2 | 5/2003 | Suzuki et al. |
| 6,573,422 B1 | 6/2003 | Rosenfeld |
| 6,585,713 B1 | 7/2003 | LaMahieu et al. |
| 6,585,858 B1 | 7/2003 | Otto et al. |
| 6,602,234 B1 | 8/2003 | Klemp et al. |
| 6,605,070 B2 | 8/2003 | Ludwig et al. |
| 6,605,172 B1 | 8/2003 | Anderson et al. |
| 6,605,752 B2 | 8/2003 | Magnusson et al. |
| 6,610,900 B1 | 8/2003 | Tanzer |
| 6,630,054 B1 | 10/2003 | Graef |
| 6,632,209 B1 | 10/2003 | Chmielewski |
| 6,632,504 B1 | 10/2003 | Gillespie et al. |
| 6,645,569 B2 | 11/2003 | Cramer et al. |
| 6,646,180 B1 | 11/2003 | Chmielewski |
| 6,648,869 B1 | 11/2003 | Gillies et al. |
| 6,648,870 B2 | 11/2003 | Itoh et al. |
| 6,648,871 B2 | 11/2003 | Kusibojoska et al. |
| 6,649,807 B2 | 11/2003 | Mizutani |
| 6,649,810 B1 | 11/2003 | Minato et al. |
| 6,657,015 B1 | 12/2003 | Riegel et al. |
| 6,657,102 B2 | 12/2003 | Furuya |
| 6,667,424 B1 | 12/2003 | Hamilton |
| 6,670,522 B1 | 12/2003 | Graef |
| 6,673,982 B1 | 1/2004 | Chen |
| 6,673,983 B1 | 1/2004 | Graef |
| 6,673,985 B2 | 1/2004 | Mizutani |
| 6,682,515 B1 | 1/2004 | Mizutani et al. |
| 6,682,516 B2 | 1/2004 | Johnston |
| 6,689,115 B1 | 2/2004 | Popp et al. |
| 6,689,934 B2 | 2/2004 | Dodge, II et al. |
| 6,695,827 B2 | 2/2004 | Chen |
| 6,700,034 B1 | 3/2004 | Lindsay et al. |
| 6,703,538 B2 | 3/2004 | Lassen |
| 6,705,465 B2 | 3/2004 | Ling et al. |
| 6,706,129 B2 | 3/2004 | Ando et al. |
| 6,706,943 B2 | 3/2004 | Onishi |
| 6,710,224 B2 | 3/2004 | Chmielewski et al. |
| 6,710,225 B1 | 3/2004 | Everett et al. |
| 6,716,205 B2 | 4/2004 | Popp et al. |
| 6,716,441 B1 | 4/2004 | Roe et al. |
| 6,717,029 B2 | 4/2004 | Baker |
| 6,726,668 B2 | 4/2004 | Underhill et al. |
| 6,726,792 B1 | 4/2004 | Johnson et al. |
| 6,730,387 B2 | 5/2004 | Rezai et al. |
| 6,734,335 B1 | 5/2004 | Graef |
| 6,790,798 B1 | 9/2004 | Suzuki et al. |
| 6,802,834 B2 | 10/2004 | Melius et al. |
| 6,809,158 B2 | 10/2004 | Ikeuchi et al. |
| 6,811,642 B2 | 11/2004 | Ochi |
| 6,818,083 B2 | 11/2004 | Mcamish et al. |
| 6,818,166 B2 | 11/2004 | Edwardson et al. |
| 6,830,800 B2 | 12/2004 | Curro et al. |
| 6,832,905 B2 | 12/2004 | Delzer et al. |
| 6,840,929 B2 | 1/2005 | Kurata |
| 6,846,374 B2 | 1/2005 | Popp |
| 6,858,771 B2 | 2/2005 | Yoshimasa |
| 6,863,933 B2 | 3/2005 | Cramer et al. |
| 6,863,960 B2 | 3/2005 | Curro et al. |
| 6,867,345 B2 | 3/2005 | Shimoe et al. |
| 6,867,346 B1 | 3/2005 | Dopps |
| 6,878,433 B2 | 4/2005 | Curro et al. |
| 6,878,647 B1 | 4/2005 | Rezai |
| 6,880,211 B2 | 4/2005 | Jackson et al. |
| 6,891,080 B2 | 5/2005 | Minato |
| 6,904,865 B2 | 6/2005 | Klofta |
| 6,911,574 B1 | 6/2005 | Mizutani |
| 6,923,797 B2 | 8/2005 | Shinohara et al. |
| 6,923,926 B2 | 8/2005 | Walter et al. |
| 6,926,703 B2 | 8/2005 | Sugito |
| 6,929,629 B2 | 8/2005 | Drevik et al. |
| 6,939,914 B2 | 9/2005 | Qin et al. |
| 6,946,585 B2 | 9/2005 | Brown |
| 6,953,451 B2 | 10/2005 | Berba |
| 6,955,733 B2 | 10/2005 | Henry et al. |
| 6,962,578 B1 | 11/2005 | Lavon |
| 6,962,645 B2 | 11/2005 | Graef |
| 6,965,058 B1 | 11/2005 | Raidel |
| 6,969,781 B2 | 11/2005 | Graef |
| 6,972,010 B2 | 12/2005 | Pesce et al. |
| 6,972,011 B2 | 12/2005 | Maeda et al. |
| 6,979,564 B2 | 12/2005 | Glucksmann et al. |
| 6,982,052 B2 | 1/2006 | Daniels et al. |
| 7,001,167 B2 | 2/2006 | Venturino |
| 7,014,632 B2 | 3/2006 | Takino et al. |
| 7,015,370 B2 | 3/2006 | Watanabe |
| 7,037,299 B2 | 5/2006 | Turi et al. |
| 7,037,571 B2 | 5/2006 | Fish et al. |
| 7,048,726 B2 | 5/2006 | Kusagawa et al. |
| 7,056,311 B2 | 6/2006 | Kinoshita |
| 7,067,711 B2 | 6/2006 | Kinoshita et al. |
| 7,073,373 B2 | 7/2006 | La Fortune |
| 7,078,583 B2 | 7/2006 | Kudo |
| 7,090,665 B2 | 8/2006 | Ohashi |
| 7,108,759 B2 | 9/2006 | You |
| 7,108,916 B2 | 9/2006 | Ehrnsperger et al. |

(56) References Cited

U.S. PATENT DOCUMENTS

| | | | |
|---|---|---|---|
| 7,112,621 | B2 | 9/2006 | Rohrbaugh et al. |
| 7,122,713 | B2 | 10/2006 | Komatsu |
| 7,125,470 | B2 | 10/2006 | Graef |
| 7,132,585 | B2 | 11/2006 | Kudo |
| 7,147,628 | B2 | 12/2006 | Drevik |
| 7,150,729 | B2 | 12/2006 | Shimada |
| 7,154,019 | B2 | 12/2006 | Mishima et al. |
| 7,160,281 | B2 | 1/2007 | Leminh et al. |
| 7,163,528 | B2 | 1/2007 | Christon et al. |
| 7,166,190 | B2 | 1/2007 | Graef |
| 7,169,136 | B2 | 1/2007 | Otsubo |
| 7,183,360 | B2 | 2/2007 | Daniel et al. |
| 7,189,888 | B2 | 3/2007 | Wang et al. |
| 7,196,241 | B2 | 3/2007 | Kinoshita |
| 7,199,211 | B2 | 4/2007 | Popp et al. |
| 7,204,830 | B2 | 4/2007 | Mishima |
| 7,207,978 | B2 | 4/2007 | Takino |
| 7,219,403 | B2 | 5/2007 | Miyamoto et al. |
| 7,220,251 | B2 | 5/2007 | Otsubo et al. |
| 7,241,280 | B2 | 7/2007 | Christen et al. |
| 7,250,481 | B2 | 7/2007 | Jaworek et al. |
| 7,252,657 | B2 | 8/2007 | Mishima |
| 7,265,258 | B2 | 9/2007 | Hamilton |
| 7,270,651 | B2 | 9/2007 | Adams et al. |
| 7,285,178 | B2 | 10/2007 | Mischler et al. |
| 7,306,582 | B2 | 12/2007 | Adams et al. |
| 7,311,696 | B2 | 12/2007 | Christen et al. |
| 7,311,968 | B2 | 12/2007 | Ehrnsperger et al. |
| 7,312,372 | B2 | 12/2007 | Miyama |
| 7,318,820 | B2 | 1/2008 | LaVon et al. |
| 7,329,244 | B2 | 2/2008 | Otsubo |
| 7,329,246 | B2 | 2/2008 | Kinoshita |
| 7,335,810 | B2 | 2/2008 | Yoshimasa et al. |
| 7,377,914 | B2 | 5/2008 | LaVon |
| 7,429,689 | B2 | 9/2008 | Chen |
| 7,435,244 | B2 | 10/2008 | Schroer et al. |
| 7,465,373 | B2 | 12/2008 | Graef |
| 7,500,969 | B2 | 3/2009 | Mishima |
| 7,504,552 | B2 | 3/2009 | Tamura |
| 7,521,109 | B2 | 4/2009 | Suzuki et al. |
| 7,521,587 | B2 | 4/2009 | Busam et al. |
| 7,537,832 | B2 | 5/2009 | Carlucci et al. |
| 7,547,815 | B2 | 6/2009 | Ohashi |
| 7,550,646 | B2 | 6/2009 | Tamura |
| 7,563,257 | B2 | 7/2009 | Nakajima |
| 7,588,561 | B2 | 9/2009 | Kenmochi |
| 7,594,904 | B2 | 9/2009 | Rosenfeld |
| 7,598,428 | B2 | 10/2009 | Gustavsson et al. |
| 7,625,363 | B2 | 12/2009 | Yoshimasa |
| 7,641,642 | B2 | 1/2010 | Murai et al. |
| 7,648,490 | B2 | 1/2010 | Kuroda |
| 7,652,111 | B2 | 1/2010 | Hermeling et al. |
| 7,666,173 | B2 | 2/2010 | Mishima |
| 7,666,174 | B2 | 2/2010 | Kawakami et al. |
| 7,686,790 | B2 | 3/2010 | Rasmussen et al. |
| 7,687,596 | B2 | 3/2010 | Hermeling et al. |
| 7,695,461 | B2 | 4/2010 | Rosenfeld |
| 7,696,402 | B2 | 4/2010 | Nishikawa |
| 7,708,725 | B2 | 5/2010 | Tamagawa |
| 7,717,150 | B2 | 5/2010 | Manabe |
| 7,718,844 | B2 | 5/2010 | Olson |
| 7,722,587 | B2 | 5/2010 | Suzuki et al. |
| 7,722,590 | B2 | 5/2010 | Tsuji |
| 7,727,217 | B2 | 6/2010 | Hancock-Cooke |
| 7,736,351 | B2 | 6/2010 | Nigam |
| 7,737,324 | B2 | 6/2010 | LaVon et al. |
| 7,744,576 | B2 | 6/2010 | Busam et al. |
| 7,744,578 | B2 | 6/2010 | Tanio et al. |
| 7,750,203 | B2 | 7/2010 | Busam et al. |
| 7,754,822 | B2 | 7/2010 | Daniel et al. |
| 7,754,940 | B2 | 7/2010 | Brisebois |
| 7,759,540 | B2 | 7/2010 | Litvay et al. |
| 7,763,004 | B2 | 7/2010 | Beck |
| 7,767,875 | B2 | 8/2010 | Olson |
| 7,767,876 | B2 | 8/2010 | Davis et al. |
| 7,767,878 | B2 | 8/2010 | Suzuki |
| 7,772,420 | B2 | 8/2010 | Hermeling et al. |
| 7,786,341 | B2 | 8/2010 | Schneider et al. |
| 7,795,492 | B2 | 9/2010 | Vartiainen |
| 7,803,145 | B2 | 9/2010 | Rosenfeld |
| 7,825,291 | B2 | 11/2010 | Elfsberg et al. |
| 7,838,722 | B2 | 11/2010 | Blessing et al. |
| 7,850,672 | B2 | 12/2010 | Guidotti et al. |
| 7,851,667 | B2 | 12/2010 | Becker et al. |
| 7,855,314 | B2 | 12/2010 | Hanao |
| 7,857,797 | B2 | 12/2010 | Kudo |
| 7,858,842 | B2 | 12/2010 | Komatsu |
| 7,884,259 | B2 | 2/2011 | Hanao |
| 7,888,549 | B2 | 2/2011 | Jansson et al. |
| 7,910,797 | B2 | 3/2011 | Nandrea |
| 7,931,636 | B2 | 4/2011 | LaVon et al. |
| 7,935,207 | B2 | 5/2011 | Zhao |
| 7,935,861 | B2 | 5/2011 | Suzuki |
| 7,938,813 | B2 | 5/2011 | Wang et al. |
| 7,942,858 | B2 | 5/2011 | Francoeur |
| 7,951,126 | B2 | 5/2011 | Nanjyo |
| 7,959,620 | B2 | 6/2011 | Miura et al. |
| 7,982,091 | B2 | 7/2011 | Konawa |
| 7,993,319 | B2 | 8/2011 | Sperl |
| 8,017,827 | B2 | 9/2011 | Hundorf et al. |
| 8,029,486 | B2 | 10/2011 | Nakajima |
| 8,034,991 | B2 | 10/2011 | Bruzadin et al. |
| 8,039,684 | B2 | 10/2011 | Guidotti et al. |
| 8,052,454 | B2 | 11/2011 | Polnyi |
| 8,057,620 | B2 | 11/2011 | Perego et al. |
| 8,109,915 | B2 | 2/2012 | Shimoe |
| 8,133,212 | B2 | 3/2012 | Takada |
| 8,148,598 | B2 | 4/2012 | Tsang et al. |
| 8,163,124 | B2 | 4/2012 | Moriura et al. |
| 8,167,862 | B2 | 5/2012 | Digiacomantonio et al. |
| 8,173,858 | B2 | 5/2012 | Kuroda |
| 8,178,747 | B2 | 5/2012 | Venturino et al. |
| 8,183,430 | B2 | 5/2012 | Hakansson et al. |
| 8,186,296 | B2 | 5/2012 | Brown et al. |
| 8,187,239 | B2 | 5/2012 | LaVon et al. |
| 8,187,240 | B2 | 5/2012 | Busam et al. |
| 8,198,506 | B2 | 6/2012 | Venturino et al. |
| 8,211,815 | B2 | 7/2012 | Baker |
| 8,236,715 | B2 | 8/2012 | Schmidt et al. |
| 8,237,012 | B2 | 8/2012 | Miyama |
| 8,246,594 | B2 | 8/2012 | Sperl |
| 8,258,367 | B2 | 9/2012 | Lawson et al. |
| 8,268,424 | B1 | 9/2012 | Suzuki |
| 8,273,943 | B2 | 9/2012 | Noda |
| 8,282,617 | B2 | 10/2012 | Kaneda |
| 8,283,516 | B2 | 10/2012 | Litvay |
| 8,317,766 | B2 | 11/2012 | Naoto |
| 8,317,768 | B2 | 11/2012 | Larsson |
| 8,319,005 | B2 | 11/2012 | Becker et al. |
| 8,343,123 | B2 | 1/2013 | Noda |
| 8,343,296 | B2 | 1/2013 | Blessing et al. |
| 8,360,977 | B2 | 1/2013 | Marttila et al. |
| 8,361,047 | B2 | 1/2013 | Mukai et al. |
| 8,377,025 | B2 | 2/2013 | Nakajima et al. |
| 8,450,555 | B2 | 5/2013 | Nahn et al. |
| 8,496,637 | B2 | 7/2013 | Hundorf et al. |
| 8,519,213 | B2 | 8/2013 | Venturino et al. |
| 8,524,355 | B2 | 9/2013 | Nakaoka |
| 8,552,252 | B2 | 10/2013 | Hundorf et al. |
| 8,568,566 | B2 | 10/2013 | Jackets et al. |
| 8,581,019 | B2 | 11/2013 | Carlucci et al. |
| 8,603,058 | B2 | 12/2013 | Sprerl et al. |
| 8,604,270 | B2 | 12/2013 | Venturino et al. |
| 8,633,347 | B2 | 1/2014 | Bianco et al. |
| 8,664,468 | B2 | 3/2014 | Lawson et al. |
| 8,674,170 | B2 | 3/2014 | Busam et al. |
| 8,734,417 | B2 | 5/2014 | LaVon et al. |
| 8,766,031 | B2 | 7/2014 | Becker et al. |
| 8,772,570 | B2 | 7/2014 | Kawakami et al. |
| 8,784,594 | B2 | 7/2014 | Blessing et al. |
| 8,785,715 | B2 | 7/2014 | Wright et al. |
| 8,791,318 | B2 | 7/2014 | Becker et al. |
| 8,936,584 | B2 | 1/2015 | Zander et al. |
| 2001/0007065 | A1 | 7/2001 | Blanchard et al. |

(56) References Cited

U.S. PATENT DOCUMENTS

| | | |
|---|---|---|
| 2001/0008964 A1 | 7/2001 | Kurata et al. |
| 2001/0016548 A1 | 8/2001 | Kugler et al. |
| 2001/0020157 A1 | 9/2001 | Mizutani et al. |
| 2001/0037101 A1 | 11/2001 | Allan et al. |
| 2001/0044610 A1 | 11/2001 | Kim et al. |
| 2002/0007167 A1 | 1/2002 | Dan et al. |
| 2002/0007169 A1 | 1/2002 | Graef et al. |
| 2002/0016122 A1 | 2/2002 | Curro et al. |
| 2002/0016579 A1 | 2/2002 | Stenberg |
| 2002/0045881 A1 | 4/2002 | Kusibojoska et al. |
| 2002/0056516 A1 | 5/2002 | Ochi |
| 2002/0058919 A1 | 5/2002 | Hamilton et al. |
| 2002/0062112 A1 | 5/2002 | Mizutani |
| 2002/0062115 A1 | 5/2002 | Wada et al. |
| 2002/0062116 A1 | 5/2002 | Mizutani et al. |
| 2002/0065498 A1 | 5/2002 | Ohashi |
| 2002/0072471 A1 | 6/2002 | Ikeuchi et al. |
| 2002/0082575 A1 | 6/2002 | Dan |
| 2002/0087139 A1 | 7/2002 | Popp et al. |
| 2002/0095127 A1 | 7/2002 | Fish et al. |
| 2002/0102392 A1 | 8/2002 | Fish et al. |
| 2002/0115969 A1 | 8/2002 | Maeda et al. |
| 2002/0123728 A1 | 9/2002 | Graef et al. |
| 2002/0123848 A1 | 9/2002 | Schneiderman et al. |
| 2002/0151634 A1 | 10/2002 | Rohrbaugh et al. |
| 2002/0151861 A1 | 10/2002 | Klemp et al. |
| 2002/0173767 A1 | 11/2002 | Popp et al. |
| 2002/0192366 A1 | 12/2002 | Cramer et al. |
| 2002/0197695 A1 | 12/2002 | Glucksmann et al. |
| 2003/0036741 A1 | 2/2003 | Abba et al. |
| 2003/0078553 A1 | 4/2003 | Wada et al. |
| 2003/0084983 A1 | 5/2003 | Rangachari et al. |
| 2003/0088223 A1 | 5/2003 | Vogt et al. |
| 2003/0105190 A1 | 6/2003 | Diehl et al. |
| 2003/0109839 A1 | 6/2003 | Costae et al. |
| 2003/0114811 A1 | 6/2003 | Christen et al. |
| 2003/0114816 A1 | 6/2003 | Underhill et al. |
| 2003/0114818 A1 | 6/2003 | Benecke et al. |
| 2003/0115969 A1 | 6/2003 | Koyano et al. |
| 2003/0120235 A1 | 6/2003 | Boulanger |
| 2003/0120249 A1 | 6/2003 | Wulz et al. |
| 2003/0135176 A1 | 7/2003 | Delzer et al. |
| 2003/0135181 A1 | 7/2003 | Chen et al. |
| 2003/0135182 A1 | 7/2003 | Woon et al. |
| 2003/0139712 A1 | 7/2003 | Dodge, II et al. |
| 2003/0139715 A1 | 7/2003 | Dodge, II et al. |
| 2003/0139718 A1 | 7/2003 | Graef et al. |
| 2003/0144642 A1 | 7/2003 | Dopps et al. |
| 2003/0144644 A1 | 7/2003 | Murai et al. |
| 2003/0148684 A1 | 8/2003 | Cramer et al. |
| 2003/0148694 A1 | 8/2003 | Ghiam |
| 2003/0158530 A1 | 8/2003 | Diehl et al. |
| 2003/0158531 A1 | 8/2003 | Chmielewski |
| 2003/0158532 A1 | 8/2003 | Magee et al. |
| 2003/0167045 A1 | 9/2003 | Graef et al. |
| 2003/0171727 A1 | 9/2003 | Graef et al. |
| 2003/0208175 A1 | 11/2003 | Gross et al. |
| 2003/0225385 A1 | 12/2003 | Glaug et al. |
| 2003/0233082 A1 | 12/2003 | Kline et al. |
| 2003/0236512 A1 | 12/2003 | Baker |
| 2004/0019338 A1 | 1/2004 | Litvay et al. |
| 2004/0022998 A1 | 2/2004 | Miyamoto et al. |
| 2004/0033750 A1 | 2/2004 | Everett et al. |
| 2004/0063367 A1 | 4/2004 | Dodge, II et al. |
| 2004/0064113 A1 | 4/2004 | Erdman |
| 2004/0064115 A1 | 4/2004 | Arora et al. |
| 2004/0064116 A1 | 4/2004 | Arora et al. |
| 2004/0064125 A1 | 4/2004 | Justmann et al. |
| 2004/0065420 A1 | 4/2004 | Graef et al. |
| 2004/0082928 A1 | 4/2004 | Pesce et al. |
| 2004/0097895 A1 | 5/2004 | Busam et al. |
| 2004/0122411 A1 | 6/2004 | Hancock-Cooke |
| 2004/0127131 A1 | 7/2004 | Potnis |
| 2004/0127871 A1 | 7/2004 | Odorzynski et al. |
| 2004/0127872 A1 | 7/2004 | Petryk et al. |
| 2004/0134596 A1 | 7/2004 | Rosati et al. |
| 2004/0138633 A1 | 7/2004 | Mishima et al. |
| 2004/0147890 A1 | 7/2004 | Nakahata et al. |
| 2004/0158212 A1 | 8/2004 | Ponomarenko et al. |
| 2004/0162536 A1 | 8/2004 | Becker et al. |
| 2004/0167486 A1 | 8/2004 | Busam |
| 2004/0167489 A1 | 8/2004 | Kellenberger et al. |
| 2004/0170813 A1 | 9/2004 | Digiacomantonio et al. |
| 2004/0193127 A1 | 9/2004 | Hansson |
| 2004/0215160 A1 | 10/2004 | Chmielewski et al. |
| 2004/0220541 A1 | 11/2004 | Suzuki et al. |
| 2004/0225271 A1 | 11/2004 | Datta et al. |
| 2004/0231065 A1 | 11/2004 | Daniel et al. |
| 2004/0236299 A1 | 11/2004 | Tsang et al. |
| 2004/0236455 A1 | 11/2004 | Woltman et al. |
| 2004/0249355 A1 | 12/2004 | Tanio et al. |
| 2004/0260259 A1 | 12/2004 | Baker |
| 2005/0001929 A1 | 1/2005 | Ochial et al. |
| 2005/0004543 A1 | 1/2005 | Schroer et al. |
| 2005/0004548 A1 | 1/2005 | Otsubo et al. |
| 2005/0008839 A1 | 1/2005 | Cramer et al. |
| 2005/0018258 A1 | 1/2005 | Miyagi et al. |
| 2005/0038401 A1 | 2/2005 | Suzuki et al. |
| 2005/0070867 A1 | 3/2005 | Beruda et al. |
| 2005/0085784 A1 | 4/2005 | LeMinh et al. |
| 2005/0090789 A1 | 4/2005 | Graef et al. |
| 2005/0101929 A1 | 5/2005 | Waksmundzki et al. |
| 2005/0137543 A1 | 6/2005 | Underhill et al. |
| 2005/0148258 A1 | 7/2005 | Chakravarty et al. |
| 2005/0148961 A1 | 7/2005 | Sosalla et al. |
| 2005/0148990 A1 | 7/2005 | Shimoe et al. |
| 2005/0154363 A1 | 7/2005 | Minato et al. |
| 2005/0159720 A1 | 7/2005 | Gentilcore et al. |
| 2005/0165208 A1 | 7/2005 | Popp et al. |
| 2005/0171499 A1 | 8/2005 | Nigam et al. |
| 2005/0176910 A1 | 8/2005 | Jaworek et al. |
| 2005/0203475 A1 | 9/2005 | LaVon et al. |
| 2005/0215752 A1 | 9/2005 | Popp et al. |
| 2005/0229543 A1 | 10/2005 | Tippey |
| 2005/0245684 A1 | 11/2005 | Daniel et al. |
| 2005/0288645 A1 | 12/2005 | LaVon |
| 2005/0288646 A1 | 12/2005 | LaVon |
| 2006/0004334 A1 | 1/2006 | Schlinz et al. |
| 2006/0021695 A1 | 2/2006 | Blessing et al. |
| 2006/0024433 A1 | 2/2006 | Blessing et al. |
| 2006/0069367 A1 | 3/2006 | Waksmundzki et al. |
| 2006/0069371 A1 | 3/2006 | Ohashi et al. |
| 2006/0073969 A1 | 4/2006 | Torii et al. |
| 2006/0081348 A1 | 4/2006 | Graef |
| 2006/0129114 A1 | 6/2006 | Mason, Jr. et al. |
| 2006/0142724 A1 | 6/2006 | Watanabe et al. |
| 2006/0155057 A1 | 7/2006 | Hermeling et al. |
| 2006/0155254 A1 | 7/2006 | Sanz et al. |
| 2006/0167215 A1 | 7/2006 | Hermeling et al. |
| 2006/0177647 A1 | 8/2006 | Schmidt et al. |
| 2006/0178071 A1 | 8/2006 | Schmidt et al. |
| 2006/0184146 A1 | 8/2006 | Suzuki |
| 2006/0184149 A1 | 8/2006 | Kasai et al. |
| 2006/0189954 A1 | 8/2006 | Kudo et al. |
| 2006/0202380 A1 | 9/2006 | Bentley et al. |
| 2006/0206091 A1 | 9/2006 | Cole et al. |
| 2006/0211828 A1 | 9/2006 | Daniel et al. |
| 2006/0240229 A1 | 10/2006 | Erhnsperger et al. |
| 2006/0264860 A1 | 11/2006 | Beck et al. |
| 2006/0264861 A1 | 11/2006 | Lavon et al. |
| 2006/0271010 A1 | 11/2006 | LaVon et al. |
| 2007/0049892 A1 | 1/2007 | Lord et al. |
| 2007/0027436 A1 | 2/2007 | Nakagawa et al. |
| 2007/0032770 A1 | 2/2007 | LaVon et al. |
| 2007/0043191 A1 | 2/2007 | Hermeling et al. |
| 2007/0043330 A1 | 2/2007 | Lankhof et al. |
| 2007/0049897 A1 | 3/2007 | LaVon et al. |
| 2007/0073253 A1 | 3/2007 | Miyama et al. |
| 2007/0078422 A1 | 4/2007 | Glaug et al. |
| 2007/0088308 A1 | 4/2007 | Ehrnsperger et al. |
| 2007/0093164 A1 | 4/2007 | Nakaoka |
| 2007/0093767 A1 | 4/2007 | Carlucci et al. |
| 2007/0100307 A1 | 5/2007 | Nomoto et al. |
| 2007/0118087 A1 | 5/2007 | Flohr et al. |

(56) References Cited

U.S. PATENT DOCUMENTS

| | | |
|---|---|---|
| 2007/0123834 A1 | 5/2007 | McDowall et al. |
| 2007/0156108 A1 | 7/2007 | Becker et al. |
| 2007/0156110 A1 | 7/2007 | Thyfault |
| 2007/0167928 A1 | 7/2007 | Becker et al. |
| 2007/0179464 A1 | 8/2007 | Becker et al. |
| 2007/0179469 A1 | 8/2007 | Takahashi et al. |
| 2007/0191798 A1 | 8/2007 | Glaug et al. |
| 2007/0219521 A1 | 9/2007 | Hird et al. |
| 2007/0219523 A1 | 9/2007 | Bruun et al. |
| 2007/0244455 A1 | 10/2007 | Hansson et al. |
| 2007/0246147 A1 | 10/2007 | Venturino et al. |
| 2007/0255245 A1 | 11/2007 | Asp et al. |
| 2007/0282288 A1 | 12/2007 | Noda et al. |
| 2007/0282290 A1 | 12/2007 | Cole et al. |
| 2007/0282291 A1 | 12/2007 | Cole et al. |
| 2008/0027402 A1 | 1/2008 | Schmidt et al. |
| 2008/0091159 A1 | 4/2008 | Carlucci et al. |
| 2008/0119810 A1 | 5/2008 | Kuroda et al. |
| 2008/0125735 A1 | 5/2008 | Busam et al. |
| 2008/0132864 A1 | 6/2008 | Lawson et al. |
| 2008/0208154 A1 | 8/2008 | Oetjen et al. |
| 2008/0221538 A1 | 9/2008 | Zhao et al. |
| 2008/0221539 A1 | 9/2008 | Zhao et al. |
| 2008/0228158 A1 | 9/2008 | Sue et al. |
| 2008/0262459 A1 | 10/2008 | Kamoto et al. |
| 2008/0268194 A1 | 10/2008 | Kim et al. |
| 2008/0274227 A1 | 11/2008 | Boatman et al. |
| 2008/0281287 A1 | 11/2008 | Marcelo et al. |
| 2008/0294140 A1 | 11/2008 | Ecker et al. |
| 2008/0032035 A1 | 12/2008 | Schmidt et al. |
| 2008/0312617 A1 | 12/2008 | Hundorf et al. |
| 2008/0312618 A1 | 12/2008 | Hundorf et al. |
| 2008/0312619 A1 | 12/2008 | Ashton et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312623 A1 | 12/2008 | Hundorf et al. |
| 2008/0312624 A1 | 12/2008 | Hundorf et al. |
| 2008/0312625 A1 | 12/2008 | Hundorf et al. |
| 2008/0312627 A1 | 12/2008 | Takeuchi et al. |
| 2008/0312628 A1 | 12/2008 | Hundorf et al. |
| 2009/0023848 A1 | 1/2009 | Ahmed et al. |
| 2009/0056867 A1 | 3/2009 | Moriura et al. |
| 2009/0062760 A1 | 3/2009 | Wright et al. |
| 2009/0112173 A1 | 4/2009 | Bissah et al. |
| 2009/0112175 A1 | 4/2009 | Bissah et al. |
| 2009/0157022 A1 | 6/2009 | MacDonald et al. |
| 2009/0192035 A1 | 7/2009 | Stueven et al. |
| 2009/0240220 A1 | 9/2009 | MacDonald et al. |
| 2009/0247977 A1 | 10/2009 | Takeuchi et al. |
| 2009/0258994 A1 | 10/2009 | Stueven et al. |
| 2009/0270825 A1 | 10/2009 | Wciorka et al. |
| 2009/0298963 A1 | 12/2009 | Matsumoto et al. |
| 2009/0299312 A1 | 12/2009 | MacDonald et al. |
| 2009/0306618 A1 | 12/2009 | Kudo et al. |
| 2009/0318884 A1 | 12/2009 | Meyer et al. |
| 2009/0326494 A1 | 12/2009 | Uchida et al. |
| 2010/0051166 A1 | 3/2010 | Hundorf et al. |
| 2010/0062165 A1 | 3/2010 | Suzuki et al. |
| 2010/0062934 A1 | 3/2010 | Suzuki et al. |
| 2010/0063470 A1 | 3/2010 | Suzuki et al. |
| 2010/0068520 A1 | 3/2010 | Stueven |
| 2010/0100065 A1 | 4/2010 | Bianco et al. |
| 2010/0115237 A1 | 5/2010 | Brewer et al. |
| 2010/0121296 A1 | 5/2010 | Noda et al. |
| 2010/0137773 A1 | 6/2010 | Gross et al. |
| 2010/0137823 A1 | 6/2010 | Corneliusson et al. |
| 2010/0198179 A1 | 8/2010 | Noda et al. |
| 2010/0228210 A1 | 9/2010 | Busam et al. |
| 2010/0241096 A1 | 9/2010 | LaVon et al. |
| 2010/0241097 A1 | 9/2010 | Nigam et al. |
| 2010/0262099 A1 | 10/2010 | Klofta |
| 2010/0262104 A1 | 10/2010 | Carlucci et al. |
| 2010/0274208 A1 | 10/2010 | Gabrielii et al. |
| 2010/0274210 A1 | 10/2010 | Noda et al. |
| 2010/0312208 A1 | 12/2010 | Bond et al. |
| 2010/0324521 A1 | 12/2010 | Mukai et al. |
| 2010/0324523 A1 | 12/2010 | Mukai et al. |
| 2011/0041999 A1 | 2/2011 | Hundorf et al. |
| 2011/0060301 A1 | 3/2011 | Nishikawa et al. |
| 2011/0060303 A1 | 3/2011 | Bissah et al. |
| 2011/0066127 A1 | 3/2011 | Kuwano et al. |
| 2011/0071486 A1 | 3/2011 | Harada et al. |
| 2011/0092944 A1 | 4/2011 | Sagisaka et al. |
| 2011/0112498 A1 | 5/2011 | Nhan et al. |
| 2011/0125120 A1 | 5/2011 | Nishitani et al. |
| 2011/0130732 A1 | 6/2011 | Jackels et al. |
| 2011/0130737 A1 | 6/2011 | Sagisaka et al. |
| 2011/0137276 A1 | 6/2011 | Yoshikawa |
| 2011/0144602 A1 | 6/2011 | Long et al. |
| 2011/0144604 A1 | 6/2011 | Noda et al. |
| 2011/0144606 A1 | 6/2011 | Nandrea et al. |
| 2011/0152813 A1 | 6/2011 | Ellingson |
| 2011/0166540 A1 | 7/2011 | Yang |
| 2011/0172630 A1 | 7/2011 | Nomoto et al. |
| 2011/0174430 A1 | 7/2011 | Zhao et al. |
| 2011/0208147 A1 | 8/2011 | Kawakami et al. |
| 2011/0250413 A1 | 10/2011 | Lu et al. |
| 2011/0268932 A1 | 11/2011 | Catalan et al. |
| 2011/0274834 A1 | 11/2011 | Brown et al. |
| 2011/0288513 A1 | 11/2011 | Hundorf et al. |
| 2011/0288514 A1 | 11/2011 | Kuroda et al. |
| 2011/0295222 A1 | 12/2011 | Becker et al. |
| 2011/0319846 A1 | 12/2011 | Rinnert et al. |
| 2011/0319848 A1 | 12/2011 | McKiernan et al. |
| 2011/0319851 A1 | 12/2011 | Kudo et al. |
| 2012/0004633 A1 | 1/2012 | Marcelo et al. |
| 2012/0016326 A1 | 1/2012 | Brennan et al. |
| 2012/0022479 A1 | 1/2012 | Cotton |
| 2012/0035566 A1 | 2/2012 | Sagisaka et al. |
| 2012/0035576 A1 | 2/2012 | Ichikawa et al. |
| 2012/0064792 A1 | 3/2012 | Bauduin |
| 2012/0071848 A1 | 3/2012 | Zhang et al. |
| 2012/0165771 A1 | 6/2012 | Ruman et al. |
| 2012/0165776 A1 | 6/2012 | McGregor et al. |
| 2012/0175056 A1 | 7/2012 | Tsang et al. |
| 2012/0184934 A1 | 7/2012 | Venturino et al. |
| 2012/0232514 A1 | 9/2012 | Baker et al. |
| 2012/0238977 A1 | 9/2012 | Oku et al. |
| 2012/0253306 A1 | 10/2012 | Otsubo et al. |
| 2012/0256750 A1 | 10/2012 | Novak |
| 2012/0271262 A1 | 10/2012 | Venturino et al. |
| 2012/0312491 A1 | 12/2012 | Jackels et al. |
| 2012/0316046 A1 | 12/2012 | Jackels et al. |
| 2012/0316523 A1 | 12/2012 | Hippe et al. |
| 2012/0316526 A1 | 12/2012 | Rosati et al. |
| 2012/0316527 A1 | 12/2012 | Rosati et al. |
| 2012/0316528 A1 | 12/2012 | Kreuzer et al. |
| 2012/0316529 A1 | 12/2012 | Kreuzer et al. |
| 2012/0323195 A1 | 12/2012 | Ehrnsperger et al. |
| 2012/0323201 A1 | 12/2012 | Bissah et al. |
| 2012/0323202 A1 | 12/2012 | Bissah et al. |
| 2013/0035656 A1 | 2/2013 | Moriya et al. |
| 2013/0041334 A1 | 2/2013 | Prioleau et al. |
| 2013/0178811 A1 | 7/2013 | Kikuchi et al. |
| 2013/0211354 A1 | 8/2013 | Tsuji et al. |
| 2013/0218115 A1 | 8/2013 | Katsuragawa et al. |
| 2013/0226119 A1 | 8/2013 | Katsuragawa et al. |
| 2013/0226120 A1 | 8/2013 | Van De Maele |
| 2014/0005622 A1 | 1/2014 | Wirtz et al. |
| 2014/0005623 A1 | 1/2014 | Wirtz et al. |
| 2014/0027066 A1 | 1/2014 | Jackels et al. |
| 2014/0039437 A1 | 2/2014 | Van De Maele |
| 2014/0045683 A1 | 2/2014 | Loick et al. |
| 2014/0135726 A1 | 5/2014 | Busam et al. |
| 2014/0142531 A1 | 5/2014 | Sasayama et al. |
| 2014/0163500 A1 | 6/2014 | Roe et al. |
| 2014/0163501 A1 | 6/2014 | Ehrnsperger et al. |
| 2014/0163502 A1 | 6/2014 | Arizti et al. |
| 2014/0163503 A1 | 6/2014 | Arizti et al. |
| 2014/0163506 A1 | 6/2014 | Roe et al. |
| 2014/0163511 A1 | 6/2014 | Roe et al. |
| 2014/0171893 A1 | 6/2014 | Lawson et al. |
| 2014/0318694 A1 | 10/2014 | Blessing et al. |

(56) References Cited

U.S. PATENT DOCUMENTS

| | | | |
|---|---|---|---|
| 2014/0324008 A1 | 10/2014 | Hundorf et al. | |
| 2014/0358100 A1 | 12/2014 | Remmers et al. | |
| 2015/0065986 A1 | 3/2015 | Blessing et al. | |
| 2015/0080837 A1 | 3/2015 | Rosati et al. | |
| 2015/0250662 A1 | 9/2015 | Isele et al. | |

FOREIGN PATENT DOCUMENTS

| | | |
|---|---|---|
| CA | 2308961 | 11/2000 |
| CA | 2487027 | 12/2003 |
| CA | 2561521 | 3/2007 |
| CA | 2630713 | 11/2008 |
| CA | 2636673 | 1/2009 |
| CA | 2712563 | 8/2010 |
| CA | 2702001 | 10/2010 |
| CN | 1238171 A | 12/1999 |
| CN | 2362468 Y | 2/2000 |
| CN | 1371671 | 2/2001 |
| CN | 2527254 Y | 12/2002 |
| CN | 2535020 Y | 2/2003 |
| CN | 2548609 Y | 5/2003 |
| CN | 1539391 | 10/2004 |
| CN | 1939242 | 4/2007 |
| CN | 101292930 | 10/2008 |
| CN | 201263750 | 7/2009 |
| CN | 201591689 | 9/2010 |
| CN | 201855366 U | 6/2011 |
| DE | 3205931 C2 | 9/1983 |
| DE | 3608114 A1 | 9/1987 |
| DE | 19732499 | 2/1999 |
| DE | 10204937 A1 | 8/2003 |
| EP | 083022 | 7/1983 |
| EP | 149880 | 7/1985 |
| EP | 0149880 A2 | 7/1985 |
| EP | 203289 | 12/1986 |
| EP | 0203289 A2 | 12/1986 |
| EP | 0206208 | 12/1986 |
| EP | 209561 B1 | 1/1987 |
| EP | 297411 B1 | 1/1989 |
| EP | 304957 | 3/1989 |
| EP | 374542 | 6/1990 |
| EP | 394274 | 10/1990 |
| EP | 0403832 | 12/1990 |
| EP | 481322 B1 | 4/1992 |
| EP | 530438 | 3/1993 |
| EP | 547847 | 6/1993 |
| EP | 555346 | 8/1993 |
| EP | 559476 | 9/1993 |
| EP | 591647 B2 | 4/1994 |
| EP | 597273 B1 | 5/1994 |
| EP | 601610 B2 | 6/1994 |
| EP | 632068 | 1/1995 |
| EP | 0640330 A1 | 3/1995 |
| EP | 0668066 | 9/1995 |
| EP | 685214 | 12/1995 |
| EP | 687453 | 12/1995 |
| EP | 0689817 | 1/1996 |
| EP | 0691133 | 1/1996 |
| EP | 0394274 | 7/1996 |
| EP | 724418 | 8/1996 |
| EP | 725613 | 8/1996 |
| EP | 725615 | 8/1996 |
| EP | 725616 | 8/1996 |
| EP | 758543 | 2/1997 |
| EP | 0761194 | 3/1997 |
| EP | 769284 | 4/1997 |
| EP | 0781537 | 7/1997 |
| EP | 783877 B1 | 7/1997 |
| EP | 787472 | 8/1997 |
| EP | 788874 B1 | 8/1997 |
| EP | 796068 | 9/1997 |
| EP | 799004 | 10/1997 |
| EP | 822794 B1 | 2/1998 |
| EP | 826351 | 3/1998 |
| EP | 844861 | 6/1998 |
| EP | 0737055 | 8/1998 |
| EP | 863733 | 9/1998 |
| EP | 971751 | 9/1998 |
| EP | 0875224 | 11/1998 |
| EP | 875224 A1 | 11/1998 |
| EP | 880955 | 12/1998 |
| EP | 891758 | 1/1999 |
| EP | 0893115 | 1/1999 |
| EP | 0724418 | 3/1999 |
| EP | 0725613 | 3/1999 |
| EP | 0725616 | 3/1999 |
| EP | 904755 | 3/1999 |
| EP | 0916327 | 5/1999 |
| EP | 925769 A2 | 6/1999 |
| EP | 933074 | 8/1999 |
| EP | 937736 | 8/1999 |
| EP | 941157 | 9/1999 |
| EP | 947549 | 10/1999 |
| EP | 951887 B1 | 10/1999 |
| EP | 0951890 | 10/1999 |
| EP | 2295493 | 10/1999 |
| EP | 2305749 | 10/1999 |
| EP | 2330152 | 10/1999 |
| EP | 953326 | 11/1999 |
| EP | 0978263 A1 | 2/2000 |
| EP | 985397 B1 | 3/2000 |
| EP | 0778762 | 4/2000 |
| EP | 1005847 | 6/2000 |
| EP | 1008333 | 6/2000 |
| EP | 1013252 B1 | 6/2000 |
| EP | 1018999 | 7/2000 |
| EP | 1019002 B1 | 7/2000 |
| EP | 1019003 B1 | 7/2000 |
| EP | 1022008 | 7/2000 |
| EP | 1023884 | 8/2000 |
| EP | 1053729 | 11/2000 |
| EP | 1059072 A2 | 12/2000 |
| EP | 1063954 | 1/2001 |
| EP | 1071388 | 1/2001 |
| EP | 1078618 | 2/2001 |
| EP | 1088537 A2 | 4/2001 |
| EP | 0796068 | 5/2001 |
| EP | 752892 | 7/2001 |
| EP | 1116479 A2 | 7/2001 |
| EP | 0790839 | 8/2001 |
| EP | 1132069 | 9/2001 |
| EP | 1173128 | 1/2002 |
| EP | 1175194 B1 | 1/2002 |
| EP | 1184018 | 3/2002 |
| EP | 1192312 B1 | 4/2002 |
| EP | 1196122 B2 | 4/2002 |
| EP | 1199059 | 4/2002 |
| EP | 1199327 | 4/2002 |
| EP | 1208824 | 5/2002 |
| EP | 0793469 | 6/2002 |
| EP | 1210925 | 6/2002 |
| EP | 1224922 | 7/2002 |
| EP | 1225857 | 7/2002 |
| EP | 1253231 | 10/2002 |
| EP | 1262531 A1 | 12/2002 |
| EP | 1263374 B1 | 12/2002 |
| EP | 0737056 | 1/2003 |
| EP | 1275358 | 1/2003 |
| EP | 1275361 | 1/2003 |
| EP | 1293187 | 3/2003 |
| EP | 1304986 B1 | 5/2003 |
| EP | 1332742 B1 | 8/2003 |
| EP | 1339368 | 9/2003 |
| EP | 1374817 | 1/2004 |
| EP | 1388334 | 2/2004 |
| EP | 1402863 | 3/2004 |
| EP | 962208 | 8/2004 |
| EP | 1447067 | 8/2004 |
| EP | 1447606 | 8/2004 |
| EP | 1460987 | 9/2004 |
| EP | 963749 | 11/2004 |
| EP | 1495739 | 1/2005 |
| EP | 1524955 | 4/2005 |
| EP | 1920743 | 4/2005 |

(56) References Cited

FOREIGN PATENT DOCUMENTS

| | | |
|---|---|---|
| EP | 1541103 | 6/2005 |
| EP | 1551344 | 7/2005 |
| EP | 1586289 | 10/2005 |
| EP | 1588723 | 10/2005 |
| EP | 1605882 | 12/2005 |
| EP | 1609448 | 12/2005 |
| EP | 1621166 | 2/2006 |
| EP | 1621167 | 2/2006 |
| EP | 1632206 | 3/2006 |
| EP | 1642556 | 4/2006 |
| EP | 1403419 | 5/2006 |
| EP | 1656162 | 5/2006 |
| EP | 1669046 | 6/2006 |
| EP | 1688114 | 8/2006 |
| EP | 2314265 | 8/2006 |
| EP | 1723939 | 11/2006 |
| EP | 1738727 | 1/2007 |
| EP | 1754461 | 2/2007 |
| EP | 1787611 | 5/2007 |
| EP | 1813238 | 8/2007 |
| EP | 2008626 | 12/2008 |
| EP | 2022452 | 2/2009 |
| EP | 2055279 A1 | 5/2009 |
| EP | 2093049 | 8/2009 |
| EP | 2130522 | 12/2009 |
| EP | 1621165 | 4/2010 |
| EP | 2444046 | 4/2012 |
| EP | 2532328 | 12/2012 |
| EP | 2532329 A1 | 12/2012 |
| EP | 2532332 A1 | 12/2012 |
| EP | 2679210 A1 | 1/2014 |
| EP | 2740449 | 6/2014 |
| EP | 2740450 | 6/2014 |
| EP | 2740452 | 6/2014 |
| ES | 2213491 | 8/2004 |
| FR | 2566631 | 1/1986 |
| FR | 2583377 | 12/1986 |
| FR | 2612770 | 9/1988 |
| FR | 2810234 | 12/2001 |
| GB | 1333081 A | 8/1971 |
| GB | 1307441 | 2/1973 |
| GB | 1513055 | 6/1978 |
| GB | 2101468 | 1/1983 |
| GB | 2170108 | 7/1986 |
| GB | 2262873 | 7/1993 |
| GB | 2288540 A | 6/1994 |
| GB | 2354449 | 3/2001 |
| GB | 2452260 A | 10/2007 |
| GR | 851769 | 11/1985 |
| IN | 0984/KOL/1999 | 10/2005 |
| IN | 212479 B | 3/2007 |
| IN | 208543 B | 8/2007 |
| IN | 0980/MUM/2009 | 6/2009 |
| JP | 5572928 U | 5/1980 |
| JP | 598322 U | 1/1984 |
| JP | 630148323 U | 9/1988 |
| JP | 2107250 | 4/1990 |
| JP | 03224481 B2 | 10/1991 |
| JP | 04122256 | 4/1992 |
| JP | 04341368 | 11/1992 |
| JP | 06191505 | 7/1994 |
| JP | 06269475 | 9/1994 |
| JP | 07124193 | 5/1995 |
| JP | 08215629 | 8/1996 |
| JP | 10328232 | 12/1998 |
| JP | 11033056 A | 2/1999 |
| JP | 11318980 | 11/1999 |
| JP | 11320742 | 11/1999 |
| JP | 2000232985 | 8/2000 |
| JP | 2000238161 A | 9/2000 |
| JP | 2001037810 | 2/2001 |
| JP | 2001046435 A | 2/2001 |
| JP | 2001120597 | 5/2001 |
| JP | 2001158074 A | 6/2001 |
| JP | 2001178768 A | 7/2001 |
| JP | 2001198157 | 7/2001 |
| JP | 2001224626 A | 8/2001 |
| JP | 2001277394 | 10/2001 |
| JP | 03420481 B2 | 11/2001 |
| JP | 2001321397 | 11/2001 |
| JP | 2001353174 A | 12/2001 |
| JP | 2002052042 A | 2/2002 |
| JP | 2002065718 | 3/2002 |
| JP | 2002113800 | 4/2002 |
| JP | 2002165832 | 6/2002 |
| JP | 2002165836 | 6/2002 |
| JP | 2002178429 | 6/2002 |
| JP | 2002272769 A | 9/2002 |
| JP | 2002320641 | 11/2002 |
| JP | 2002325792 A | 11/2002 |
| JP | 2002325799 | 11/2002 |
| JP | 2002369841 A | 12/2002 |
| JP | 2003126140 | 5/2003 |
| JP | 2003153955 A | 5/2003 |
| JP | 2003265523 | 9/2003 |
| JP | 2003265524 A | 9/2003 |
| JP | 2003275237 | 9/2003 |
| JP | 2004089269 | 3/2004 |
| JP | 03566012 B2 | 6/2004 |
| JP | 03568146 B2 | 6/2004 |
| JP | 03616077 B2 | 11/2004 |
| JP | 2004337314 A | 12/2004 |
| JP | 2004337385 A | 12/2004 |
| JP | 2004350864 | 12/2004 |
| JP | 03640475 B2 | 1/2005 |
| JP | 2005000312 A | 1/2005 |
| JP | 03660816 B2 | 3/2005 |
| JP | 03676219 B2 | 5/2005 |
| JP | 03688403 B2 | 6/2005 |
| JP | 03705943 B2 | 8/2005 |
| JP | 03719819 B2 | 9/2005 |
| JP | 03724963 B2 | 9/2005 |
| JP | 03725008 B2 | 9/2005 |
| JP | 03737376 B2 | 11/2005 |
| JP | 2006014792 A | 1/2006 |
| JP | 03781617 B2 | 3/2006 |
| JP | 2006110329 A | 4/2006 |
| JP | 2006513824 T | 4/2006 |
| JP | 03801449 B2 | 5/2006 |
| JP | 2006116036 A | 5/2006 |
| JP | 03850102 B2 | 9/2006 |
| JP | 03850207 B2 | 9/2006 |
| JP | 03856941 B2 | 9/2006 |
| JP | 03868628 B2 | 10/2006 |
| JP | 03874499 B2 | 11/2006 |
| JP | 03877702 B2 | 11/2006 |
| JP | 2006325639 A | 12/2006 |
| JP | 2006346021 | 12/2006 |
| JP | 03904356 B2 | 1/2007 |
| JP | 2007007455 A | 1/2007 |
| JP | 2007007456 A | 1/2007 |
| JP | 03926042 B2 | 3/2007 |
| JP | 03934855 B2 | 3/2007 |
| JP | 2007089906 A | 4/2007 |
| JP | 2007105198 A | 4/2007 |
| JP | 2007152033 A | 6/2007 |
| JP | 03986210 B2 | 7/2007 |
| JP | 03986222 B2 | 7/2007 |
| JP | 2007167453 | 7/2007 |
| JP | 2007175515 A | 7/2007 |
| JP | 2007195665 A | 8/2007 |
| JP | 2007267763 A | 10/2007 |
| JP | 2007275491 A | 10/2007 |
| JP | 04035341 B2 | 11/2007 |
| JP | 04058281 B2 | 12/2007 |
| JP | 04061086 B2 | 12/2007 |
| JP | 04092319 B2 | 3/2008 |
| JP | 2008080150 A | 4/2008 |
| JP | 2008093289 A | 4/2008 |
| JP | 04124322 B2 | 5/2008 |
| JP | 2008119081 A | 5/2008 |
| JP | 2008136739 A | 6/2008 |
| JP | 2008136877 A | 6/2008 |
| JP | 04148594 B2 | 7/2008 |

(56) References Cited

FOREIGN PATENT DOCUMENTS

| | | |
|---|---|---|
| JP | 04148620 B2 | 7/2008 |
| JP | 2008154606 A | 7/2008 |
| JP | 04162609 B2 | 8/2008 |
| JP | 04162637 B2 | 8/2008 |
| JP | 04166923 B2 | 8/2008 |
| JP | 04167406 B2 | 8/2008 |
| JP | 04173723 B2 | 8/2008 |
| JP | 04190675 B2 | 9/2008 |
| JP | 04190693 B2 | 9/2008 |
| JP | 04208338 B2 | 10/2008 |
| JP | 2008246089 | 10/2008 |
| JP | 4177770 B2 | 11/2008 |
| JP | 04230971 B2 | 12/2008 |
| JP | 2008295475 A | 12/2008 |
| JP | 2008295713 A | 12/2008 |
| JP | 04261593 B2 | 2/2009 |
| JP | 2009112590 | 5/2009 |
| JP | 04322228 B2 | 6/2009 |
| JP | 2009136601 | 6/2009 |
| JP | 2009142401 A | 7/2009 |
| JP | 2009201878 A | 9/2009 |
| JP | 04392936 B2 | 10/2009 |
| JP | 2009232987 A | 10/2009 |
| JP | 2009261777 A | 11/2009 |
| JP | 2009291473 A | 12/2009 |
| JP | 2009297048 A | 12/2009 |
| JP | 2010017342 | 1/2010 |
| JP | 04458702 B2 | 2/2010 |
| JP | 04459013 B2 | 2/2010 |
| JP | 2010022560 | 2/2010 |
| JP | 04481325 B2 | 3/2010 |
| JP | 2010051654 A | 3/2010 |
| JP | 2010063814 A | 3/2010 |
| JP | 2010063944 A | 3/2010 |
| JP | 04492957 B2 | 4/2010 |
| JP | 2010068954 A | 4/2010 |
| JP | 2010075462 A | 4/2010 |
| JP | 2010082059 A | 4/2010 |
| JP | 2010104545 A | 5/2010 |
| JP | 2010104547 A | 5/2010 |
| JP | 2010110535 A | 5/2010 |
| JP | 2010119454 A | 6/2010 |
| JP | 2010119605 A | 6/2010 |
| JP | 2010119743 A | 6/2010 |
| JP | 2010131131 A | 6/2010 |
| JP | 2010131132 A | 6/2010 |
| JP | 2010131206 | 6/2010 |
| JP | 2010131297 A | 6/2010 |
| JP | 2010136917 A | 6/2010 |
| JP | 2010136973 A | 6/2010 |
| JP | 04540563 B2 | 7/2010 |
| JP | 04587947 B2 | 9/2010 |
| JP | 2010194124 A | 9/2010 |
| JP | 2010201093 | 9/2010 |
| JP | 2010221067 | 10/2010 |
| JP | 4577766 B2 | 11/2010 |
| JP | 04620299 B2 | 11/2010 |
| JP | 04627472 B2 | 11/2010 |
| JP | 04627473 B2 | 11/2010 |
| JP | 04638087 B2 | 12/2010 |
| JP | 04652626 B2 | 12/2010 |
| JP | 2010273842 A | 12/2010 |
| JP | 2010284418 A | 12/2010 |
| JP | 2011000480 A | 1/2011 |
| JP | 2011030700 | 2/2011 |
| JP | 04693574 B2 | 3/2011 |
| JP | 2011067484 A | 4/2011 |
| JP | 2011072720 A | 4/2011 |
| JP | 2011104014 | 6/2011 |
| JP | 2011104122 A | 6/2011 |
| JP | 2011120661 A | 6/2011 |
| JP | 2011125360 A | 6/2011 |
| JP | 2011125537 | 6/2011 |
| JP | 04776516 B2 | 7/2011 |
| JP | 2011130797 A | 7/2011 |
| JP | 2011130799 A | 7/2011 |
| JP | 2011156032 A | 8/2011 |
| JP | 2011156070 A | 8/2011 |
| JP | 2011156254 | 8/2011 |
| JP | 04824882 B2 | 9/2011 |
| JP | 4850272 B2 | 10/2011 |
| JP | 04855533 B2 | 11/2011 |
| JP | 2011239858 | 12/2011 |
| JP | 04931572 B2 | 2/2012 |
| JP | 04937225 B2 | 3/2012 |
| JP | 04953618 B2 | 3/2012 |
| JP | 04969437 B2 | 4/2012 |
| JP | 04969640 B2 | 4/2012 |
| JP | 4971491 B2 | 4/2012 |
| JP | 04974524 B2 | 4/2012 |
| JP | 04979780 B2 | 4/2012 |
| JP | 05016020 B2 | 6/2012 |
| JP | 05027364 B2 | 6/2012 |
| JP | 05031082 B2 | 7/2012 |
| JP | 05042351 B2 | 7/2012 |
| JP | 05043569 B2 | 7/2012 |
| JP | 05043591 B2 | 7/2012 |
| JP | 05046488 B2 | 7/2012 |
| JP | 2012125452 | 7/2012 |
| JP | 2012125625 A | 7/2012 |
| JP | 05053765 B2 | 8/2012 |
| JP | 05070275 B2 | 8/2012 |
| JP | 05079931 B1 | 9/2012 |
| JP | 05080189 B2 | 9/2012 |
| JP | 05084442 B2 | 9/2012 |
| JP | 05084476 B2 | 9/2012 |
| JP | 5085770 B2 | 9/2012 |
| JP | 05089269 B2 | 9/2012 |
| JP | 05113146 B2 | 10/2012 |
| JP | 05129536 B2 | 11/2012 |
| JP | 05105884 B2 | 12/2012 |
| JP | 5715806 B2 | 5/2015 |
| KR | 20010005620 | 1/2001 |
| KR | 20020035634 | 5/2002 |
| KR | 20080028771 | 4/2008 |
| SE | 9400916 | 3/1994 |
| SE | 9704893 | 12/1997 |
| WO | WO9015830 | 12/1990 |
| WO | WO9219198 | 11/1992 |
| WO | WO9321237 | 10/1993 |
| WO | WO9321879 | 11/1993 |
| WO | WO9510996 | 4/1995 |
| WO | WO9511652 | 5/1995 |
| WO | WO9514453 | 6/1995 |
| WO | WO9515139 | 6/1995 |
| WO | WO9516424 | 6/1995 |
| WO | WO9516746 A1 | 6/1995 |
| WO | WO9519753 | 7/1995 |
| WO | WO9521596 | 8/1995 |
| WO | WO9524173 | 9/1995 |
| WO | WO9526209 | 10/1995 |
| WO | WO9529657 | 11/1995 |
| WO | WO9532698 | 12/1995 |
| WO | WO9534329 | 12/1995 |
| WO | WO9616624 | 6/1996 |
| WO | WO9619173 | 6/1996 |
| WO | WO96029967 | 10/1996 |
| WO | WO9711659 | 4/1997 |
| WO | WO9717922 | 5/1997 |
| WO | WO9816179 | 4/1998 |
| WO | WO9816180 | 4/1998 |
| WO | WO9843684 | 10/1998 |
| WO | WO9913813 | 3/1999 |
| WO | WO9934841 | 7/1999 |
| WO | WO9951178 | 10/1999 |
| WO | WO200000235 | 1/2000 |
| WO | WO200032145 | 6/2000 |
| WO | WO200059430 | 10/2000 |
| WO | WO0115647 | 3/2001 |
| WO | WO200126596 | 4/2001 |
| WO | WO200207663 | 1/2002 |
| WO | WO200232962 | 4/2002 |
| WO | WO02064877 A2 | 8/2002 |
| WO | WO2002067809 | 9/2002 |

(56) References Cited

FOREIGN PATENT DOCUMENTS

| | | |
|---|---|---|
| WO | WO2003009794 | 2/2003 |
| WO | WO2003039402 | 5/2003 |
| WO | WO2003053297 | 7/2003 |
| WO | WO03079946 | 10/2003 |
| WO | WO03101622 | 12/2003 |
| WO | WO2003105738 | 12/2003 |
| WO | WO2004021946 | 3/2004 |
| WO | WO2004049995 | 6/2004 |
| WO | WO2004071539 A3 | 8/2004 |
| WO | WO2004084784 | 10/2004 |
| WO | WO2004105664 | 12/2004 |
| WO | WO2005/018694 | 3/2005 |
| WO | WO2005087164 | 9/2005 |
| WO | WO2006104024 | 5/2006 |
| WO | WO2006059922 | 6/2006 |
| WO | WO2006062258 A2 | 6/2006 |
| WO | WO2006066029 | 6/2006 |
| WO | WO2006083584 | 8/2006 |
| WO | WO2006134904 | 12/2006 |
| WO | WO2006134906 | 12/2006 |
| WO | WO2007000315 | 1/2007 |
| WO | WO2007046052 | 4/2007 |
| WO | WO2007047598 | 4/2007 |
| WO | WO2007049725 | 5/2007 |
| WO | WO2007061035 | 5/2007 |
| WO | WO2007142145 | 12/2007 |
| WO | WO2007148502 | 12/2007 |
| WO | WO2008018922 | 2/2008 |
| WO | WO2008065945 | 6/2008 |
| WO | WO2008146749 | 12/2008 |
| WO | WO2008155699 | 12/2008 |
| WO | WO2009004941 | 1/2009 |
| WO | WO2009005431 | 1/2009 |
| WO | WO2009139248 | 1/2009 |
| WO | WO2009139255 | 1/2009 |
| WO | WO2009041223 | 4/2009 |
| WO | WO2009096108 | 8/2009 |
| WO | WO2009107435 | 9/2009 |
| WO | WO2009122830 | 10/2009 |
| WO | WO2009152018 | 12/2009 |
| WO | WO2009155264 | 12/2009 |
| WO | WO2009155265 | 12/2009 |
| WO | WO2010071508 | 6/2010 |
| WO | WO2010074319 | 7/2010 |
| WO | WO2010107096 | 9/2010 |
| WO | WO2010114052 | 10/2010 |
| WO | WO2010117015 | 10/2010 |
| WO | WO2010118272 | 10/2010 |
| WO | WO201153044 | 5/2011 |
| WO | WO2011118725 | 9/2011 |
| WO | WO2011118842 | 9/2011 |
| WO | WO2011145653 | 11/2011 |
| WO | WO2011150955 | 12/2011 |
| WO | WO2011163582 | 12/2011 |
| WO | WO2012002252 | 1/2012 |
| WO | WO2012014436 | 2/2012 |
| WO | WO2012042908 | 4/2012 |
| WO | WO2012043077 | 4/2012 |
| WO | WO2012043078 | 4/2012 |
| WO | WO2012052172 | 4/2012 |
| WO | WO2012043082 | 5/2012 |
| WO | WO2012067216 | 5/2012 |
| WO | WO2012073499 | 6/2012 |
| WO | WO2012074466 | 6/2012 |
| WO | WO201291016 | 7/2012 |
| WO | WO2012090508 | 7/2012 |
| WO | WO2012101934 | 8/2012 |
| WO | WO2012102034 | 8/2012 |
| WO | WO2012117824 | 9/2012 |
| WO | WO2012132460 | 10/2012 |
| WO | WO2012170778 | 12/2012 |
| WO | WO2012170779 | 12/2012 |
| WO | WO2012170781 | 12/2012 |
| WO | WO2012170808 | 12/2012 |
| WO | WO2012174026 | 12/2012 |
| WO | WO2013001788 | 1/2013 |
| WO | WO2013046701 | 4/2013 |
| WO | WO2013060733 | 5/2013 |
| WO | WO2014073636 | 5/2014 |
| WO | WO2014078247 | 5/2014 |

ABSORBENT ARTICLES WITH IMPROVED STRENGTH

FIELD OF THE INVENTION

The present invention generally relates to an absorbent core for use in an absorbent article, and more particularly to an absorbent core with absorbent particulate polymer material.

BACKGROUND OF THE INVENTION

Disposable absorbent articles for receiving and retaining bodily discharges such as urine or feces are generally known in the art. Examples of these include disposable diapers, training pants and adult incontinence articles. Typically, disposable diapers comprise a liquid pervious topsheet that faces the wearer's body, a liquid impervious backsheet that faces the wearer's clothing and an absorbent core interposed between the liquid pervious topsheet and the backsheet. Since their introduction into the market place, disposable diapers have continued to improve regarding comfort, fit and functionalities.

An important component of disposable absorbent articles is the absorbent core structure. The absorbent core structure typically includes absorbent polymer material, such as hydrogel-forming polymer material, also referred to as absorbent gelling material, AGM, or super-absorbent polymer, SAP. This absorbent polymer material ensures that large amounts of bodily fluids, e.g. urine, can be absorbed by the absorbent article during its use and be locked away, thus providing low rewet and good skin dryness.

Traditionally, the absorbent polymer material is incorporated into the absorbent core structure with cellulose or cellulosic fibres. However, over the past years, significant effort has been spent to make thinner absorbent core structures which can still acquire and store large quantities of discharged body fluids, in particular urine. Hereto, it has been proposed to reduce or eliminate these cellulose fibres from the absorbent core structures. To maintain the mechanical stability of the absorbent core structures, small quantities of a fiberized net structure may be added to stabilize the absorbent polymer material.

To reduce stiffness in the absorbent core, the core may also comprise channels, areas substantially free of absorbent polymer particles or absorbent polymer material. The channels provide improved liquid transport, and hence faster acquisition, and more efficient liquid absorbency over the whole absorbent structure. The stiffness of an adhesive may be measured by its G', or storage modulus. While an adhesive with a low G' would have the benefit of being less stiff, an adhesive with a relatively high G' may be relatively less dense, thus providing more volume at the same basis weight.

Therefore, there is a continuing need for core adhesives that have a relatively high G' while still being not too stiff to work as a fiberized net structure or a hot melt adhesive in absorbent articles.

SUMMARY OF THE INVENTION

An absorbent structure for an absorbent article, comprising a first substrate and an absorbent layer supported thereon, said absorbent layer comprising an absorbent material comprising a superabsorbent polymer material; wherein said absorbent structure comprises a fiberized net structure to at least partially immobilize said absorbent layer onto said first substrate, and whereby said fiberized net structure has a storage modulus (G') at 21° C. of greater than about $1.2 \times 10^6$ Pa.

DETAILED DESCRIPTION

Definitions

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. As used herein, the term "body fluids" or "body exudates" includes, but is not limited to, urine, blood, vaginal discharges, breast milk, sweat and fecal matter.

"Absorbent core" or "absorbent structure" means a structure typically disposed between a topsheet and backsheet of an absorbent article for absorbing and containing liquid received by the absorbent article and may comprise one or more substrates, absorbent polymer material disposed on the one or more substrates, and a thermoplastic composition on the absorbent particulate polymer material and at least a portion of the one or more substrates for immobilizing the absorbent particulate polymer material on the one or more substrates. In a multilayer absorbent core, the absorbent core may also include a cover layer. The one or more substrates and the cover layer may comprise a nonwoven. Further, the absorbent core may be substantially cellulose free. The absorbent core does not include an acquisition system, a topsheet, or a backsheet of the absorbent article. In a certain embodiment, the absorbent core may consist essentially of the one or more substrates, the absorbent polymer material, the fiberized net structure, and optionally the cover layer.

"Absorbent polymer material," "absorbent gelling material," "AGM," "superabsorbent," "superabsorbent polymer material", and "superabsorbent material" are used herein interchangeably and refer to cross linked polymeric materials that can absorb at least 5 times their weight of an aqueous 0.9% saline solution as measured using the Centrifuge Retention Capacity test (Edana 441.2-01).

"Absorbent particulate polymer material" is used herein to refer to an absorbent polymer material which is in particulate form so as to be flowable in the dry state.

Figure 8:
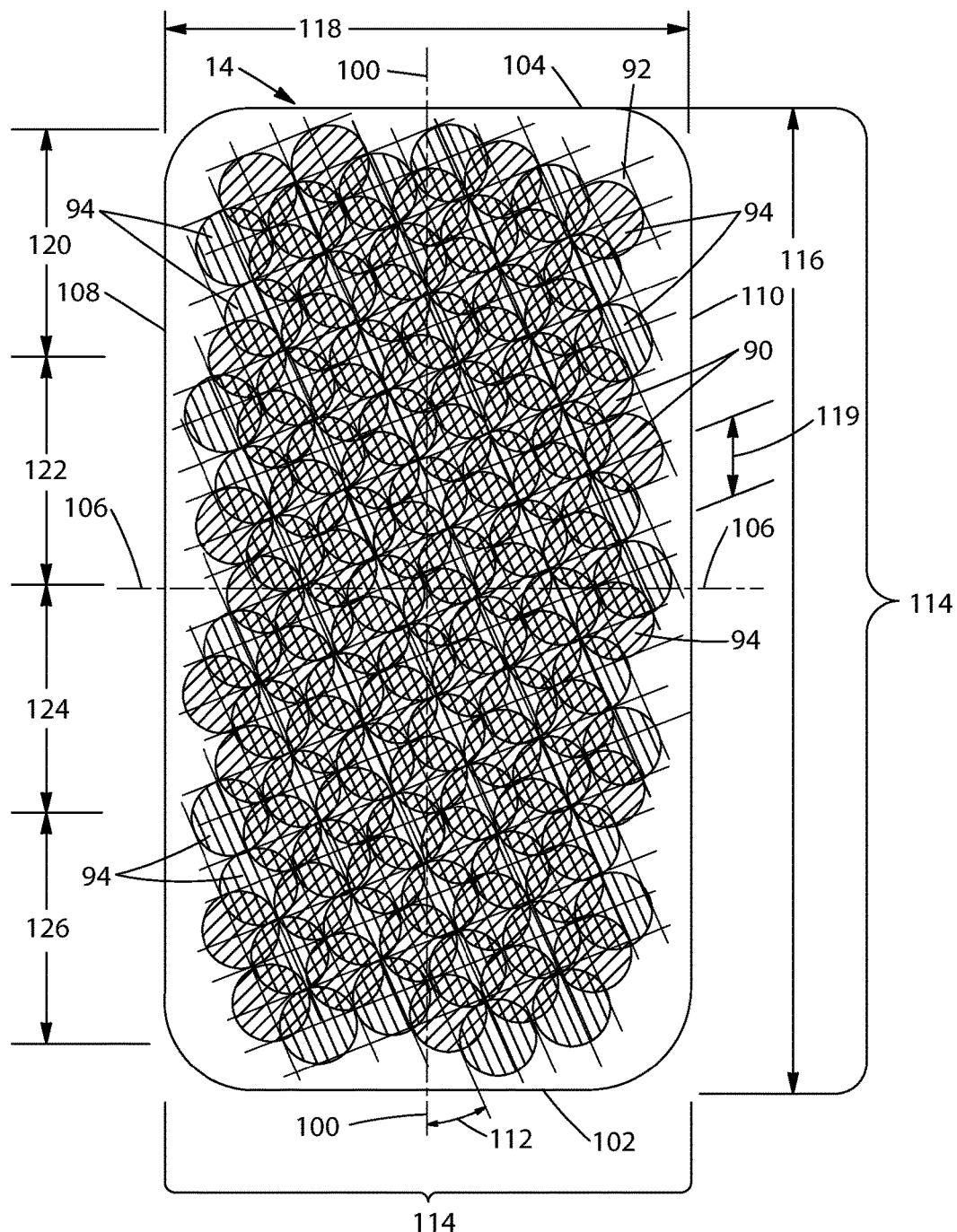
FIG. 8 is a plan view of the absorbent core illustrated in FIGS. 7a and 7b.

"Absorbent particulate polymer material area", "superabsorbent polymer material area" or "absorbent material deposition area" as used herein refers to the area of the core wherein the first substrate and second substrate are separated by a multiplicity of superabsorbent particles. In FIG. 8, the boundary of the absorbent particulate polymer material area is defined by the perimeter of the overlapping circles. There may be some extraneous superabsorbent particles outside of this perimeter between the first substrate and second substrate.

"Airfelt" is used herein to refer to comminuted wood pulp, which is a form of cellulosic fiber.

"Comprise," "comprising," and "comprises" are open ended terms, each specifies the presence of what follows, e.g., a component, but does not preclude the presence of other features, e.g., elements, steps, components known in the art, or disclosed herein.

"Consisting essentially of" is used herein to limit the scope of subject matter, such as that in a claim, to the specified materials or steps and those that do not materially affect the basic and novel characteristics of the subject matter.

"Disposable" is used in its ordinary sense to mean an article that is disposed or discarded after a limited number of usage events over varying lengths of time, for example, less than about 20 events, less than about 10 events, less than about 5 events, or less than about 2 events.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Fiber" and "filament" are used interchangeably.

"Fiberized net structure" as used herein is understood to comprise a polymer composition from which strands or a net structure is formed and applied to the superabsorbent material with the intent to immobilize the superabsorbent material in both the dry and wet state. The fiberized net structure of the present invention forms a fibrous network over the superabsorbent material.

A "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Non-woven fabrics can be formed by many processes such as meltblowing, spunbonding, solvent spinning, electrospinning, and carding. The basis weight of nonwoven fabrics is usually expressed in grams per square meter (gsm).

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

As used herein, the term "substantially" means generally the same or uniform but allowing for or having minor fluctuations from a defined property, definition, etc. For example, small measurable or immeasurable fluctuations in a measured property described herein, such as viscosity, melting point, etc. may result from human error or methodology precision. Other fluctuations are caused by inherent variations in the manufacturing process, thermal history of a formulation, and the like. The compositions of the present invention, nonetheless, would be said to be substantially having the property as reported.

"Substantially cellulose free" is used herein to describe an article, such as an absorbent core, that contains less than 10% by weight cellulosic fibers, less than 5% cellulosic fibers, less than 1% cellulosic fibers, no cellulosic fibers, or no more than an immaterial amount of cellulosic fibers. An immaterial amount of cellulosic material would not materially affect the thinness, flexibility, or absorbency of an absorbent core.

As used herein, the term "substrate" means any item having at least a partially or fully solidified fiber or planar surface. In some cases, a single substrate may be positioned in a way that it is referred to as two or more substrates; for example a folded film or folded non-woven, or two sides of a cardboard sheet folded over, wherein the two sides are adhesively bonded together. The substrates can be impermeable, permeable, porous or nonporous. In some cases, a substrate may be referred to as a supporting sheet.

Absorbent Core

Figure 1:
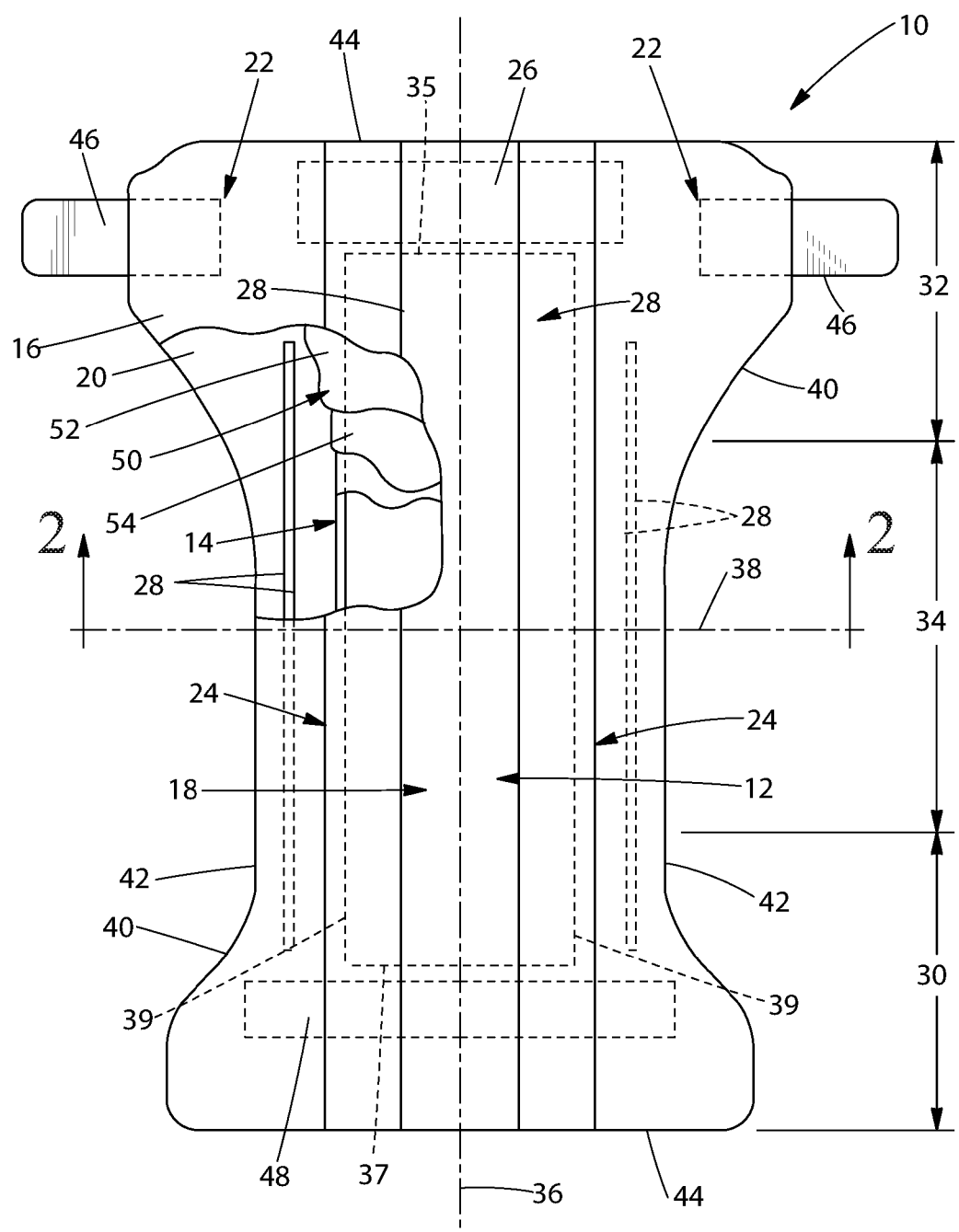
FIG. 1 is a plan view of a diaper in accordance with an embodiment of the present invention.
Figure 2:
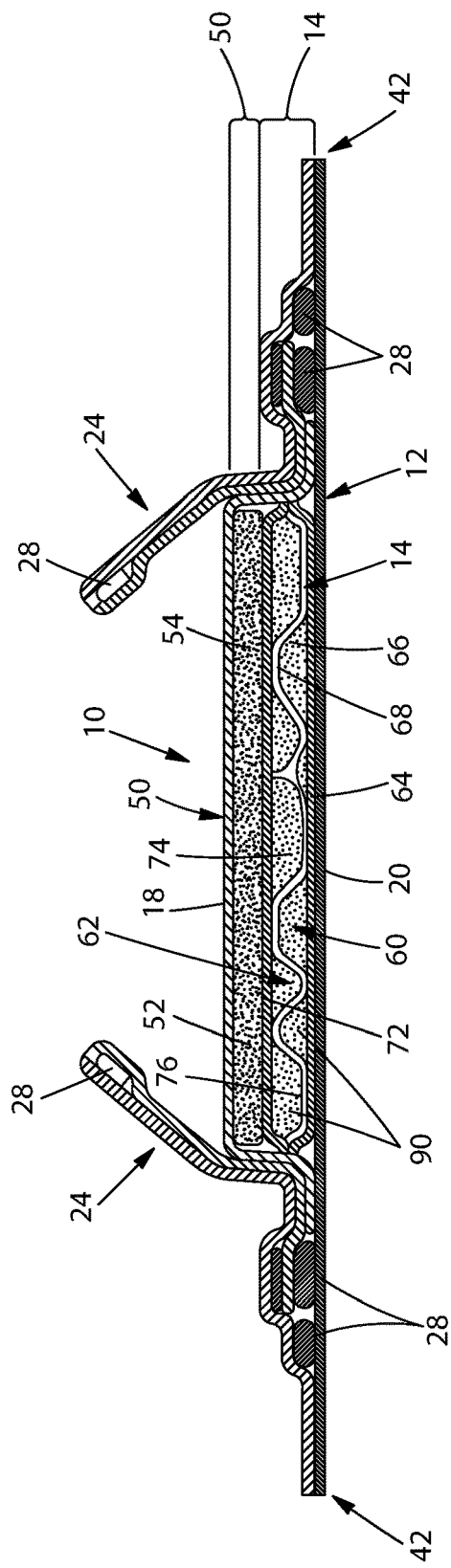
FIG. 2 is a cross sectional view of the diaper shown in FIG. 1 taken along the sectional line 2-2 of FIG. 1.
Figure 3:
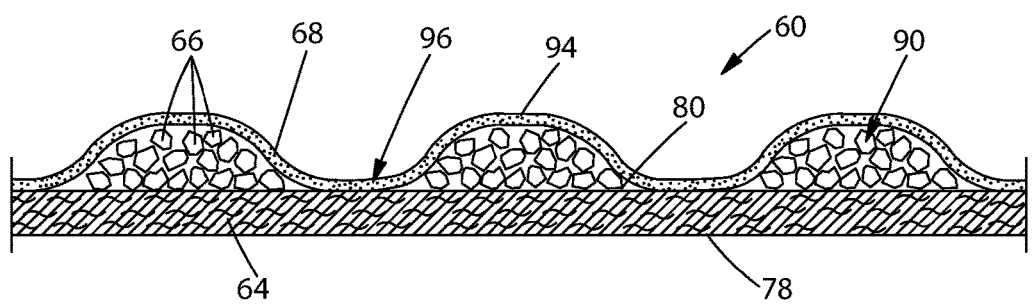
FIG. 3 is a partial cross sectional view of an absorbent core layer in accordance with an embodiment of this invention.

The absorbent core 14 in FIGS. 1-8 generally is disposed between the topsheet 18 and the backsheet 20 and comprises two layers, a first absorbent layer 60 and a second absorbent layer 62. As best shown in FIG. 3, the first absorbent layer 60 of the absorbent core 14 comprises a substrate 64, an absorbent particulate polymer material (such as a superabsorbent polymer material) 66 on the substrate 64, and a thermoplastic composition (such as a fiberized net structure) 68 on the absorbent particulate polymer material 66 and at least portions of the first substrate 64 as a means for covering and immobilizing the absorbent particulate polymer material 66 on the first substrate 64. According to another embodiment illustrated in FIG. 4, the first absorbent layer 60 of the absorbent core 14 may also include a cover layer 70 on the thermoplastic composition 68.

Likewise, as best illustrated in FIG. 2, the second absorbent layer 62 of the absorbent core 14 may also include a substrate 72, an absorbent particulate polymer material (such as a superabsorbent polymer material) 74 on the second substrate 72, and a thermoplastic composition (such as a fiberized net structure) 76 on the absorbent particulate polymer material 74 and at least a portion of the second substrate 72 for immobilizing the absorbent particulate polymer material 74 on the second substrate 72. Although not illustrated, the second absorbent layer 62 may also include a cover layer such as the cover layer 70 illustrated in FIG. 4. The first and second absorbent layers may be combined together such that at least a portion of the fiberized net structure of the first absorbent layer contacts at least a portion of the fiberized net structure of the second absorbent layer.

The substrate 64 of the first absorbent layer 60 may be referred to as a dusting layer, in other embodiments a core cover, and has a first surface or outer surface 78 which faces the backsheet 20 of the diaper 10 and a second surface or inner surface 80 which faces the absorbent particulate polymer material 66. Likewise, the substrate 72 of the second absorbent layer 62 may be referred to as a core cover and has a first surface or outer surface 82 facing the topsheet 18 of the diaper 10 and a second surface or inner surface 84 facing the absorbent particulate polymer material 74. In some embodiments, the first substrate 64 and the second substrate 72 may both be core covers or core wrap material. The first and second substrates 64 and 72 may be adhered to one another with adhesive about the periphery to form an envelope about the absorbent particulate polymer materials 66 and 74 to hold the absorbent particulate polymer material 66 and 74 within the absorbent core 14. The absorbent core may then have a front edge 35, a back edge 37, and two side edges 39. The bonded periphery at the front edge 35 may form a front end seal and the bonded periphery at the back edge 37 may form a back end seal. The thermoplastic composition 68, 76 may in some embodiments be an adhesive material. Any suitable adhesive can be used for this, for example so-called hotmelt adhesives.

According to a certain embodiment, the substrates 64 and 72 of the first and second absorbent layers 60 and 62 may be a nonwoven material, such as those nonwoven materials described above. In certain embodiments, the nonwovens are porous and in one embodiment has a pore size of about 32 microns.

Figure 4:
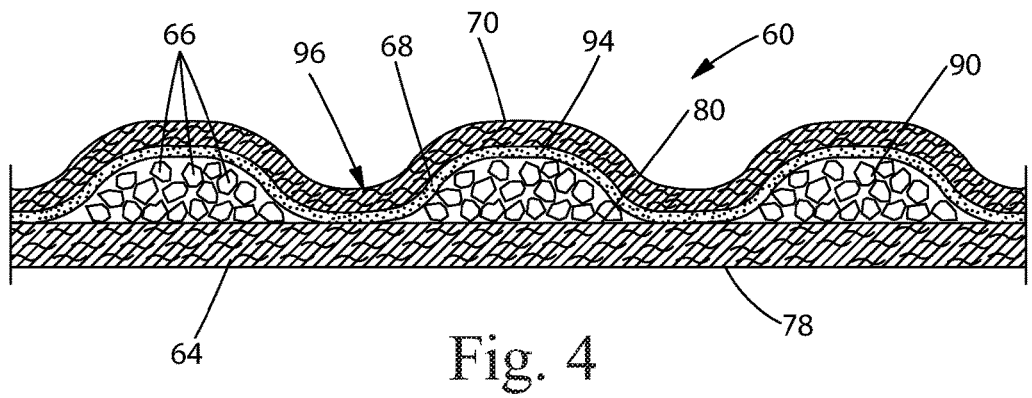
FIG. 4 is a partial cross sectional view of an absorbent core layer in accordance with another embodiment of this invention.
Figure 5:
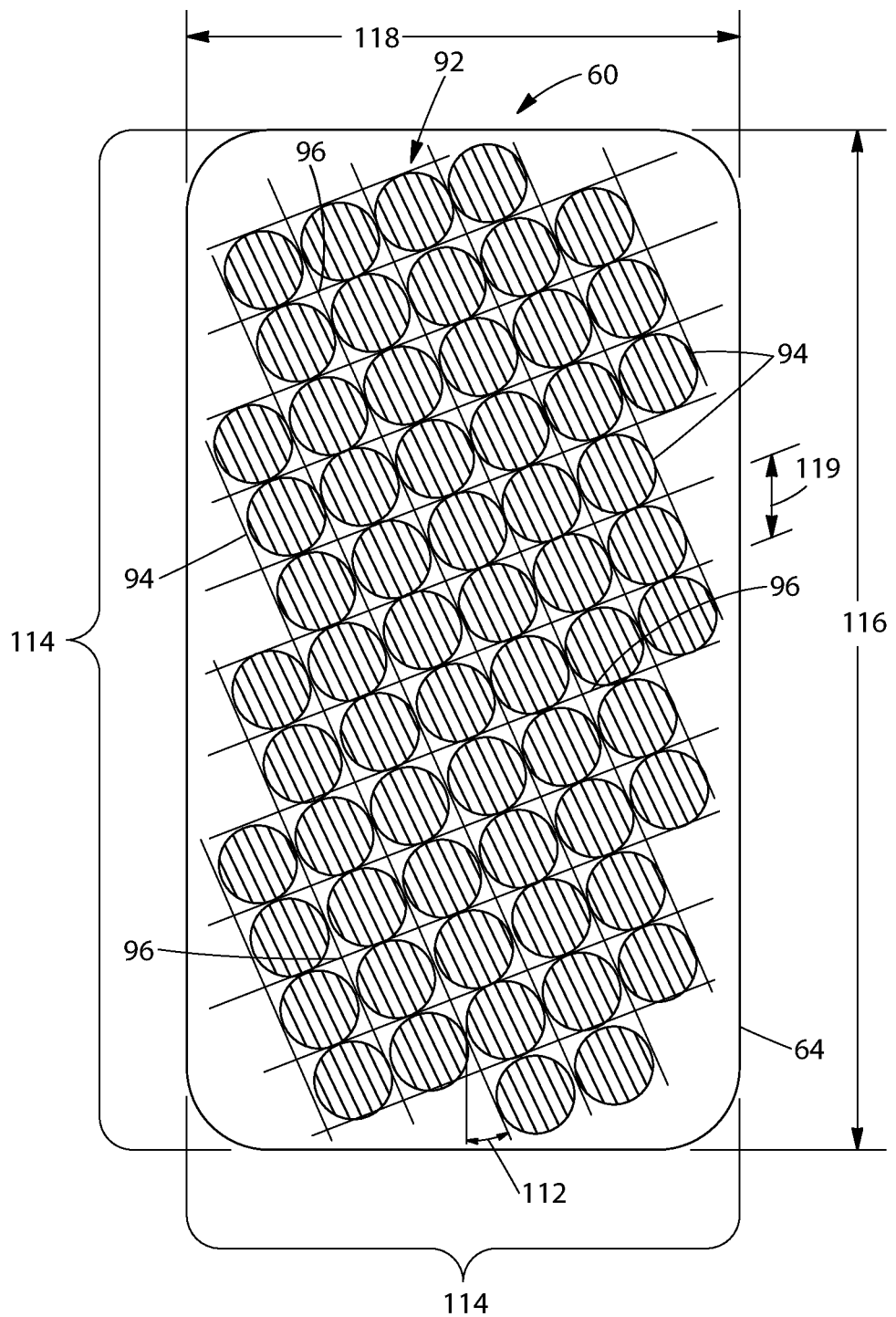
FIG. 5 is a plan view of the absorbent core layer illustrated in FIG. 3.
Figure 6:
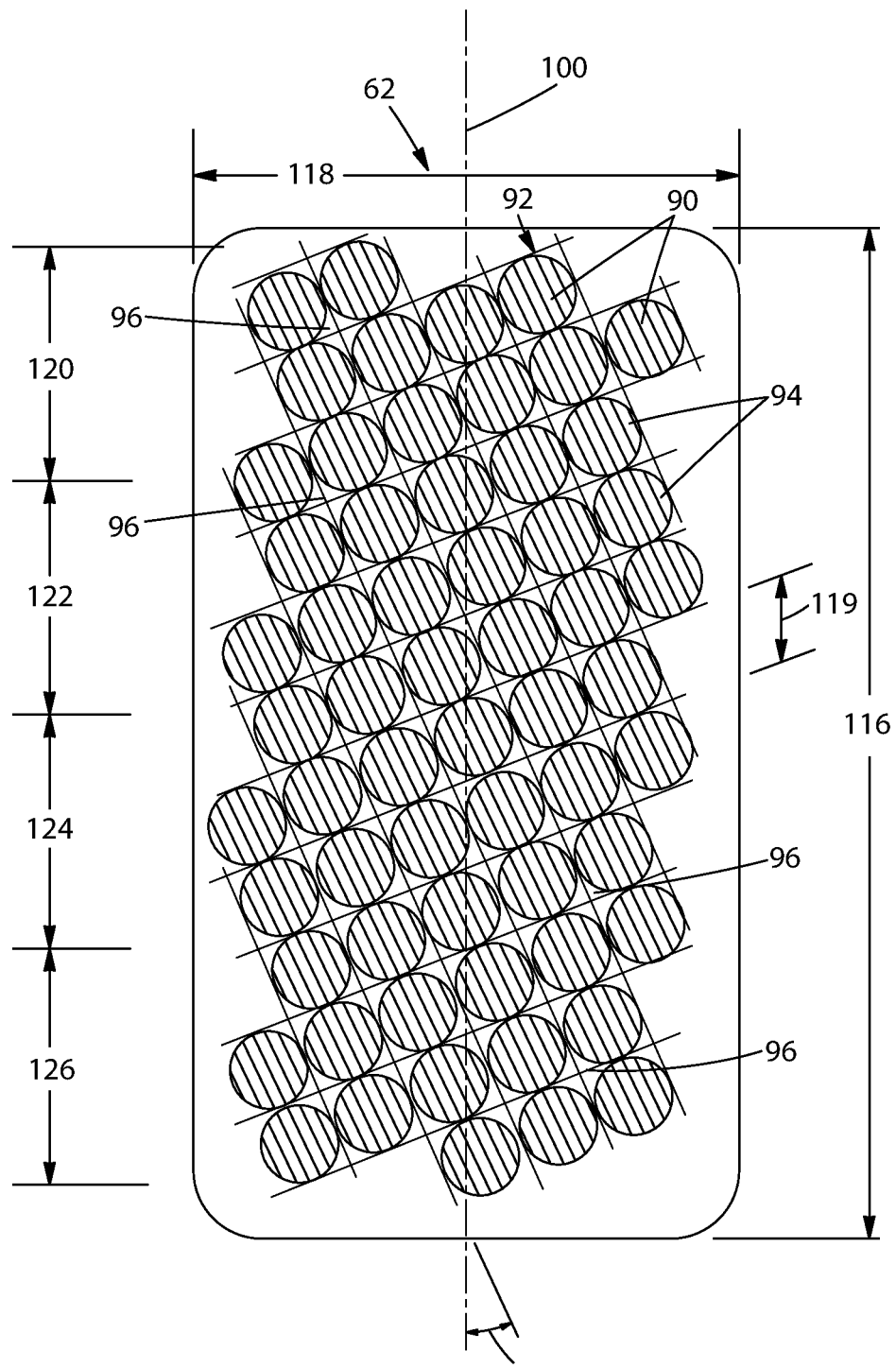
FIG. 6 is a plan view of a second absorbent core layer in accordance with an embodiment of this invention.

The thermoplastic composition 68 and 76 may serve to cover and at least partially immobilize the absorbent particulate polymer material 66 and 74. In one embodiment of the present invention, the thermoplastic composition 68 and 76 can be disposed essentially uniformly within the absorbent particulate polymer material 66 and 74, between the particles of the superabsorbent material. However, in a certain embodiment, the thermoplastic composition 68 and 76 may be provided as a fibrous net structure which is at least partially in contact with the absorbent particulate polymer material 66 and 74 and partially in contact with the substrate layers 64 and 72 of the first and second absorbent layers 60 and 62. FIGS. 3, 4, and 7 show such a structure, and in that structure, the absorbent particulate polymer material 66 and 74 is provided as a discontinuous layer, and a layer of fibrous thermoplastic composition 68 and 76 is laid down onto the layer of absorbent particulate polymer material 66 and 74, such that the thermoplastic composition 68 and 76 is in direct contact with the absorbent particulate polymer material 66 and 74, but also in direct contact with the second surfaces 80 and 84 of the substrates 64 and 72, where the substrates are not covered by the absorbent particulate polymer material 66 and 74. The fiberized net structures of each substrate, 68 and 76, may essentially be one fiberized net structure, each contacting the other. This imparts an essentially three-dimensional structure to the fibrous net structures 68 and 76, which in itself is essentially a two-dimensional structure of relatively small thickness, as compared to the dimension in length and width directions. In other words, the thermoplastic composition 68 and 76 undulates between the absorbent particulate polymer material 66 and 74 and the second surfaces of the substrates 64 and 72, forming a fiberized net structure 68 and 76.

The thermoplastic composition 68 and 76 may provide cavities to cover the absorbent particulate polymer material 66 and 74, and thereby immobilize the material. In a further aspect, the thermoplastic composition 68 and 76 may bond to the substrates 64 and 72 and thus affix the absorbent particulate polymer material 66 and 74 to the substrates 64 and 72. Thus, in accordance with certain embodiments, the thermoplastic composition 68 and 76 immobilizes the absorbent particulate polymer material 66 and 74 when wet, such that the absorbent core 14 achieves an absorbent particulate polymer material loss of no more than about 70%, 60%, 50%, 40%, 30%, 20%, 10% according to the Wet Immobilization Test described herein. Some thermoplastic compositions will also penetrate into both the absorbent particulate polymer material 66 and 74 and the substrates 64 and 72, thus providing for further immobilization and affixation. Of course, while the thermoplastic compositions disclosed herein provide a much improved wet immobilization (i.e., immobilization of absorbent material when the article is wet or at least partially loaded), these thermoplastic compositions may also provide a very good immobilization of absorbent material when the absorbent core 14 is dry. The thermoplastic adhesive material 68 and 76 may also be referred to as a hot melt adhesive. As noted above, in some embodiments, the thermoplastic composition is an adhesive, and in other embodiments, it may be a fiberized net structure, a film, nanofibers, and/or other forms.

The thermoplastic composition may function as a fibrous structure that entraps the absorbent particulate polymer 66 and prevents substantial movement. Thermoplastic compositions most useful for immobilizing the absorbent particulate polymer material 66 and 74 combine good cohesion and good flexibility to reduce the likelihood that the thermoplastic composition breaks in response to strain. Good adhesion ability may promote good contact between the thermoplastic composition 68 and 76 and the absorbent particulate polymer material 66 and 74 and the substrates 64 and 72. When the absorbent core 14 absorbs liquid, the absorbent particulate polymer material 66 and 74 swells and subjects the thermoplastic composition 68 and 76 to external forces. In certain embodiments, the thermoplastic composition 68 and 76 may allow for such swelling, without imparting too many compressive forces, which would restrain the absorbent particulate polymer material 66 and 74 from swelling. Elasticity and flexibility in the thermoplastic composition also promotes overall article flexibility and its preferred ability to conform to the wearer. The thermoplastic composition may have high G' values, but may still be not too stiff to work as a fiberized structure in absorbent articles. A composition with a relatively high G', such as greater than $1.2 \times 10^6$ Pa, means a stiffer composition. The thermoplastic compositions in the present invention may be less dense, thus providing more volume at the same basis weight. This is particularly true for compositions comprising polyolefins.

The absorbent core 14 may also comprise an auxiliary adhesive which is not illustrated in the figures. The auxiliary adhesive may be deposited on the first and second substrates 64 and 72 of the respective first and second absorbent layers 60 and 62 before application of the absorbent particulate polymer material 66 and 74 for enhancing adhesion of the absorbent particulate polymer materials 66 and 74 and the thermoplastic composition 68 and 76 to the respective substrates 64 and 72. It may be preferable to deposit the auxiliary adhesive on a nonwoven that is the most hydrophilic for improved bonding. The auxiliary glue may also aid in immobilizing the absorbent particulate polymer material 66 and 74 and may comprise the same thermoplastic composition as described hereinabove or may also comprise other or additional adhesives including but not limited to sprayable hot melt adhesives. The auxiliary glue may be applied to the substrates 64 and 72 by any suitable means, but according to certain embodiments, may be applied in about 0.5 to about 1 mm wide slots spaced about 0.5 to about 2 mm apart.

In some embodiments, the absorbent core may comprise a single thermoplastic composition that acts in some places as a fiberized net structure and in other places as a more traditional hot melt adhesive. For example, such a thermoplastic composition may provide the immobilization of the absorbent particulate polymer material 66 as discussed above, while also providing adhesive strength for the front end seal and back end seal, for the side edges of the core, and/or for the substrates 64 and 72 in general, such as discussed for the auxiliary adhesive. In some situations, no auxiliary adhesive would be necessary. In other embodiments, one thermoplastic composition may be used to provide a fiberized net structure to immobilize the absorbent particulate polymer, while an auxiliary adhesive is used in conjunction with the thermoplastic composition to adhere materials in other areas in the core.

The fiberized net structure composition and/or any hot melt adhesive may be applied in the absorbent particulate polymer material area at a basis weight of from about 2 grams/meter$^2$ to about 7 grams/meter$^2$ (gsm), in some embodiments from about 2 gsm to about 9 gsm, or from about 4 gsm to about 9 gsm. This may be a combined basis weight from application on a first and a second substrate, for example, 4 and 3 gsm, respectively, or 5 and 4 gsm, respectively. The auxiliary adhesive may be applied in the absorbent particulate polymer material area in any amount from 0 to about 8 gsm, in some embodiments, about 5 gsm, in other embodiments about 8 gsm. The total amount of adhesive and fiberized net structure material may be from about 2 gsm to about 15 gsm in the absorbent particulate polymer material area. The front end seal may have from about 10 gsm to about 35 gsm of adhesive. Similarly, the back end seal may have from about 10 gsm to about 35 gsm of adhesive. In some embodiments, either or both of the front and back end seals may have from about 5 gsm to 15 gsm of adhesive. In some embodiments, the amount of adhesive in an end seal may be a combination of the fiberized net structure composition, the auxiliary adhesive, and the end seal adhesive.

In certain embodiments, the thermoplastic composition 68 and 76 may comprise, in its entirety, a single thermoplastic polymer or a blend of thermoplastic polymers, having a softening point, as determined by the ASTM Method D-28-99 "Ring and Ball Softening Point", in the range between 50° C. and 300° C., in some embodiments in the range between 75 and 150° C., or alternatively the thermoplastic composition may be a hot melt adhesive comprising at least one thermoplastic polymer in combination with other thermoplastic diluents such as tackifying resins, plasticizers and additives such as antioxidants. In certain embodiments, the thermoplastic polymer composition has typically a molecular weight (Mw) of more than 10,000 and a glass transition temperature (Tg) usually below room temperature or $-20°$ C.$>$Tg$<18°$ C. In certain embodiments, typical concentrations of the polymer in a hot melt are in the range of about 10 to about 60% by weight. In certain embodiments, thermoplastic polymers may be water insensitive.

Suitable thermoplastic polymers that may be employed are metallocene polyolefins, such as ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins. Also suitable thermoplastic polymers may include styrenic block copolymers, such as SIS, SEBS, and SBS, combinations of styrenic block copolymers, and combinations of styrenic block copolymers and polyolefins.

Also suitable, for example, is NW1414 available from H.B. Fuller Company. Also appropriate are propylene-based polymers. The thermoplastic polymers, thermoplastic composition, and/or any auxiliary adhesive may be exemplified by the materials described in U.S. 2014/0358100. The material may include two different propylene-based polymers. The propylene-based polymers may be propylene homopolymers, or one or more of the two different propylene-based polymers may be copolymers with one or more other monomers (e.g., ethylene, butene, pentene, octene, etc.). The propylene-based polymers may be based entirely on olefins, i.e., do not contain any functional groups. The propylene-based polymers may comprise greater than about 75% by weight propylene or even greater than about 80% by weight propylene. The propylene-based polymers may have a polydispersity (Mw/Mn) of less than about 5, less than about 3, or even about 2. Propylene-based polymers may have a density of no greater than about 0.89, or no greater than about 0.88. The thermoplastic composition and/or adhesives may comprise a first propylene-based polymer that has a Mw (molecular weight) of at most about 75,000, at most about 60,000, at most about 50,000, or between about 30,000 and about 70,000, wherein the first propylene-based polymer may be present in the overall composition in an amount of at least about 20%, 25%, or 30% by weight, or from about 15% to about 50% by weight, or from about 25% to about 45% by weight. Exemplary first polymers may include LICOCENE PP1602 and LICOCENE PP2602 both available from Clariant International Ltd. (Muttenz, Switzerland) and L-MODU X400S and L-MODU X600S available from Idemitsu Kosan Co., Ltd. (Japan). The composition may also comprise a second propylene-based polymer that has a Mw of at least about 100,000, at least about 125,000, at least about 150,000, or between about 125,000 and about 400,000, or between about 150,000 and about 250,000. The second propylene-based polymer may be present in the composition in an amount of at most about 20% by weight, at most about 15%, by weight, at most about 8% by weight, or from about 2% by weight to about 15% by weight, or from about 3% by weight to about 10% by weight. Exemplary second polymers may include VISTAMAXX 6202 and VISTAMAXX 6102 available from ExxonMobil Chemical (Houston, Tex.) and VERSIFY 3300 available from Dow Chemical Company (Houston, Tex.). The total propylene-based polymer content of a composition may be at least about 20% by weight, at least about 25% by weight, at least about 30% by weight, at least about 35% by weight, or from about 35% by weight to about 50% by weight. The composition may include a third polymer, such as a styrenic block copolymer, which may be hydrogenated. Useful hydrogenated styrene block copolymers include, e.g., styrene-ethylene/butadiene-styrene block copolymer, styrene-ethylene/propylene-styrene block copolymer, styrene-ethylene/ethylene-propylene-styrene block copolymer, and combinations thereof. The styrenic block copolymer may have a styrene content of less than about 20% by weight, less than about 18% by weight, or even less than about 15% by weight. The styrene block copolymer may also have a Melt Flow when tested according to ASTM 1238 (230° C., 5 kg) of less than about 25 g/10 min, less than about 20 g/10 min, less than about 10 g/10 min, or even less than about 5 g/10 min. Exemplary hydrogenated styrene block copolymers are commercially available under a variety of trade designations including, e.g., the SEPTON series of trade designations from Kuraray Co., Ltd (Houston, Tex.) including, e.g., SEPTON S2063 and S2007 hydrogenated styrene-isoprene-styrene block copolymers, the KRATON G series of trade designations from Kraton Performance Polymers Inc. (Houston, Tex.) including, e.g., KRATON G 1645M, KRATON G 1657 styrene-ethylene/butadiene-styrene block copolymers. The materials may include no greater than about 20% by weight, no greater than about 15% by weight, from about 2% to 20% by weight, or even from about 5% to 15% by weight of the third polymer. Also, the composition may include and crystalline polyethylene oxide.

In some embodiments, the tackifying resin has a Mw below 5,000 and a Tg above room temperature, with concentrations of the resin in a hot melt are in the range of about 30 to about 60%. Suitable classes of tackifying resins include, for example, aromatic, aliphatic and cycloaliphatic hydrocarbon resins, mixed aromatic and aliphatic modified hydrocarbon resins, aromatic modified aliphatic hydrocarbon resins, and hydrogenated versions thereof; terpenes, modified terpenes and hydrogenated versions thereof; natural rosins, modified rosins, rosin esters, and hydrogenated versions thereof, and combinations thereof. Suitable tackifying agents include, for example, the ESCOREZ series of trade designations from Exxon Mobil Chemical Company (Houston, Tex.) including ESCOREZ 5400 and ESCOREZ 5600, the EASTOTAC series of trade designations from Eastman Chemical (Kingsport, Tenn.) including EASTOTAC H-100R and EASTOTAC H-100L, and the WINGTACK series of trade designations from Cray Valley HSC (Exton, Pa.) including WINGTACK 86, WINGTACK EXTRA, and WINTACK 95 and the PICCOTAC and KRISTALEX series of trade designations from Eastman Chemical Company (Kingsport, Tenn.) including, e.g., PICCOTAC 8095 and KRISTALEX 3100. In some embodiments, the composition may comprise from at least about 10% by weight, at least about 20% by weight, or from about 5% by weight to about 60% by weight, or from about 10% by weight to about 40% by weight tackifying agent. In some embodiments, the thermoplastic composition, either in an adhesive form or as a fiberized net structure, may be free of any tackifying agent, or may be substantially tackifier-free.

In some embodiments, the plasticizer has a low Mw of typically less than 1,000 and a Tg below room temperature, with a typical concentration of about 0 to about 20%, in some embodiments, about 10 to about 20%. Suitable plasticizers include, for example, naphthenic oils, paraffinic oils (e.g., cycloparaffin oils), mineral oils, paraffinic adipate esters, olefin oligomers (e.g., oligomers of polypropylene, polybutene, and hydrogenated polyisoprene), polybutenes, polyisoprene, hydrogenated polyisoprene, polybutadiene, benzoate esters, animal oil, plant oils (e.g. castor oil, soybean oil), derivatives of oils, glycerol esters of fatty acids, polyesters, polyethers, lactic acid derivatives and combinations thereof. Exemplary commercially available plasticizers include CALSOL 550 oil from Calumet Specialty Products Partners, LP (Indianapolis, Ind.), KAYDOL OIL from Sonneborn (Tarrytown N.Y.) PARAPOL polybutene from Exxon Mobil Chemical Company (Houston, Tex.), OPPANOL polyisobutylene from BASF (Ludwigsjhafen, Germany), KRYSTOL 550 mineral oil from Petrochem Carless Limited (Surrey, England) and PURETOL 15 mineral oil from Petro Canada Lubricants Inc. (Mississauga, Ontario). The plasticizer may be present in an amount at most about 25% by weight, 20% by weight, 18% by weight, or from about 5% to about 30% by weight, or from about 10% to about 20% by weight. The adhesive/fiberized net structure composition may include a wax. Useful classes of wax may include, e.g., paraffin waxes, microcrystalline waxes, high density low molecular weight polyethylene waxes, by-product polyethylene waxes, polypropylene waxes, Fischer-Tropsch waxes, oxidized Fischer-Tropsch waxes, functionalized waxes such as acid, anhydride, and hydroxyl modified waxes, animal waxes, vegetable waxes (e.g., soy wax) and combinations thereof. Useful waxes are commercially available from a variety of suppliers including EPOLENE N and C series of trade designations from Westlake Chemical Corporation (Houston, Tex.) including e.g., EPOLENE N-21 and the LICOCENE series of trade designations from Clariant International Ltd. (Muttenz, Switzerland) including e.g. TP LICOCENE PP 6102. The composition may include no greater than about 10% by weight, no greater than about 5% by weight, from about 1% by weight to about 10% by weight, or even from about 1% to about 5% by weight wax. The adhesive/fiberized net structure composition may also include additional components including, e.g., stabilizers, antioxidants, additional polymers (e.g., styrenic block copolymers, amorphous poly-alpha olefins, polyethylene copolymers), adhesion promoters, ultraviolet light stabilizers, corrosion inhibitors, colorants (e.g., pigments and dyes), fillers, surfactants, wetness indicators, superabsorbents and combinations thereof. Useful antioxidants include, e.g., pentaerythritol tetrakis[3,(3,5-di-tert-butyl-4-hydroxyphenyl) propionate], 2,2'-methylene bis(4-methyl-6-tert-butylphenol), phosphites including, e.g., tris-(p-nonylphenyl)-phosphite (TNPP) and bis(2,4-di-tert-butylphenyl)4,4'-diphenylene-diphosphonite, di-stearyl-3,3'-thiodipropionate (DSTDP), and combinations thereof. Useful antioxidants are commercially available under a variety of trade designations including, e.g., the IRGANOX series of trade designations including, e.g., IRGANOX 1010, IRGANOX 565, and IRGANOX 1076 hindered phenolic antioxidants and IRGAFOS 168 phosphite antioxidant, all of which are available from BASF Corporation (Florham Park, N.J.), and ETHYL 702 4,4'-methylene bis(2,6-di-tert-butylphenol). When present, the composition preferably includes from about 0.1% by weight to about 2% by weight antioxidant.

The thermoplastic composition 68, 76 may in some embodiments be an adhesive material. Any suitable adhesive can be used for this, for example so-called hotmelt adhesive. For example, Henkel DM3800, can be used.

In certain embodiments, the thermoplastic composition 68 and 76 is present in the form of fibers. In some embodiments, the fiberized net structure will have a range of thickness from about 1 to about 90 micrometers, in some embodiments, from about 1 to about 75 micrometers, in some embodiments from about 1 to about 50 micrometers, and in still other embodiments from about 1 to about 35 micrometers, and an average maximum fiber-to-fiber distance of about 0.1 mm to about 5 mm or about 0.3 mm to about 6 mm. The average fiber thickness may be about 30 micrometers, or may be from about 15 to about 45 micrometers. To improve the adhesion of the thermoplastic composition as an adhesive material to the substrates 64 and 72 or to any other layer, in particular any other non-woven layer, such layers may be pre-treated with an auxiliary adhesive.

When the absorbent article contains channels (as discussed below), the thermoplastic composition and/or adhesive material(s) may not only help in immobilizing the absorbent material on the supporting sheet or substrate, but it may also help in maintaining the integrity of the channels in the absorbent structure absorbent core during storage and/or during use of the disposable article. The thermoplastic and/or adhesive materials may help to avoid that a significant amount of absorbent material migrates into the channels. Furthermore, when the materials are applied in the channels or on the supporting sheet portions coinciding with the channels it may thereby help to adhere the substrate of the absorbent structure to said walls, and/or to a further material, as will be described in further details below. In some embodiments, an adhesive may be a thermoplastic adhesive material. That is, in some embodiments, a thermoplastic composition may be applied as fibers, forming a fibrous network that immobilizes the absorbent material on the substrates, or supporting sheet. The thermoplastic fibers may be partially in contact with the substrate of the absorbent structure; if applied also in the channels, it (further) anchors the absorbent layer to the substrate.

The thermoplastic composition material may for example allow for such swelling, without breaking and without imparting too many compressive forces, which would restrain the absorbent polymer particles from swelling.

In certain embodiments, the thermoplastic composition 68 and 76, and/or any auxiliary adhesive, will meet at least one, or several, or all of the following parameters:

A typical parameter for a thermoplastic composition suitable for use in the present disclosure can be a loss Factortan δ at 60° C. (6.28 mrad/s) of below the value of 1, or below the value of 0.5. The loss Factortan δ at 60° C. is correlated with the cohesive character of an adhesive at elevated ambient temperatures. The lower tan δ, the more an adhesive behaves like a solid rather than a liquid, i.e. the lower its tendency to flow or to migrate and the lower the tendency of an adhesive superstructure as described herein to deteriorate or even to collapse over time. This value is hence particularly important if the absorbent article is used in a hot climate.

It may be beneficial, e.g. for process reasons and/or performance reasons, that the thermoplastic composition material has a viscosity of between 800 and 8000 mPa·s, or from 1000 mPa·s to 1400 mPa·s or from 1500 mPa·s to 7000 mPa·s or to 5000 mPa·s or to 3000 mPa·s or to 2500 mPa·s, at 163° C., as measurable by ASTM D3236-88, using spindle 27, 20 pmp, 20 minutes preheating at the temperature, and stirring for 10 min.

The thermoplastic composition may have a softening point of between 60° C. and 150° C., or between 75° C. and 135° C., or between 90° C. and 130° C., or between 100° C. and 115° C., as can be determined with ASTM E28-99 (Herzog method; using glycerine).

In one embodiment herein, the thermoplastic component may be hydrophilic, having a contact angle of less than 90°, or less than 80° or less than 75° or less than 70°, as measurable with ASTM D 5725-99.

The cover layer 70 shown in FIG. 4 may comprise the same material as the substrates 64 and 72, or may comprise a different material. In certain embodiments, suitable materials for the cover layer 70 are the non-woven materials, typically the materials described above as useful for the substrates 64 and 72. The nonwovens may be hydrophilic and/or hydrophobic.

Figure 11:
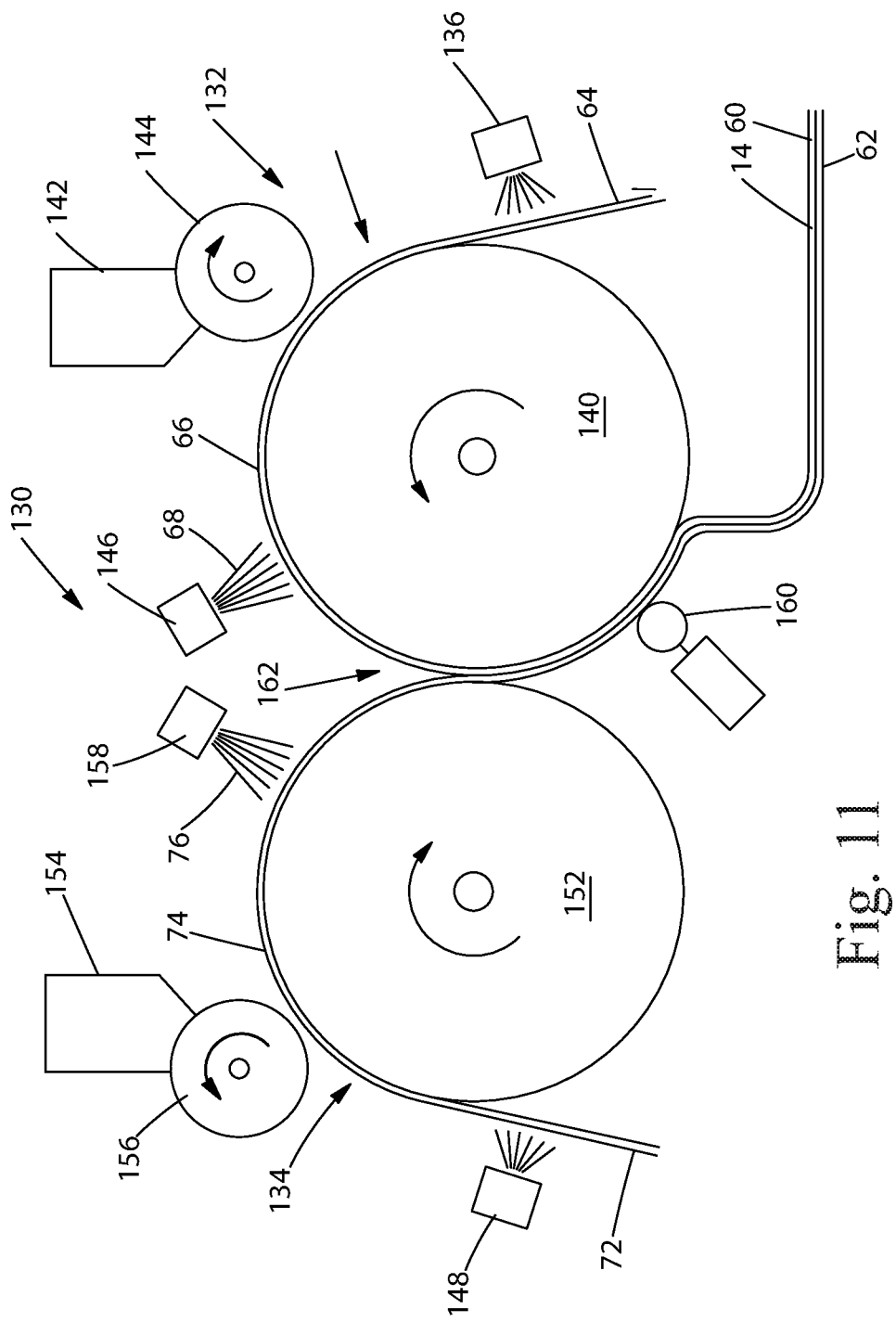
FIG. 11 is a schematic illustration of a process for making an absorbent core in accordance with an embodiment of the present invention.

A printing system 130 for making an absorbent core 14 in accordance with an embodiment of this invention is illustrated in FIG. 11 and may generally comprise a first printing unit 132 for forming the first absorbent layer 60 of the absorbent core 14 and a second printing unit 134 for forming the second absorbent layer 62 of the absorbent core 14.

The first printing unit 132 may comprise a first auxiliary adhesive applicator 136 for applying an auxiliary adhesive to the substrate 64, which may be a nonwoven web, a first rotatable support roll 140 for receiving the substrate 64, a hopper 142 for holding absorbent particulate polymer material 66, a printing roll 144 for transferring the absorbent particulate polymer material 66 to the substrate 64, and a thermoplastic composition material applicator 146 for applying the thermoplastic composition material 68 to the substrate 64 and the absorbent particulate polymer 66 material thereon.

The second printing unit 134 may comprise a second auxiliary adhesive applicator 148 for applying an auxiliary adhesive to the second substrate 72, a second rotatable support roll 152 for receiving the second substrate 72, a second hopper 154 for holding the absorbent particulate polymer material 74, a second printing roll 156 for transferring the absorbent particulate polymer material 74 from the hopper 154 to the second substrate 72, and a second thermoplastic composition material applicator 158 for applying the thermoplastic composition material 76 to the second substrate 72 and the absorbent particulate polymer material 74 thereon.

The printing system 130 also includes a guide roller 160 for guiding the formed absorbent core from a nip 162 between the first and second rotatable support rolls 140 and 152.

The first and second auxiliary applicators 136 and 148 and the first and second thermoplastic composition material applicators 146 and 158 may be a nozzle system which can provide a relatively thin but wide curtain of thermoplastic composition material. In some embodiments, a contact application such as a slot gun may be used, while other embodiments may be contactless (spray glue) applications. In some cases, only one of the auxiliary applicators 136 and 148 may be switched on, while in other cases both may be on at the same time, depending on the adhesive design.

As illustrated in FIGS. 1-8, the absorbent particulate polymer material 66 and 74 is deposited on the respective substrates 64 and 72 of the first and second absorbent layers 60 and 62 in clusters 90 of particles to form a grid pattern 92 comprising land areas 94 and junction areas 96 between the land areas 94. As defined herein, land areas 94 are areas where the fiberized net structure does not contact the nonwoven substrate or the auxiliary adhesive directly; junction areas 96 are areas where the thermoplastic adhesive material does contact the nonwoven substrate or the auxiliary adhesive (discussed below) directly; junction areas 96 are areas where the fiberized net structure does contact the nonwoven substrate or the auxiliary adhesive directly. The junction areas 96 in the grid pattern 92 contain little or no absorbent particulate polymer material 66 and 74. The land areas 94 and junction areas 96 can have a variety of shapes including, but not limited to, circular, oval, square, rectangular, triangular, and the like.

The grid pattern shown in FIG. 8 is a square grid with regular spacing and size of the land areas. Other grid patterns including hexagonal, rhombic, orthorhombic, parallelogram, triangular, rectangular, and combinations thereof may also be used. The spacing between the grid lines may be regular or irregular.

The size of the land areas 94 in the grid patterns 92 may vary. According to certain embodiments, the width 119 of the land areas 94 in the grid patterns 92 ranges from about 8 mm to about 12 mm. In a certain embodiment, the width of the land areas 94 is about 10 mm. The junction areas 96, on the other hand, in certain embodiments, have a width or larger span of less than about 5 mm, less than about 3 mm, less than about 2 mm, less than about 1.5 mm, less than about 1 mm, or less than about 0.5 mm.

As shown in FIG. 8, the absorbent core 14 has a longitudinal axis 100 extending from a rear end 102 to a front end 104 and a transverse axis 106 perpendicular to the longitudinal axis 100 extending from a first edge 108 to a second edge 110. The grid pattern 92 of absorbent particulate polymer material clusters 90 is arranged on the substrates 64 and 72 of the respective absorbent layers 60 and 62 such that the grid pattern 92 formed by the arrangement of land areas 94 and junction areas 96 forms a pattern angle 112. The pattern angle 112 may be 0, greater than 0, or 15 to 30 degrees, or from about 5 to about 85 degrees, or from about 10 to about 60 degrees, or from about 15 to about 30 degrees.

Figure 7A:
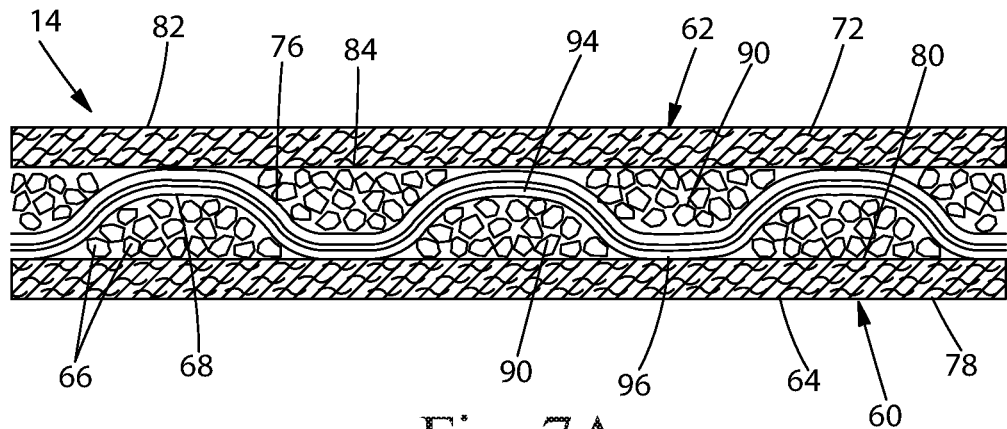
FIG. 7a is a partial sectional view of an absorbent core comprising a combination of the first and second absorbent core layers illustrated in FIGS. 5 and 6.
Figure 7B:
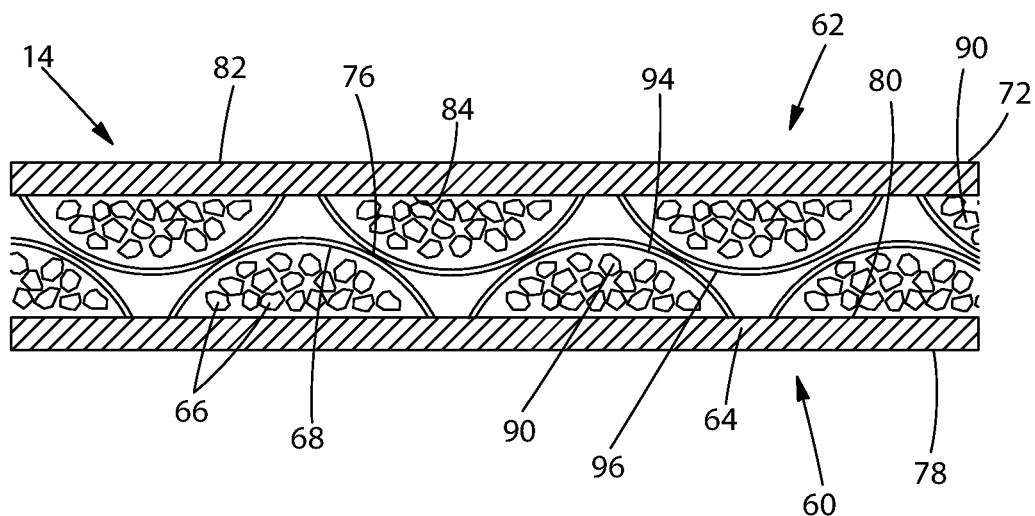
FIG. 7b is a partial sectional view of an absorbent core comprising a combination of the first and second absorbent core layers illustrated in FIGS. 5 and 6.

As best seen in FIGS. 7a, 7b, and 8, the first and second layers 60 and 62 may be combined to form the absorbent core 14. The absorbent core 14 has an absorbent particulate polymer material area 114 bounded by a pattern length 116 and a pattern width 118. The extent and shape of the absorbent particulate polymer material area 114 may vary depending on the desired application of the absorbent core 14 and the particular absorbent article in which it may be incorporated. In a certain embodiment, however, the absorbent particulate polymer material area 114 extends substantially entirely across the absorbent core 14, such as is illustrated in FIG. 8.

The first and second absorbent layers 60 and 62 may be combined together to form the absorbent core 14 such that the grid patterns 92 of the respective first and second absorbent layers 62 and 64 are offset from one another along the length and/or width of the absorbent core 14. The respective grid patterns 92 may be offset such that the absorbent particulate polymer material 66 and 74 is substantially continuously distributed across the absorbent particulate polymer area 114. In a certain embodiment, absorbent particulate polymer material 66 and 74 is substantially continuously distributed across the absorbent particulate polymer material area 114 despite the individual grid patterns 92 comprising absorbent particulate polymer material 66 and 74 discontinuously distributed across the first and second substrates 64 and 72 in clusters 90. In a certain embodiment, the grid patterns may be offset such that the land areas 94 of the first absorbent layer 60 face the junction areas 96 of the second absorbent layer 62 and the land areas of the second absorbent layer 62 face the junction areas 96 of the first absorbent layer 60. When the land areas 94 and junction areas 96 are appropriately sized and arranged, the resulting combination of absorbent particulate polymer material 66 and 74 is a substantially continuous layer of absorbent particular polymer material across the absorbent particulate polymer material area 114 of the absorbent core 14 (i.e. first and second substrates 64 and 72 do not form a plurality of pockets, each containing a cluster 90 of absorbent particulate polymer material 66 therebetween). In a certain embodiment, respective grid patterns 92 of the first and second absorbent layer 60 and 62 may be substantially the same.

In a certain embodiment as illustrated in FIG. 8, the amount of absorbent particulate polymer material 66 and 74 may vary along the length 116 of the grid pattern 92. In a certain embodiment, the grid pattern may be divided into absorbent zones 120, 122, 124, and 126, in which the amount of absorbent particulate polymer material 66 and 74 varies from zone to zone. As used herein, "absorbent zone" refers to a region of the absorbent particulate polymer material area having boundaries that are perpendicular to the longitudinal axis shown in FIG. 8. The amount of absorbent particulate polymer material 66 and 74 may, in a certain embodiment, gradually transition from one of the plurality of absorbent zones 120, 122, 124, and 126 to another. This gradual transition in amount of absorbent particulate polymer material 66 and 74 may reduce the possibility of cracks forming in the absorbent core 14.

The amount of absorbent particulate polymer material 66 and 74 present in the absorbent core 14 may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In a particular embodiment, the absorbent core 14 consists essentially of the first and second substrates 64 and 72, the absorbent particulate polymer material 66 and 74, and the thermoplastic composition 68 and 76. In an embodiment, the absorbent core 14 may be substantially cellulose free.

According to certain embodiments, the weight of absorbent particulate polymer material 66 and 74 in at least one freely selected first square measuring 1 cm×1 cm may be at least about 10%, or 20%, or 30%, 40% or 50% higher than the weight of absorbent particulate polymer material 66 and 74 in at least one freely selected second square measuring 1 cm×1 cm. In a certain embodiment, the first and the second square are centered about the longitudinal axis.

The absorbent particulate polymer material area, according to an exemplary embodiment, may have a relatively narrow width in the crotch area of the absorbent article for increased wearing comfort. Hence, the absorbent particulate polymer material area, according to an embodiment, may have a width as measured along a transverse line which is positioned at equal distance to the front edge and the rear edge of the absorbent article, which is less than about 100 mm, 90 mm, 80 mm, 70 mm, 60 mm or even less than about 50 mm.

It has been found that, for most absorbent articles such as diapers, the liquid discharge occurs predominately in the front half of the diaper. The front half of the absorbent core 14 should therefore comprise most of the absorbent capacity of the core. Thus, according to certain embodiments, the front half of said absorbent core 14 may comprise more than about 60% of the superabsorbent material, or more than about 65%, 70%, 75%, 80%, 85%, or 90% of the superabsorbent material. The absorbent core of the invention may comprise a core wrap enclosing the absorbent material. In some embodiments, the core wrap may be both the first and second substrates. The core wrap may be formed by two substrates, typically nonwoven material which may be at least partially sealed along the sides of the absorbent core. The first nonwoven may substantially form the top side of the core wrap and the second nonwoven substantially the bottom side of the core wrap. The core wrap may be at least partially sealed along its front side, back side and/or two longitudinal sides to improve the containment of the absorbent material during use. A C-wrap seal may be for example provided on the longitudinal sides of the core if improved containment is desired. Exemplary C-wrap description may be found in U.S. application Ser. No. 14/560,211. Typical core wraps comprise two substrates which are attached to one another, but the core wrap may also be made of a single substrate folded around the absorbent material, or may comprises several substrates. When two substrates are used, these may be typically attached to another along at least part of the periphery of the absorbent core to form a seal. Typically neither first nor second substrates need to be shaped, so that they can be rectangularly cut for ease of production but other shapes are not excluded.

The substrates are advantageously attached to another to form a seal along all the edges of the core. Typical seals are the so-called C-wrap and sandwich wrap. In a C-wrap, one of the substrate, e.g. the first substrate, has flaps extending over the opposed edges of the core which are then folded over the other substrate. These flaps are bonded to the external surface of the other substrate, typically by adhesive. This so called C-wrap construction can provide benefits such as improved resistance to bursting in a wet loaded state compared to a sandwich seal.

The front side and back side of the core wrap may then also be sealed for example by adhering the first substrate and second substrate to another to provide complete enclosing of the absorbent material across the whole of the periphery of the core. For the front side and back side of the core, the first and second substrate may extend and be joined together in a substantially planar direction, forming a so-called sandwich construction. In the so-called sandwich seal construction, the first and second substrates both have material extension outwardly of the absorbent material deposition area which are then sealed flat along the whole or parts of the periphery of the core typically by gluing and/or heat/pressure bonding.

The terms "seal" and "enclosing" are to be understood in a broad sense. The seal does not need to be continuous along the whole periphery of the core wrap but may be discontinuous along part or the whole of it, such as formed by a series of seal points spaced on a line. Typically a seal may be formed by gluing and/or thermal bonding. The core wrap may also be formed by a single substrate which may enclose the absorbent material as in a parcel wrap and be for example sealed along the front side and back side of the core and one longitudinally extending seal.

The core wrap may be formed by any materials suitable for enclosing the absorbent material. Typical substrate materials used in the production of conventional cores may be used, in particular nonwovens but also paper, tissues, films, wovens, or laminate of any of these. The core wrap may in particular be formed by a nonwoven web, such as a carded nonwoven, a spunbond nonwoven ("S") or a meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US2011/0268932A1, US2011/0319848A1, or US2011/0250413A1. Nonwoven materials provided from synthetic fibers may be used, such as polyethylene, Polyethylene terephthalate, and in particular polypropylene.

In certain embodiments, the absorbent core 14 may further comprise any absorbent material that is generally compressible, conformable, non-irritating to the wearer's skin, and capable of absorbing and retaining liquids such as urine and other certain body exudates. In such embodiments, the absorbent core 14 may comprise a wide variety of liquid-absorbent materials commonly used in disposable diapers and other absorbent articles such as comminuted wood pulp, which is generally referred to as airfelt, creped cellulose wadding, melt blown polymers, including co-form, chemically stiffened, modified or cross-linked cellulosic fibers, tissue, including tissue wraps and tissue laminates, absorbent foams, absorbent sponges, or any other known absorbent material or combinations of materials. The absorbent core 14 may further comprise minor amounts (typically less than about 10%) of materials, such as adhesives, waxes, oils and the like.

Exemplary absorbent structures for use as the absorbent assemblies are described in U.S. Pat. No. 4,610,678 (Weisman et al.); U.S. Pat. No. 4,834,735 (Alemany et al.); U.S. Pat. No. 4,888,231 (Angstadt); U.S. Pat. No. 5,260,345 (DesMarais et al.); U.S. Pat. No. 5,387,207 (Dyer et al.); U.S. Pat. No. 5,397,316 (LaVon et al.); and U.S. Pat. No. 5,625,222 (DesMarais et al.).

The absorbent article may further comprise at least one wetness indicator which is visible from the exterior of the article and which changes appearance when contacted with a body exudates, in particular urine. The wetness indicator (not shown) may be placed, when seen from the exterior of the article, between the two channel-forming areas 226 of FIG. 9, and/or between any of the channel-forming areas 226 and any of the lateral edge or both. The wetness indicators of the present invention may be according to any wetness indicating system known in the art. It is known that wetness indicator can provide an appearing signal, a disappearing signal or a color change signal, and combinations thereof. The wetness indicator may advantageously provide a color change signal, which may be typically obtained by a composition having a first color when dry and a second color different form the first color when wet, both colors being discernible by an external observer considering the article in a dry and a wet state.

The wetness indicator may in particular be a color change composition comprising a suitable pH indicator or another chemical substance that changes color when contacted with urine. Such compositions are for example disclosed in WO03/070138A2 or US2012/165771 (Ruman). More generally, the wetness indicator compositions of the invention may be as disclosed in WO2010/120705 (Klofta), comprising a colorant, a matrix and a stabilizer. The color change composition may be a hot-melt adhesive, which allows for an easy application of the composition on a substrate component of the article for example by a slot coating process or printed adhesive coating as disclosed e.g. in US2011274834 (Brown). The wetness indicator composition may be applied on any layer of the absorbent article using a conventional technique, for example printing, spraying or coating, during the making of the absorbent article. The layer may advantageously be the inner surface of the backsheet or the outer surface of the bottom side of the core wrap. This allows the wetness indicator to be visible from the exterior of the article by transparency through the backsheet while keeping the wetness indicator composition within the article. The wetness indicator may in particular be easily applied on a layer such a nonwoven or film by a slot-coating process especially if the composition is can be applied as a hot-melt.

Absorbent Material

The absorbent layer 217 comprises absorbent material 250, 66, and 74, that comprises superabsorbent polymer material (e.g. particles), optionally combined with cellulosic material (including for example cellulose, comminuted wood pulp in the form of fibers). The further material described above (e.g. a further, second absorbent structure (not represented) may include an absorbent material, and the following may apply thereto too.

In some embodiment, the absorbent material 250 may comprise at least 60%, or at least 70% by weight of superabsorbent polymer material, and at the most 40% or at the most 30% of cellulosic material.

In some other embodiments, the absorbent layer 217 comprises absorbent material 250 that consists substantially of absorbent polymer material, e.g. particles, e.g. less than 5% by weight (of the absorbent material 250) of cellulosic material is present; and said absorbent layer 217/absorbent structure 213, may be free of cellulosic material.

Typically, the superabsorbent polymer material is in the form of particles. Suitable for use in the absorbent layer 217 can comprise any superabsorbent polymer particles known from superabsorbent literature, for example such as described in Modern Superabsorbent Polymer Technology, F. L. Buchholz, A. T. Graham, Wiley 1998. The absorbent polymer particles may be spherical, spherical-like or irregular shaped particles, such as Vienna-sausage shaped particles, or ellipsoid shaped particles of the kind typically obtained from inverse phase suspension polymerizations. The particles can also be optionally agglomerated at least to some extent to form larger irregular particles.

In some embodiments herein, the absorbent material 250 as a whole and/or said particulate superabsorbent polymer material at least, has a high sorption capacity, e.g. having a CRC of for example at least 20 g/g, or at 30 g/g. Upper limits may for example be up to 150 g/g, or up to 100 g/g.

In some embodiments herein, the absorbent material 250 comprising or consisting of superabsorbent polymer particles that are formed from polyacrylic acid polymers/polyacrylate polymers, for example having a neutralization degree of from 60% to 90%, or about 75%, having for example sodium counter ions.

The superabsorbent polymer may be polyacrylates and polyacrylic acid polymers that are internally and/or surface cross-linked. Suitable material are described in the PCT Patent Application WO 07/047598 or for example WO 07/046052 or for example WO2009/155265 and WO2009/155264. In some embodiments, suitable superabsorbent polymer particles may be obtained by current state of the art production processes as is more particularly as described in WO 2006/083584. The superabsorbent polymers may be internally cross-linked, i.e. the polymerization is carried out in the presence of compounds having two or more polymerizable groups which can be free-radically copolymerized into the polymer network. Useful crosslinkers include for example ethylene glycol dimethacrylate, diethylene glycol diacrylate, allyl methacrylate, trimethylolpropane triacrylate, triallylamine, tetraallyloxyethane as described in EP-A 530 438, di- and triacrylates as described in EP-A 547 847, EP-A 559 476, EP-A 632 068, WO 93/21237, WO 03/104299, WO 03/104300, WO 03/104301 and in DE-A 103 31 450, mixed acrylates which, as well as acrylate groups, include further ethylenically unsaturated groups, as described in DE-A 103 31 456 and DE-A 103 55 401, or crosslinker mixtures as described for example in DE-A 195 43 368, DE-A 196 46 484, WO 90/15830 and WO 02/32962 as well as cross-linkers described in WO2009/155265. The superabsorbent polymer particles may be externally surface cross-linked, or: post cross-linked). Useful post-crosslinkers include compounds including two or more groups capable of forming covalent bonds with the carboxylate groups of the polymers. Useful compounds include for example alkoxysilyl compounds, polyaziridines, polyamines, polyamidoamines, di- or polyglycidyl compounds as described in EP-A 083 022, EP-A 543 303 and EP-A 937 736, polyhydric alcohols as described in DE-C 33 14 019, cyclic carbonates as described in DE-A 40 20 780, 2-oxazolidone and its derivatives, such as N-(2-hydroxyethyl)-2-oxazolidone as described in DE-A 198 07 502, bis- and poly-2-oxazolidones as described in DE-A 198 07 992, 2-oxotetrahydro-1,3-oxazine and its derivatives as described in DE-A 198 54 573, N-acyl-2-oxazolidones as described in DE-A 198 54 574, cyclic ureas as described in DE-A 102 04 937, bicyclic amide acetals as described in DE-A 103 34 584, oxetane and cyclic ureas as described in EP-A 1 199 327 and morpholine-2,3-dione and its derivatives as described in WO 03/031482.

The superabsorbent polymers or particles thereof may have surface modifications, such as being coated or partially coated with a coating agent. Examples of coated absorbent polymer particles are disclosed in WO2009/155265. The coating agent may be such that it renders the absorbent polymer particles more hydrophilic. For example, it may be hydrophilic (for example, fumed) silica, such as Aerosils. The coating agent may be a polymer, such as an elastic polymer or a film-forming polymer or an elastic film-forming polymer, which forms an elastomeric (elastic) film coating on the particle. The coating may be a homogeneous and/or uniform coating on the surface of the absorbent polymer particles. The coating agent may be applied at a level of from 0.1% to 5%.

The superabsorbent polymer particles may have a particle sizes in the range from 45 μm to 4000 μm, more specifically a particle size distribution within the range of from 45 μm to about 2000 μm, or from about 100 μm to about 1000 or to 850 μm. The particle size distribution of a material in particulate form can be determined as it is known in the art, for example by means of dry sieve analysis (EDANA 420.02 "Particle Size distribution).

In some embodiments herein, the superabsorbent material is in the form of particles with a mass medium particle size up to 2 mm, or between 50 microns and 2 mm or to 1 mm, or from 100 or 200 or 300 or 400 or 500 μm, or to 1000 or to 800 or to 700 μm; as can for example be measured by the method set out in for example EP-A-0691133. In some embodiments of the disclosure, the superabsorbent polymer material is in the form of particles whereof at least 80% by weight are particles of a size between 50 μm and 1200 μm and having a mass median particle size between any of the range combinations above. In addition, or in another embodiment of the disclosure, said particles are essentially spherical. In yet another or additional embodiment of the disclosure the superabsorbent polymer material has a relatively narrow range of particle sizes, e.g. with the majority (e.g. at least 80%, at least 90% or even at least 95% by weight) of particles having a particle size between 50 μm and 1000 μm, between 100 μm and 800 μm, between 200 μm and 600 μm.

Article

FIG. 1 is a plan view of an article, such as a diaper, 10 according to a certain embodiment of the present invention. The diaper 10 is shown in its flat out, uncontracted state (i.e., without elastic induced contraction) and portions of the diaper 10 are cut away to more clearly show the underlying structure of the diaper 10. A portion of the diaper 10 that contacts a wearer is facing the viewer in FIG. 1. The diaper 10 generally may comprise a chassis 12 and an absorbent core 14 disposed in the chassis.

The chassis 12 of the diaper 10 in FIG. 1 may comprise the main body of the diaper 10. The chassis 12 may comprise an outer covering 16 including a topsheet 18, which may be liquid pervious, and/or a backsheet 20, which may be liquid impervious. The absorbent core 14 may be encased between the topsheet 18 and the backsheet 20. The chassis 12 may also include side panels 22, elasticized leg cuffs 24, and an elastic waist feature 26.

The leg cuffs 24 and the elastic waist feature 26 may each typically comprise elastic members 28. One end portion of the diaper 10 may be configured as a first waist region 30 of the diaper 10. An opposite end portion of the diaper 10 may be configured as a second waist region 32 of the diaper 10. An intermediate portion of the diaper 10 may be configured as a crotch region 34, which extends longitudinally between the first and second waist regions 30 and 32. The waist regions 30 and 32 may include elastic elements such that they gather about the waist of the wearer to provide improved fit and containment (elastic waist feature 26). The crotch region 34 is that portion of the diaper 10 which, when the diaper 10 is worn, is generally positioned between the wearer's legs.

The diaper 10 is depicted in FIG. 1 with its longitudinal axis 36 and its transverse axis 38. The periphery 40 of the diaper 10 is defined by the outer edges of the diaper 10 in which the longitudinal edges 42 run generally parallel to the longitudinal axis 36 of the diaper 10 and the end edges 44 run between the longitudinal edges 42 generally parallel to the transverse axis 38 of the diaper 10. The chassis 12 may also comprise a fastening system, which may include at least one fastening member 46 and at least one stored landing zone 48.

The diaper 10 may also include such other features as are known in the art including front and rear ear panels, waist cap features, elastics and the like to provide better fit, containment and aesthetic characteristics. Such additional features are well known in the art and are e.g., described in U.S. Pat. Nos. 3,860,003 and 5,151,092.

In order to keep the diaper 10 in place about the wearer, at least a portion of the first waist region 30 may be attached by the fastening member 46 to at least a portion of the second waist region 32 to form leg opening(s) and an article waist. When fastened, the fastening system carries a tensile load around the article waist. The fastening system may allow an article user to hold one element of the fastening system, such as the fastening member 46, and connect the first waist region 30 to the second waist region 32 in at least two places. This may be achieved through manipulation of bond strengths between the fastening device elements.

According to certain embodiments, the diaper 10 may be provided with a re-closable fastening system or may alternatively be provided in the form of a pant-type diaper. When the absorbent article is a diaper, it may comprise a re-closable fastening system joined to the chassis for securing the diaper to a wearer. When the absorbent article is a pant-type diaper, the article may comprise at least two side panels joined to the chassis and to each other to form a pant. The fastening system and any component thereof may include any material suitable for such a use, including but not limited to plastics, films, foams, nonwoven, woven, paper, laminates, fiber reinforced plastics and the like, or combinations thereof. In certain embodiments, the materials making up the fastening device may be flexible. The flexibility may allow the fastening system to conform to the shape of the body and thus, reduce the likelihood that the fastening system will irritate or injure the wearer's skin.

For unitary absorbent articles, the chassis 12 and absorbent core 14 may form the main structure of the diaper 10 with other features added to form the composite diaper structure. While the topsheet 18, the backsheet 20, and the absorbent core 14 may be assembled in a variety of well-known configurations, preferred diaper configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 18 in FIG. 1 may be fully or partially elasticized or may be foreshortened to provide a void space between the topsheet 18 and the absorbent core 14. Exemplary structures including elasticized or foreshortened topsheets are described in more detail in U.S. Pat. Nos. 5,037,416 and 5,269,775.

The topsheet may be compliant, soft feeling, and non-irritating to the wearer's skin and may be elastically stretchable in one or more directions. Further, the topsheet may be liquid pervious, permitting liquids (e.g., menses, urine, and/or runny feces) to penetrate through its thickness. Various topsheets may also comprise a hydrophilic material, for example, which is configured to draw bodily fluids into an absorbent core of the chassis when these fluids are expelled from the body. A suitable topsheet may be manufactured from a wide range of materials, such as woven and nonwoven materials, apertured or hydroformed thermoplastic films, apertured nonwovens, porous foams, reticulated foams, reticulated thermoplastic films, and/or thermoplastic scrims, for example. Suitable apertured films may comprise those described in U.S. Pat. Nos. 3,929,135, 4,324,246, 4,342,314, 4,463,045, 5,006,394, 5,628,097, 5,916,661, 6,545,197, and 6,107,539.

Apertured film or nonwoven topsheets typically may be pervious to bodily exudates, yet non-absorbent, and have a reduced tendency to allow fluids to pass back through and rewet the wearer's skin. Suitable woven and nonwoven materials may comprise natural fibers, such as, for example, wood or cotton fibers, synthetic fibers, such as, for example, polyester, polypropylene, or polyethylene fibers, or combinations thereof. If the topsheet comprises fibers, the fibers may be spunbond, carded, wet-laid, meltblown, hydroentangled, or otherwise processed, for example, as is generally known in the art.

The topsheet may comprise a skin care lotion. Examples of suitable lotions include, but are not limited to, those described in U.S. Pat. Nos. 5,607,760; 5,609,587; 5,635,191; 5,643,588; and 5,968,025, and as described in U.S. Application No. 61/391,353, and as described in U.S. Pub. No. 2014-0257216. Beyond these compositions, the absorbent article may comprise soluble cyclodextrin derivatives such as those described in U.S. Pub. No. 2014/0274870.

Additionally, the topsheet of the present disclosure may be a tufted laminate web as disclosed in U.S. Pat. No. 7,410,683, and/or may be an apertured web as disclosed in PCT/CN2014/083769 having an international filing date of Aug. 6, 2014.

In one embodiment, the topsheet may comprise graphics such that depth perception is created as described in U.S. Pat. No. 7,163,528. In other embodiments, the topsheet may be an integrated acquisition layer and topsheet as described in U.S. Ser. No. 14/680,426 or Ser. No. 14/634,928.

In one embodiment, the absorbent article may comprise a backsheet. The backsheet may be impervious, or at least partially impervious, to fluids or body exudates (e.g., menses, urine, and/or runny feces) and may be manufactured from a thin plastic film, although other flexible liquid impervious materials may also be used. The backsheet may prevent the body exudates or fluids absorbed and contained in an absorbent core of the absorbent article from wetting articles which contact the absorbent article, such as bedsheets, pajamas, clothes, and/or undergarments. The backsheet may comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). A suitable backsheet may comprise a polyethylene film having a thickness of from about 0.012 mm (0.5 mils) to about 0.051 mm (2.0 mils). Examples of polyethylene films are manufactured by Clopay Corporation of Cincinnati, Ohio, under the designation BR-120 and BR-121, and by Tredegar Film Products of Terre Haute, Ind., under the designation XP-39385.

One suitable material for the backsheet can be a liquid impervious thermoplastic film having a thickness of from about 0.012 mm (0.50 mil) to about 0.051 mm (2.0 mils), for example including polyethylene or polypropylene. Typically, the backsheet can have a basis weight of from about 5 g/m2 to about 35 g/m2. The backsheet can be typically positioned adjacent the outer-facing surface of the absorbent core and can be joined thereto. For example, the backsheet may be secured to the absorbent core by a uniform continuous layer of adhesive, a patterned layer of adhesive, or an array of separate lines, spirals, or spots of adhesive. Illustrative, but non-limiting adhesives, include adhesives manufactured by H. B. Fuller Company of St. Paul, Minn., U.S.A., and marketed as HL-1358J. An example of a suitable attachment device including an open pattern network of filaments of adhesive is disclosed in U.S. Pat. No. 4,573,986. Another suitable attachment device including several lines of adhesive filaments swirled into a spiral pattern is illustrated by the apparatus and methods shown in U.S. Pat. Nos. 3,911,173; 4,785,996; and 4,842,666. Alternatively, the attachment device may include heat bonds, pressure bonds, ultrasonic bonds, dynamic mechanical bonds, or any other suitable attachment device or combinations of these attachment devices.

In one embodiment, the backsheet may be embossed and/or matte-finished to provide a more cloth-like appearance. Further, the backsheet may permit vapors to escape from the absorbent core of the absorbent article (i.e., the backsheet is breathable) while still preventing, or at least inhibiting, fluids or body exudates from passing through the backsheet. In one embodiment, the size of the backsheet may be dictated by the size of the absorbent article and the design or configuration of the absorbent article to be formed, for example.

The backsheet 20 may be joined with the topsheet 18. Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 10 while still preventing liquid exudates from passing through the backsheet 10. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont. Other breathable backsheets including nonwoven webs and apertured formed films are described in U.S. Pat. No. 5,571,096 issued to Dobrin et al. on Nov. 5, 1996.

In certain embodiments, the backsheet of the present invention may have a water vapor transmission rate (WVTR) of greater than about 2000 g/24 h/m$^2$, greater than about 3000 g/24 h/m$^2$, greater than about 5000 g/24 h/m$^2$, greater than about 6000 g/24 h/m$^2$, greater than about 7000 g/24 h/m$^2$, greater than about 8000 g/24 h/m$^2$, greater than about 9000 g/24 h/m$^2$, greater than about 10000 g/24 h/m$^2$, greater than about 11000 g/24 h/m$^2$, greater than about 12000 g/24 h/m$^2$, greater than about 15000 g/24 h/m$^2$, measured according to WSP 70.5 (08) at 37.8° C. and 60% Relative Humidity.

FIG. 2 shows a cross section of FIG. 1 taken along the sectional line 2-2 of FIG. 1. Starting from the wearer facing side, the diaper 10 may comprise the topsheet 18, the components of the absorbent core 14, and the backsheet 20. According to a certain embodiment, the diaper 10 may also comprise an acquisition system 50 disposed between the liquid permeable topsheet 18 and a wearer facing side of the absorbent core 14. The acquisition system 50 may be in direct contact with the absorbent core. The acquisition system 50 may comprise a single layer or multiple layers, such as an upper acquisition layer 52 facing towards the wearer's skin and a lower acquisition 54 layer facing the garment of the wearer. According to a certain embodiment, the acquisition system 50 may function to receive a surge of liquid, such as a gush of urine. In other words, the acquisition system 50 may serve as a temporary reservoir for liquid until the absorbent core 14 can absorb the liquid.

In a certain embodiment, the acquisition system 50 may comprise chemically cross-linked cellulosic fibers. Such cross-linked cellulosic fibers may have desirable absorbency properties. Exemplary chemically cross-linked cellulosic fibers are disclosed in U.S. Pat. No. 5,137,537. According to certain embodiments, the cross-linked cellulosic fibers may be crimped, twisted, or curled, or a combination thereof including crimped, twisted, and curled.

In a certain embodiment, one or both of the upper and lower acquisition layers 52 and 54 may comprise a nonwoven, which may be hydrophilic. Further, according to a certain embodiment, one or both of the upper and lower acquisition layers 52 and 54 may comprise the chemically cross-linked cellulosic fibers, which may or may not form part of a nonwoven material. According to an exemplary embodiment, the upper acquisition layer 52 may comprise a nonwoven, without the cross-linked cellulosic fibers, and the lower acquisition layer 54 may comprise the chemically cross-linked cellulosic fibers. Further, according to an embodiment, the lower acquisition layer 54 may comprise the chemically cross-linked cellulosic fibers mixed with other fibers such as natural or synthetic polymeric fibers. According to exemplary embodiments, such other natural or synthetic polymeric fibers may include high surface area fibers, thermoplastic binding fibers, polyethylene fibers, polypropylene fibers, PET fibers, rayon fibers, lyocell fibers, and mixtures thereof. According to a particular embodiment, the lower acquisition layer 54 has a total dry weight, the cross-linked cellulosic fibers are present on a dry weight basis in the upper acquisition layer in an amount from about 30% to about 95% by weight of the lower acquisition layer 54, and the other natural or synthetic polymeric fibers are present on a dry weight basis in the lower acquisition layer 54 in an amount from about 70% to about 5% by weight of the lower acquisition layer 54.

According to a certain embodiment, the lower acquisition layer 54 desirably has a high fluid uptake capability. Fluid uptake is measured in grams of absorbed fluid per gram of absorbent material and is expressed by the value of "maximum uptake." A high fluid uptake corresponds therefore to a high capacity of the material and is beneficial, because it ensures the complete acquisition of fluids to be absorbed by an acquisition material. According to exemplary embodiments, the lower acquisition layer 54 has a maximum uptake of about 10 g/g.

Suitable non-woven materials for the upper and lower acquisition layers 52 and 54 include, but are not limited to SMS material, comprising a spunbonded, a melt-blown and a further spunbonded layer. In certain embodiments, permanently hydrophilic non-wovens, and in particular, nonwovens with durably hydrophilic coatings are desirable. Additional suitable embodiments may in particular be formed by a nonwoven web, such as a carded nonwoven, a spunbond nonwoven ("S") or a meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US2011/0268932A1, US2011/0319848A1, or US2011/0250413A1. Nonwoven materials provided from synthetic fibers may be used, such as polyethylene, polyethylene terephthalate, and in particular polypropylene.

As polymers used for nonwoven production may be inherently hydrophobic, they may be coated with hydrophilic coatings. One way to produce nonwovens with durably hydrophilic coatings, is via applying a hydrophilic monomer and a radical polymerization initiator onto the nonwoven, and conducting a polymerization activated via UV light resulting in monomer chemically bound to the surface of the nonwoven as described in co-pending U.S. Patent Publication No. 2005/0159720. Another way to produce nonwovens with durably hydrophilic coatings is to coat the nonwoven with hydrophilic nanoparticles as described in co-pending applications U.S. Pat. No. 7,112,621 to Rohrbaugh et al. and in PCT Application Publication WO 02/064877.

Typically, nanoparticles have a largest dimension of below 750 nm. Nanoparticles with sizes ranging from 2 to 750 nm may be economically produced. An advantage of nanoparticles is that many of them can be easily dispersed in water solution to enable coating application onto the nonwoven, they typically form transparent coatings, and the coatings applied from water solutions are typically sufficiently durable to exposure to water. Nanoparticles can be organic or inorganic, synthetic or natural. Inorganic nanoparticles generally exist as oxides, silicates, and/or, carbonates. Typical examples of suitable nanoparticles are layered clay minerals (e.g., LAPONITE™ from Southern Clay Products, Inc. (USA), and Boehmite alumina (e.g., Disperal P2™ from North American Sasol. Inc.). According to a certain embodiment, a suitable nanoparticle coated nonwoven is that disclosed in patent application Ser. No. 10/758,066 entitled "Disposable absorbent article comprising a durable hydrophilic core wrap" to Ekaterina Anatolyevna Ponomarenko and Mattias NMN Schmidt.

Further useful non-wovens are described in U.S. Pat. No. 6,645,569 to Cramer et al., U.S. Pat. No. 6,863,933 to Cramer et al., U.S. Pat. No. 7,112,621 to Rohrbaugh et al., and co-pending patent application Ser. No. 10/338,603 to Cramer et al. and Ser. No. 10/338,610 to Cramer et al.

In some cases, the nonwoven surface can be pre-treated with high energy treatment (corona, plasma) prior to application of nanoparticle coatings. High energy pre-treatment typically temporarily increases the surface energy of a low surface energy surface (such as PP) and thus enables better wetting of a nonwoven by the nanoparticle dispersion in water.

Notably, permanently hydrophilic non-wovens are also useful in other parts of an absorbent article. For example, topsheets and absorbent core layers comprising permanently hydrophilic non-wovens as described above have been found to work well.

According to a certain embodiment, the upper acquisition layer 52 may comprise a material that provides good recovery when external pressure is applied and removed. Further, according to a certain embodiment, the upper acquisition layer 52 may comprise a blend of different fibers selected, for example from the types of polymeric fibers described above. In some embodiments, at least a portion of the fibers may exhibit a spiral-crimp which has a helical shape. In some embodiments, the upper acquisition layer 52 may comprise fibers having different degrees or types of crimping, or both. For example, one embodiment may include a mixture of fibers having about 8 to about 12 crimps per inch (cpi) or about 9 to about 10 cpi, and other fibers having about 4 to about 8 cpi or about 5 to about 7 cpi. Different types of crimps include, but are not limited to a 2D crimp or "flat crimp" and a 3D or spiral-crimp. According to a certain embodiment, the fibers may include bi-component fibers, which are individual fibers each comprising different materials, usually a first and a second polymeric material. It is believed that the use of side-by-side bi-component fibers is beneficial for imparting a spiral-crimp to the fibers.

The upper acquisition layer 52 may be stabilized by a latex binder, for example a styrene-butadiene latex binder (SB latex), in a certain embodiment. Processes for obtaining such lattices are known, for example, from EP 149 880 (Kwok) and US 2003/0105190 (Diehl et al.). In certain embodiments, the binder may be present in the upper acquisition layer 52 in excess of about 12%, about 14% or about 16% by weight. For certain embodiments, SB latex is available under the trade name GENFLO™ 3160 (OMNOVA Solutions Inc.; Akron, Ohio).

Channels

Figure 9:
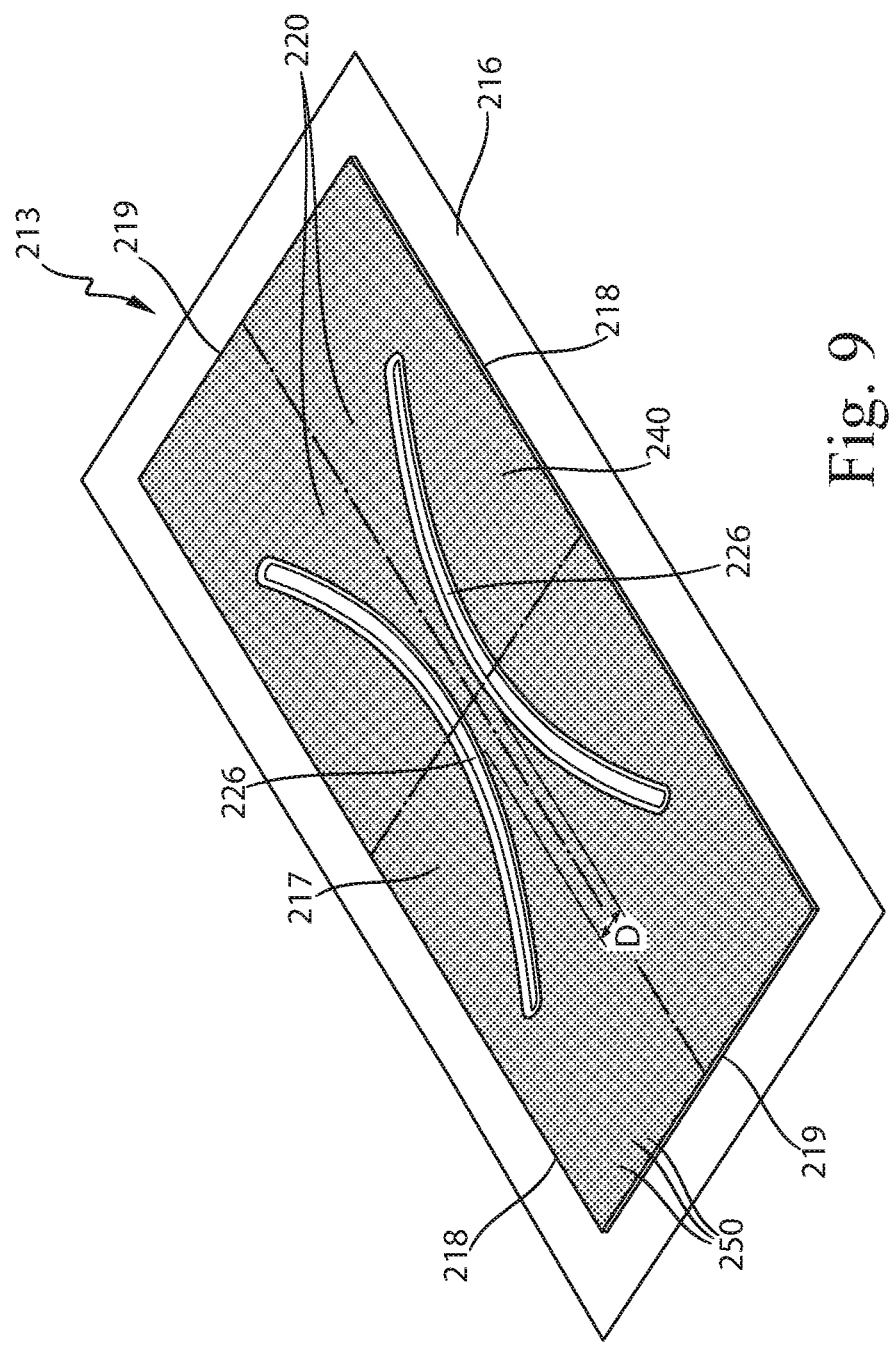
FIG. 9 shows a perspective view of an absorbent structure.

In some embodiments, the absorbent core may comprise channels, or areas substantially free of absorbent polymer particles or absorbent polymer material. The channels may provide improved liquid transport, and hence faster acquisition, and more efficient liquid absorbency over the whole absorbent structure, in addition to reducing the stiffness of partially or fully loaded cores. As shown in FIG. 9, the absorbent structure 213 comprises a first substrate (a supporting sheet) 216, and an absorbent layer 217 of absorbent material 250. The absorbent material 250 comprises at least a superabsorbent polymer material (absorbent particulate polymer material) and optionally a cellulosic material, such as a cellulose, e.g. pulp, or modified cellulose in a absorbent particulate polymer material area.

The absorbent structure 213 also comprises one or more thermoplastic compositions, as described above. The absorbent layer 217 is three dimensional and comprises a first substantially longitudinal channel 226 and a second substantially longitudinal channel 226 that are substantially free of said superabsorbent polymer material. Other materials may be present in said channels 226, as further described below, for example said one or more thermoplastic compositions and/or a fiberized net structure 240.

The absorbent structure 213 and the absorbent layer 217 each have a longitudinal dimension and average length L, e.g. extending in the longitudinal dimension of the structure or layer and a transverse dimension and average width W, e.g. extending in the transverse dimension of the structure or layer. The absorbent structure 213 and the absorbent layer 217 each have a front region, being in use towards the front of the user, back region, being in use towards the back of the user, and therein between a crotch region, each extending the full transverse width of the structure/layer, and each having ⅓ of the average length of the structure/layer.

The absorbent structure 213 and the absorbent layer 217 each have a pair of opposing longitudinal side edges 218 extending in the longitudinal dimension of the structure or layer and a pair of opposing transverse edges 219, e.g. front transverse edge being in use towards the front of a user (wearer), and a back transverse edge being in use towards the back of a user.

The absorbent layer 217 comprises at least a first channel 226 and second channel 226 that are substantially free of (e.g. free of) said superabsorbent polymer particles, said channels 226 extending through the thickness height of the absorbent layer 217. By "substantially free" it is meant that in each of these areas the basis weight of the absorbent material is at least less than 25%, in particular less than 20%, less than 10%, of the average basis weight of the absorbent material in the rest of the absorbent material deposition area of the core. In particular there can be no absorbent material in these areas 226. (It should be understood that, accidentally, a small, negligible amount of superabsorbent polymer particles may be present in the channel, which does not contribute to the overall functionality). When the absorbent layer 217 comprises cellulosic or cellulose, in some embodiments the said first and second channels 226 are also free of such cellulosic/cellulose material.

The first and second channel 226 each extend substantially longitudinally, which means typically that each channel 226 extends more in the longitudinal dimension than in the transverse dimension, and typically at least twice as much in the longitudinal dimension than in the transverse dimension.

Thus, this includes channels 226 that are completely longitudinal and parallel to the longitudinal direction of said absorbent layer 217; and this includes channels 226 that may curve, provided the radius of curvature is typically at least equal (optionally at least 1.5 or at least 2.0 times this average transverse dimension) to the average transverse dimension of the absorbent layer; and this includes channels 226 that are straight but under an angle of (e.g. from 5°) up to 30°, or for example up to 20°, or up to 10° with a line parallel to the longitudinal axis. In some embodiments, there may be no completely or substantially transverse channels present in at least said crotch region, or no such channels at all. Further descriptions of channels, including various dimensions and arrangements, are described in U.S. patent application Ser. Nos. 13/491,642, 13/491,643, 13/491,644, and 13/491,648.

The channels 226 may typically be so-called "permanent" channels 226. By permanent, it is meant that the integrity of the channels 226 is at least partially maintained both in the dry state and in the wet state, including during friction by the wearer thereon.

Figure 10:
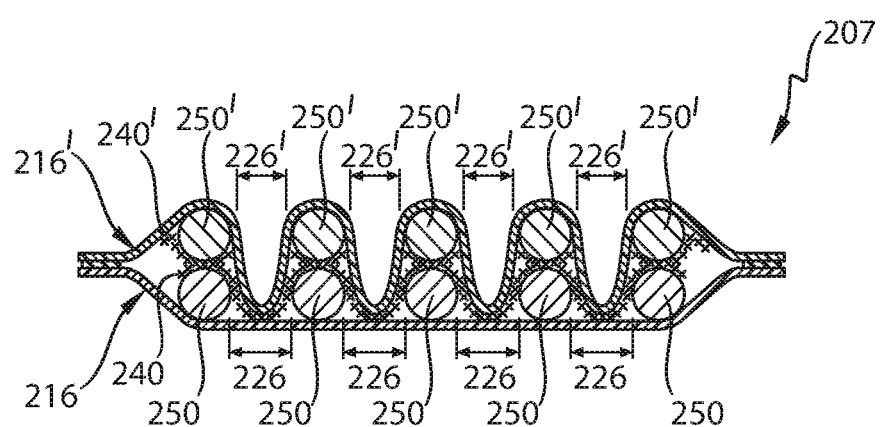
FIG. 10 shows a cross sectional view of an alternative absorbent core.

Permanent channels 226 may be obtained by provision of one or more thermoplastic compositions that immobilize said absorbent material 250, and/or said channels 226, e.g. or said absorbent layer 217, and/or that immobilize said supporting sheet 216 into said channels 226, or part thereof. As shown in FIG. 10, the absorbent core 207 may comprise in particular permanent channels formed by bonding of a first supporting sheet or first substrate 216 and a second supporting sheet or second substrate 216' through the channels. Typically, glue may be used to bond both supporting sheets throughout the channel, but it is possible to bond via other known means, for example ultrasonic bonding, or heat bonding. The supporting layers can be continuously bonded or intermittently bonded along the channels.

Such channels provide for fast liquid acquisition which reduces risk of leakages. The permanent channels help to avoid saturation of the absorbent layer in the region of fluid discharge (such saturation increases the risk of leakages). Furthermore, whilst decreasing the overall amount of superabsorbent polymer material in the absorbent structure is reduced (by providing channels free of such material), the fluid handling properties of the absorbent structure, or diaper, are improved. Permanent channels also have the further advantage that in the wet state the absorbent material is more restricted to move within the core and remains in its intended application area, thus providing better fit and fluid absorption. This can be demonstrated by comparing the amount of AGM loss in a wet state according to the WAIIT test for a core having two absorbent layers with permanent channels relative to a similar core with the same amount of AGM and glue but having no channels.

In short, the WAIIT test determines the amount of non-immobilized absorbent particulate material amount in the cores in wet conditions. Further information regarding the test can be found in US 2008/0312622 A1. A permanent channel according to the disclosure has a percentage of integrity of at least 20%, or 30%, or 40%, or 50%, or 60, or 70%, or 80%, or 90% following this test.

One or more thermoplastic composition(s) 240 (fiberized net structure and/or a hot melt adhesive) may be present between said supporting sheet 216 and said absorbent layer 217, or parts thereof. For example, an adhesive material may be applied to portions of said supporting sheet 216 that are to coincide with the channels 226, so that in said channels the supporting sheet can be bonded with said adhesive to the walls of the channel, or part thereof or to a further material; and/or the adhesive may be applied to portions of the supporting sheet 216 that are to coincide with the absorbent material 250, to immobilize said material and avoid extensive migration thereof into said channels; the adhesive may be applied over substantially the whole surface area of the supporting sheet 216, e.g. substantially continuously and/or homogeneously. This may for example be a thermoplastic hotmelt adhesive applied by printing, slot coating or spraying.

In addition, or alternatively, the absorbent structure may comprise one or more adhesive materials applied on said absorbent layer or part thereof, that is already supported by said supporting sheet, (herein referred to as "first adhesive material") e.g. after said absorbent material is combined with/deposited on said supporting sheet to form an absorbent layer. This may for example be a thermoplastic fibrous adhesive. In some embodiments, this may be applied continuously over the absorbent layer, hence over the absorbent material and in the channels, to immobilize the absorbent layer and to optionally also adhere the supporting sheet in said channel, as described above.

It should be understood that the first and second adhesive material may be the same or different type of adhesive, for example as a thermoplastic hotmelt adhesive.

In some embodiments, said one or more adhesive material are at least present in the channels, for example at least said first adhesive material, or both said first and second adhesive material. It may thus be present on the longitudinal walls of the channels (extending the height of the absorbent layer and the length thereof). If the supporting sheet material folds into said channels, or part thereof, e.g. the supporting sheet has undulations into said channels or part thereof, said undulations may be fixed to said walls or part thereof, to ensure the channels are maintained (at least partially) during use.

The absorbent structure may comprise two or more than two channels, for example at least 4, or at least 5 or at least 6. Some or all of these may be substantially parallel to one another, for example being all straight and completely longitudinally, and/or two or more or all may be mirror images of one another in the longitudinal axis, or two or more may be curved or angled and for example mirror images of one another in the longitudinal axis, and two or more may be differently curved or straight, and for example mirror images of one another in the longitudinal axis.

The absorbent structure typically comprises one or more further material(s) (e.g. a second substrate) to cover the absorbent layer, herein referred to as a second substrate; for the avoidance of any doubt, this is not a layer consisting of an adhesive material, however the second substrate may be a layer comprising adhesive, for example on the surface that is to contact the absorbent layer of the absorbent structure. Thus, the second substrate may comprise on the surface to be placed adjacent said absorbent layer of the absorbent structure, an adhesive material. The resulting structure is herein referred to as "absorbent core 207".

This second substrate may be a further absorbent structure, with a second absorbent layer and a second supporting sheet 216', so that both absorbent layers are sandwiched between said supporting sheets 216; 216'. The second absorbent structure may be identical to the first absorbent structure, or they may both be absorbent structure with channels 226; 226', but they may be different, for example having different channels, different number of channels, different adhesive, different adhesive application or combinations thereof.

In some embodiments, the second substrate may be a part of the supporting sheet 216, which is folded over the absorbent layer 217 and then sealed along the peripheral edges, to enclose the absorbent layer 217.

In some embodiments, the further substrate is a further supporting sheet, i.e. the absorbent structure 213 is covered with a further supporting sheet 216', said absorbent layer then being sandwiched between the two supporting sheets.

The supporting sheet of the first structure and/or the second supporting sheet of the acquisition material layer may fold into the channels of the first absorbent structure and/or optionally into the channels of the acquisition material layer, if present, or part of these channels. The one or more adhesive material(s) may be at least present in the channels, or part thereof, and the supporting sheets may be adhered to one another in said channels by one or more of these adhesive material(s). Another second adhesive may be present between the second supporting sheet and the acquisition material layer. Another adhesive (not represented) may be placed between the acquisition material layer and the absorbent layer, in addition to the thermoplastic composition 240, to improve better adhesion of both layers.

In any of these cases, the second substrate can then be sealed to the supporting sheet along the peripheral edges thereof, to enclose the absorbent layer(s).

In any of these cases the supporting sheet or acquisition layer/sheet may fold into (i.e. undulate into) said channels or part thereof, as shown in FIG. 10.

It may be adhered to the supporting sheet of the absorbent structure of the disclosure in said channels, e.g. by an adhesive material, as described herein, ie., the substrate 216 (nonwoven dusting layer or second substrate) may be laminated to substrate 216' (core cover or first substrate) or visa versa. Alternatively, or in addition, it may be adhered to the walls of the channels or part thereof.

In some embodiments the absorbent structure comprises such a further material overlaying said absorbent layer, and a pressure means is applied selectively to said supporting sheet and/or to said further material, in those parts that coincide with said channels, to pressurize said supporting sheet and/or said further material into said channels of the absorbent structure and/or into the channels of a further (second) absorbent structure if present, to aid formulation of said undulations and/or to aid adhering of the further material and said supporting sheet to one another in said channel, if an adhesive material is present as described herein.

Further various embodiments of channels in an absorbent structure or core may be found in U.S. Ser. No. 13/491,642. Processes for making absorbent cores with channels may be such as those described in U.S. Ser. Nos. 14/615,467 and 14/615,456.

In one of the embodiment herein, the supporting sheet 216 has undulations that fold (undulate) into said first and second channels 226, and optionally in to said further channel(s), of part thereof. For example the undulations may extend over about the full longitudinal dimension of the channel; they may for example extend to complete average height of the absorbent layer 217/channel, or for example only up to 75% thereof, or up to 50% of the average height of the absorbent layer 217/channel. This aids immobilization of the absorbent material 250 adjacent said channels 226 and said channels 226 of said layers.

The undulations may be adhered with said one or more adhesive material, e.g. said second adhesive material, to said walls of said channels 226. The supporting sheet 216 may alternatively, or in addition, be adhered in said channels 226 to said further material, e.g. second supporting sheet 216, describe herein above, e.g. with said first and/or second adhesive.

The absorbent structure may comprise one or more adhesive material. In some embodiments, it comprises a first adhesive material and/or a second adhesive material, as described above, and in the manner described above.

The absorbent core herein may comprise a further second absorbent structure that may comprise one or more adhesive materials.

Storage Modulus (G')

Absorbent structures of the present invention comprise adhesives and/or fiberized net structures that have relatively high G' values.

An exemplary thermoplastic composition 68 and 76 may have a storage modulus G' measured at 21° C. of at least about $1.2 \times 10^6$ Pa as measured by the test method detailed below. It is unexpected that the thermoplastic compositions of the present invention have high G' values but are not too stiff to work as a fiberized net structure or a hot melt adhesive in absorbent articles. An adhesive with a relatively high G', such as greater than $1.2 \times 10^6$ Pa, means a stiffer adhesive. The thermoplastic compositions in the present invention may be less dense, thus providing more volume at the same basis weight. This is particularly true for compositions comprising polyolefins.

The fiberized net structure may consist of continuous extruded polymer/adhesive strands, which create a net structure with irregular strand or filament thickness or with irregular open areas (pores or maximum strand to strand distance). Continuous polymer/adhesive strands may overlap and form strand crossings or overlaps with different diameters. The applied fiberized net structure may build a three-dimensional net in the absorbent core as described herein. At equivalent basis weights, a fiberized net structure with thicker fibers may be more open and irregular than a fiberized net structure with thinner fibers. It is believed that the thicker fibers can maintain heat in the fiber longer, which can allow the fiberized net structure to wet and penetrate a nonwoven better, allowing for bond strength. If, for example, the core has channels and the channels are more secure, that is, are permanent channels, the more open structure of the fiberized net structure allows the AGM or superabsorbent polymer material to adjust or move within its confined area.

In Table 1, Storage Modulus G' at 21° C. is reflected to describe the thermoplastic hotmelt properties of core adhesives or fiberized net structures at lab measurement conditions of T=21° C. for PO1, PO2, PO5, and PO3 as described in table 2, as well as for PO4 and PO6, which are polyolefin-based materials, as described herein. Storage Modulus G' at 35° C. is reflected to describe the thermoplastic hotmelt properties during hygiene product usage. And Storage Modulus G' at 60° C. and 90° C. are reflected to describe the thermoplastic hotmelt properties during hygiene product storage conditions, i.e. environment of global climate zones or transportation.

Thermoplastic compositions with a G' at 21° C. and 6.28 rad/s greater than about $1.2 \times 10^6$ Pa will likely have a high G' at higher temperatures, such as 60° C. and/or 90° C. up to the melting point. These high G' levels at higher temperatures present processing challenges in contact and/or contactless applications, i.e. slot coating, summit, curtain coater, spiral, omega, etc., due to, for example, higher viscosities. However, if these thermoplastic compositions, such as thermoplastic adhesive materials, properly wet and penetrate into the primary and secondary substrates, they can create mechanical bonding via a greater than 300° or even 360° flow around sufficient individual substrate fibers, and build up their final internal molecule structure and strength. They can yield strong bonds with exceptional bonding hang times.

The storage modulus measured at 60° C. and 90° C. may be a measure for the form stability of the thermoplastic adhesive material at elevated ambient temperatures. This value is particularly important if the absorbent product is used in a hot climate where the thermoplastic adhesive material would lose its integrity if the storage modulus G' at 60° C. and 90° C. is not sufficiently high.

TABLE 1

G', viscosity and ring & ball softening point data

| Glue Code | Tg in [° C.] | DMA G'@21° C. [Pa] (Frequency 6.28 rad/s) | DMA G'@35° C. [Pa] (Frequency 6.28 rad/s) | DMA G'@60° C. [Pa] (Frequency 6.28 rad/s) | DMA G'@90° C. [Pa] (Frequency 6.28 rad/s) | Viscosity @ T = 175° C. [mPas] | Viscosity @ [mPas], (spindel 27, 20 rpm; 20 min preheating, 10 min stirring) OR **Viscosity @ T = 150° C. [mPas], (spindel 27, 20 rpm; 20 min preheating, 10 min stirring) | Ring & Ball Softening point [° C.] |
|---|---|---|---|---|---|---|---|---|
| PO1 | 13 | $7.80 \times 10^6$ | $3.52 \times 10^6$ | $1.40 \times 10^6$ | $0.25 \times 10^6$ | 2,620 | 5000 | 109 |
| PO4 | N/A | N/A | N/A | N/A | N/A | 3,010 | 5700 | 109 |
| PO3 | 2 | $5.24 \times 10^6$ | $2.85 \times 10^6$ | $1.02 \times 10^6$ | $0.21 \times 10^6$ | 3,500 | 7000 ** | 81 |
| PO2 | 5 | $6.35 \times 10^6$ | $3.33 \times 10^6$ | $0.94 \times 10^6$ | $5 \times 10^3$ | 3,800 | 5500 | ~82 |
| PO5 | 6 | $3.63 \times 10^6$ | $1.86 \times 10^6$ | $0.55 \times 10^6$ | $1.41 \times 10^4$ | 4,600 | 6700 | ~84 |
| PO6 | N/A | N/A | N/A | N/A | N/A | 2,500 | 3800 ** | ~90 |

TABLE 2

| option | Unit | 1 | 2 | 3 | 4 | 5 | 6 | 7 |
|---|---|---|---|---|---|---|---|---|
| Fiberized net structure composition | | PO1 | PO1 | PO1 | PO1 | PO2 | PO5 | PO1 |
| Auxiliary adhesive | | PO1 | PO1 | PO1 | PO3 | PO2 | PO5 | PO1 |
| Total weight of fiberized net structure composition | [g/m$^2$] | 4/3 = 7 | 4/3 = 7 | 4/3 = 7 | 4/3 = 7 | 4/3 = 7 | 4/3 = 7 | 2/2 = 4 |
| First substrate/Second substrate | | | | | | | | |
| Total weight of fiberized net structure composition + auxiliary adhesive | [g/m$^2$] | 15 | 9 | 7 | 15 | 15 | 15 | 12 |
| Total weight of front or back end seal adhesive | [g/m$^2$] | 35 | 19 | 12 | 35 | 35 | 35 | 32 |
| Wet immobilization | | | | | | | | |
| Room temperature, initial | [%] | 27 | 27 | 25 | 29 | 50 | 51 | 27 |
| 60 C./6 hour aged | [%] | 35 | 32 | 34 | 30 | 31 | 48 | 41 |
| Core end seal hang times | | | | | | | | |
| Back end seal/Front end seal | | | | | | | | |
| Normalized initial core end seal hang time (initial~2 hrs after production at room temperature) | [min] | 1717/3327 >480 | 434/864 >60 | 25/138 <200 | 166/109 <200 | 1172/1172 >720 | 539/1162 >480 | 1526/1342 >720 |
| Normalized final core end seal hang time (Final −60 C./6 hour aged) | [min] | 1346*/1346* >480 | 770/421 >250 | 30/64 <100 | 215/157 <200 | 1315/1069 >720 | 1256/1256 >480 | 1285/1285 >720 |
| Normalized core end seal hang time at 50 C./2 weeks aged | [min] | 1020*/1020* >720 | 996/1002 >480 | N/A (not available) | 494/355 >250 | N/A | N/A | N/A |
| Channel hang times (2 channels; left/right) | [min] | | | | | | | |
| Normalized initial channel hang time (initial~2 hrs after production at room temperature) | [min] | 1449/1057 >480 | 1008/1321 >70 | 645/750 >70 | 294/306 <300 | 1020/1020 >480 | 1377/1377 >720 | 1738/1738 >720 |
| Normalized final channel hang time (final −60 C./6 hours aged) | [min] | 997*/997* >800 | 974*/974* >800 | 848/954 >500 | 482/583 <500 | 1119/1119 >800 | 1172/1172 >800 | 1199/1199 >1000 |
| Normalized channel hang time at 50 C./2 weeks aged | [min] | 1002/1002 >1000 | 1243/1377* >1000 | 1354/1409* >600 | 908/908 >600 | N/A | N/A | N/A |
| Wet normalized initial channel hang time | [min] | 1119*/1119* >1000 | N/A | 1082/857 >600 | 1136/628 >1000 | 952/952 >600 | 952/952 >900 | 941/941 >900 |

In table 2, absorbent cores or structures were made as described herein, using 10 gsm hydrophilic nonwoven core cover material (first substrate) and a 10 gsm hydrophobic nonwoven dusting layer (second substrate), and absorbent material as described herein. Core adhesives and/or fiberized net structures used may be a polyolefin-based material as described herein. It may be polypropylene-based, or NW1414 available from the H.B. Fuller Company (PO1), or a blend of polyolefin polymers compounded with one or more hydrocarbon tackifying resins and plasticizers (PO2 or PO5), or a material such as Henkel DM3800 (PO3). The table displays the wet immobilization of each core (initial and aged), the core end seal hang times, and channel hang times (dry and wet), using the test methods described herein.

The normalized initial core end seal hang time of the present invention may be at least about 60 minutes, in some cases at least about 480 minutes, at least about 600 minutes, or at least about 720 minutes. The normalized final core end seal hang time may be at least about 250 minutes, in some cases at least about 480 minutes, or at least about 720 minutes. The normalized initial channel hang time may be at least about 70 minutes, in some cases at least about 480 minutes, or at least about 720 minutes. The normalized final channel hang time may be at least about 800 minutes, in some case at least about 1000 minutes. A channel hang time of at least about 480 minutes may be considered a permanent channel bond.

Test Methods

1. Bonded Nonwovens Hang Time (Core End Seal and Channel Hang Time) Purpose

Cores utilizing perimeter sealing of core contents to prevent the core materials from migrating to contact babies' skin must have seals strong enough to withstand the swelling pressures of the core materials and the pressures exerted from baby. This method determines the strength of the seal by measuring how long the perimeter seal can withstand a constantly applied force.

[For Channel hang time only: The purpose of the printed channel specific Normalized Core Hang Time (=>Normalized Channel Core Hang Time=NChHT) is to determine the bond strength of the AGM free channels. The bond strength of printed AGM free channels in AFF (air felt free or cellulose free) laminates has an impact on diaper performance as a too weak bonding might result in inferior core integrity and less wet fit. This method determines the strength of the substrate to substrate bond by measuring how long the bonding is able to withstand a constantly applied force (static peel force).

Scope

Applicable for all diapers or absorbent cores having fully encapsulated cores with a core endflap (core front and back end seals). Diapers or cores may be air felt free. Core may have AGM free channels. Channel specific Normalized Core Hang Time (or Normalized channel hang time, NChHT) applicable for cores with AGM free channels showing the following parameters: minimum distance between channels at the measuring point of 10 mm and a minimum channel free distance at the measuring point of 20 mm to the core bag edge to ensure a proper clamping of the nonwoven into the clamps.

Equipment

Clips . . . Medium Binder Clips 25 mm Capacity #72050. ACCO World Product. Other suppliers: Yihai Products (#Y10003), Universal Office Products (#10210), Diamond (#977114), or equivalent Clips . . . Large Binder Clips 2 inch (50.8 mm). ACCO World Product. Other suppliers: Yihai Products, Universal Office Products, Diamond, or equivalent Test Stand . . . RT-10 room temperature (Shear Tester) w/timer. ChemInstruments, 510 Commercial Drive, Fairfield Ohio 45014-9797, USA; or equivalent. (See FIG. 1) Must be placed in a vibration free area Weight . . . Endseal: Normalized Core Hang Time (NCHT): 0.200 g (+/−1 g) TW200 Shear Tester Weight with hook on top (to attach to the clip). ChemInstruments, 510 Commercial Drive, Fairfield Ohio 45014-9797, USA; or equivalent;

Channel specific Normalized Core Hang Time (NChHT): 150 g (+/−1 g) TW150 Shear Tester Weight with hook on top (to attach to the clip). ChemInstruments, 510 Commercial Drive, Fairfield Ohio 45014-9797, USA; or equivalent Cutting Tools . . . Scissors and a 25.4 mm (1 inch) cutter (convenient source, (see FIG. 2), e.g. JDC Precision Sample Cutter made by Thwings-Albert Instrument Company Philadelphia USA, cat#99, cut width 25.4 mm, accuracy at least +/−0.1 mm)

Metal Ruler Traceable to NIST, DIN, JIS or other comparable National Standard, graduated in mm, longer than the length to be measured Marker Permanent Fine-tip waterproof marker with no more than 2 mm pen width from convenient source Sticks Optional: Sticks from a convenient source, min. length=sample with, stick weight <0.1 g Temperature Testo-temperature device (or equivalent) to measure temperature at sample height.

Measurement With an accuracy of ±0.5° C. and ±2.5% RH in the range between −10° C. and +50° C.

Device Testo GmbH & Co., Postbox 1140, D-79849 Lenzkirch (www.testo.com) Article number for Testo 625: 0563 6251.

Sample preparation: For normalized initial core end seal hang time and normalized initial channel hang time, test at room temperature about 2 hours after production. For normalized final core end seal hang time and normalized final channel hang time, test aged sample, meaning after 6 hours at 60° C.

1. Open the diaper topsheet side up and place it flat onto a table. For pull-ups open side seams and remove waistbands. Hold the diaper with one hand and carefully remove Ears, Leg Elastics and BLCs along the BLC continuous bond (outer edge) on both Operator Side (OS) and Drive Side (DS) (see FIG. 3).
2. Gently remove topsheet and acquisition system without damaging the core endflap gluing.

Back/Front edge bonding Specific Sample preparation:
1. If the Edge of the Core Encapsulation Material is Folded Under the Core, Unfold the endflap. If this is not possible without tearing any core materials, discard the sample and pull another sample.
2. The center of the core will be tested. Lay the pad onto the 25.4 mm cutter centered over the center of the core. Provide sufficient length on the cutter to ensure sufficient length (at least 65 mm) and cut the sample. Label the sample either "UTE"/Front or "TE"/Back with the marker
3. After cut is made by the 25.4 mm cutter, use the scissors to cut sample from the pad. Ensure that the sample measures 70 mm+/−5 mm. If the sample is too long, use scissors to cut off the necessary amount of material at the open end of the sample (area with core material). If the sample is too short, discard the sample and pull another sample.
4. Put each sample under the UV-light to identify the AGM edge and mark a line along the AGM edge at TE/Diaper Front and UTE/Diaper Back.
5. Gently open samples like a book up to the marked line and gently remove core material that is between Nonwoven Core Cover (NWCC) and Nonwoven Dusting Layer (NWDL).
6. Optional Step: Use marker to mark the edge of glued area. This should follow the shape of where the NWCC and NWDL are glued together. (line may not be straight).

Side Seal Specific Sample Preparation:
1. Inspect the core side seal glue at Drive Side (DS) and Operator Side (OS) for "open" areas, such as open channels, because of missing glue, with free access to the core materials (AGM)
   a) If no open areas are present proceed with step 2.
   b) In case of "open" areas skip further testing and report a Failure.
2. Label the cut samples appropriate, e.g. DS.
3. Lay the pad on the 25.4 mm cutter approximately in the middle of the crotch area. If you choose to cut and measure at a different position, note down where, e.g. OS-TE or DS-UTE.
4. Cut the pad in cross machine direction with the 25.4 mm cutter, use the scissors to cut sample in half
5. Optional: Measure the width of the sample at the gluing on the NWCC side. The width has to be 25±2 mm.
6. Put each sample under the UV-light to identify the AGM edge and mark a line along the AGM edge
7. Open samples like a book up to the marked inner line and gently remove core material that is between Nonwoven Core Cover and Nonwoven Dusting Layer.

Channel Specific Sample Preparation:
1. Label the cut samples appropriate, e.g. DS/OS (driveside/operator side, or left/right)
2. Put each sample under the UV-light to identify the beginning and the end of the channels in the front and in the back and mark a line in cross direction.
3. Define the center of the channel area by using a ruler and mark as the centerline.

4. Lay the pad on the 25.4 mm cutter and align to the centerline cutting the sample out of the TE area.
5. Cut the pad in cross direction and optionally measure the width of cut sample (target=25±2 mm).
6. Use the scissors to cut the sample that there are at least a 5 mm channel free flap at the inner side (cutting in machine direction) to get an OS and a DS sample. All samples will be tested/opened from the outside of the core.
7. Optional: Put each sample under the UV-light to identify the channel AGM edge and mark a line along the AGM edges of the channel.
8. Open samples from the outside of the core like a book up to the beginning of the printed channel (respectively the first marked line if you have marked it) and gently remove core material that is between Nonwoven Core Cover and Nonwoven Dusting Layer.

Test Procedure:

Set up the tester in an area where the temperature is constant and ensure that the tester has at least 2 h time to reach the temperature of the environment. The same applies to the samples which usually will have the same temperature as the environment and can then be measured right away. However if this is not the case one needs to wait at least 2 h to reach the temperature of the environment prior to the start of the measurement.

1. The equipment may be operated between 17.5° C.-28.5° C. for AFF products.
2. Roll the topsheet side part of the sample around a stick, which is not heavier than 0.2 g (AGM to the inside) and staple it for fixation. You may cut the stick with scissors if it is longer than the sample width. The stick ensures that the samples do not slip from the clamp.
3. Clamp the backsheet side/dusting layer side of the sample strip into the jaw of the large binder clip hanging at the top of the tester bar.
4. Clamp the other binder clip (medium) to the nonwoven core cover.
5. Once all test samples have been prepared, (can setup multiple tests at one time) begin picking up the weights from the tester switch (this will begin the timer) and slowly attach the 200 g weights for End flap or Side Seal or 150 g for AGM free channels to the lower binder clips and lower slowly until the weights hangs freely on the test strip.
6. As soon as the weight is released, push the timer reset button for that sample to begin the timer at 0 minutes. NOTE: The timer must be checked to ensure that it has begun counting from 0.0 min. The operator should look for the number to change from 0.0 min to 0.1 min.
7. Repeat procedure above for each sample prepared.
8. Measure and note down the temperature $T_a$ of the tester area at the sample height to the nearest 0.1° C. at the start of the measurement. The allowed temperature range is 17.5° C.-28.5° C. Measure the temperature at the beginning and at the end of the measurement. $T_a$ is the average temperature between the two.
9. The timers will stop automatically once the sample weight has fallen. This is the Hang time for that sample.

Calculation:

A) Temperature Adjustment to 23° C. (Normalization). Use the following calculation to adjust for temperatures $$t_{23°\ C.} = \left[ \left( \frac{311}{\exp\left(\frac{20207}{T_a + 273} - 62.527\right)} \right) \cdot t_a \right] \overbrace{}^{\text{Temperature correction factor}}$$

$t_{23°\ C.}$: Corrected hang time in [min] at T=23 [° C.]
$t_a$: actual hang time in [min] at the temperature $T_a$
$T_a$: temperature [° C.] of the test equipment and the sample during the measurement The result actual hang time and the actual temperature are input of $t_a$ and $T_a$ using the above equation $t_{23°\ C.}$.

Reporting:

Measure and write down the following values:
The actual temperature $T_a$ to the nearest 0.1° C.
The actual hang time $t_a$ to the nearest 0.1 min
The transformed hang time (t23) to the nearest 0.1 (normalized hang time).

Wet normalized initial channel hang time is calculated by the normalized initial channel hang time test method, except sample is first dipped in 200 ml 0.9% NaCl @ T=21° C. for 30 minutes and then tested.

2. Dynamic Mechanical Analysis (DMA) to Determine G' for Thermoplastic Compositions Temperature Sweep—Principle A dynamic mechanical analysis (DMA) is done. An oscillatory shear stress is continuously applied to the adhesive resulting in an oscillatory strain at constant amplitude, which is small enough to ensure fully recoverable deformation, whereas the temperature is increased (or decreased) in discrete steps. The relationship between the sinusoidal stress applied and the resulting strain response as well as the shift between both measures on the time axis are measured. The results are quantified by Storage Modulus [G'], Loss Modulus [G"] and Loss Factor [tan δ] of the adhesive in dependence of temperature.

Instrument:
TA Instruments DHR-3

Procedure:
1. Use a rheometer with 20 mm plate/plate geometry consisting of an upper steel plate (diameter: 20 mm) and a lower peltier or heating plate enabling temperature control. The rheometer needs to be capable of applying temperatures from 0° C. to 150° C.
2. Calibrate Rheometer according to instrument manual.
3. Cut off and weigh a piece of adhesive of 0.37 g+/−0.01 g and place it onto the centre of the Peltier or heating plate of the rheometer and set the temperature to 150° C.
4. After the adhesive is molten, slowly lower the upper plate to the geometry gap of 1000 micrometer. The velocity of the rheometer head must not exceed 1000 micrometer per second in order to achieve good contact between the adhesive and the upper plate without damaging the adhesive sample.
5. Cover the geometry with the geometry cover for 2 minutes so that the upper plate can heat up and the adhesive gets completely molten.
6. Remove the cover and rotate the upper plate manually to distribute the adhesive evenly between the upper plate and the Peltier or heating plate and to ensure full contact of the adhesive to the upper plate.
7. Afterwards cover the geometry with the geometry cover for another 2 minutes.

8. Remove the geometry cover and check whether the adhesive is distributed evenly.
9. Perform a pre-shearing at a shear rate of 2.5 seconds-1 for 1 minute to condition the adhesive.
10. After pre-shearing keep the temperature at 150° C. for 1 minute to let the adhesive settle and recover from pre-shearing.
11. Set Axial force control to 0.0 N with a sensitivity +/−0.1 N
12. Cool down to 25° C. and wait for 1 hour
13. Cool down to 10° C. and wait for 10 minutes
14. Start Temperature Sweep from 10 to 110° C. with temperature step of 2° C.
Equilibrate at each temperature step for 60 s.
Strain Amplitude: 0.03%
Angular frequency: 6.28319 rad/s Calculation/Reporting
From the temperature sweep report the following parameters:
Glass transition temperature in ° C.
(The glass transition temperature is defined at the peak maximum of the tan δ value
Cross-over temperature in ° C.
(The cross-over-temperature is found at the end of the rubber-plateau towards higher temperatures indicating the beginning of the terminal zone. At the cross-over-temperature storage- and loss modulus equal and tan δ value is 1)
Storage modulus at 21° C., 35° C., 60° C. and 90° C. in Pascal.

3. Wet Immobilization Test

Equipment
Graduated Cylinder
Stop watch (±0.1 sec)
Scissors
Light Box
Pen
Test solution: 0.90% saline solution at 23+/−2° C.
Metal ruler traceable to NIST, DIN, JIS or other comparable National Standard
PVC/metal dishes with a flat surface inside and a minimum length of the core bag length (n) to be measured and a maximum length n+30 mm, width of 105±5 mm, height of 30-80 mm or equivalent
Electronic Force Gauge (Range 0 to 50 Kg)
Wet Immobilization Impact Tester Equipment (WAIIT), Design package number: BM-00112.59500-R01 available from T.M.G. Technisches Buero Manfred Gruna Facilities:
Standard laboratory conditions, temperature: 23° C.±2° C., relative humidity: <55%

Sample Preparation
1. Open the product, topsheet side up.
2. Unfold the diaper and cut the cuff elastics approximately every 2.5 cm to avoid chassis tension.
3. For pull-up products open the side seams and remove the waistbands.
4. Lay the core bag flat and rectangular topsheet side up onto the light box surface without any folds.
5. Switch on the light box to clearly identify the absorbent core outer edges.
6. With a ruler, draw a line at the front and back absorbent core outer edges.
7. Measure the distance (A), between the two markers and divide the value by 2, this will be calculated distance (B).
8. Measure the calculated distance (B) from front marker towards the middle of the core bag and mark it. At this marker draw a line in the cross direction.

Test Procedure
WAIIT Calibration:
1. Make sure that the sliding board is in the lower position. Open the front door of the WAIIT tester and connect the force gauge hook to the upper sample clamp of the WAIIT. Make sure that the clamp is closed before connecting the spring-balance.
2. Use both hands on the spring-balance to lift continuously and as slowly as possible up the sliding board towards the upper position. Record the average value ($m_1$) during the execution to the nearest 0.02 kg.
3. Guide down the sliding board as slowly as possible to the lower position and record the average value ($m_2$) read off during execution to the nearest 0.02 kg.
4. Calculate and report the delta of $m_1$-$m_2$ to the nearest 0.01 kg. If the delta is 0.6 kg±0.3 kg continue measurement. Otherwise, an adjustment of the sliding board is necessary. Make sure that the sliding board is in lower position and check the sliding path for any contamination or damage. Check if the position of the sliding board to the sliding path is correctly adjusted by shaking the board. For easy gliding some clearance is needed. If not present, readjust the system.

WAIIT Test Settings:
Drop height is 50 cm.
Diaper load ($l_D$) is 73% of the core capacity (cc); $l_D$=0.73×cc.
Core capacity (cc) is calculated as: cc=$m_{SAP}$×$SAP_{GV}$, where $m_{SAP}$ is the mass of superabsorbent polymer (SAP) present in the diaper and $SAP_{GV}$ is the free swelling capacity of the superabsorbent polymer. Free swelling capacity of the superabsorbent polymer is determined with the method described in WO 2006/062258. The mass of the superabsorbent polymer present in the diaper is the average mass present in ten products.

Test Execution:
1. Reset the balance to zero (tare), put the dry core bag on the balance, weigh and report it to the nearest 0.1 g.
2. Measure the appropriate volume Saline (0.9% NaCl in deionized water) with the graduated cylinder.
3. Lay the core bag, topsheet side up, flat into the PVC dish. Pour the saline evenly over the core bag.
4. Take the PVC dish and hold it slanting in different directions, to allow any free liquid to be absorbed. Products with poly-backsheet need to be turned after a minimum waiting time of 2 minutes so that liquid under the backsheet can be absorbed. Wait for 10 minutes (+/−1 minute) to allow all saline to be absorbed. Some drops may retain in the PVC dish. Use only the defined PVC/metal dish to guarantee homogenous liquid distribution and less retained liquid.
5. Reset the balance to zero (tare), put the wet core bag on the balance. Weigh and report it to the nearest 0.1 g. Fold the core bag just once to make it fit on the balance. Check to see if the wet core bag weight is out of limit (defined as "dry core bag weight+diaper load±4 ml"). For example, 12 g dry core bag weight+150 ml load=162 g wet core bag weight. If the actual wet weight on the scale is between 158 g and 166 g, the pad can be used for shaking. Otherwise scrap the pad and use the next one.
6. Take the loaded core bag and cut the pad along the marked line in the cross direction.

7. Put the back of the wet core bag onto the balance ($m_1$). Weigh and report it to the nearest 0.1 g.
8. Take the wet core and clamp the end seal side in the top clamp of the sample holder of the WAIIT (open end of the core oriented down). Next, clamp both sides of the core with the side clamps of the sample holder making sure that the product is fixed to the sample holder along the whole product length. Make sure not to clamp the absorbent core, only the nonwoven; for some products this means securing the product with only the barrier leg cuff.
9. Lift up the sliding board to the upper position by using both hands until the board is engaged.
10. Close the safety front door and release the slide blade.
11. Reset the balance to zero (tare), take the tested core bag out of the WAIIT and put it on the balance ($m_2$). Report the weight to the nearest 0.1 g.
12. Repeat steps 7 to 11 with front of the wet core bag.

Reporting:
1. Record the dry core bag weight to the nearest 0.1 g.
2. Record the wet weight before ($m_{1\ front/back}$) and after ($m_{2\ front/back}$) testing, both to the nearest 0.1 g.
3. Calculate and report the average weight loss ($\Delta m$) to the nearest 0.1 g: $\Delta m = (m_{1front} + m_{1back}) - (m_{2front} + m_{2back})$
4. Calculate and report the weight loss in percent to the nearest 1%, ($\Delta m_{rel}$): $(\Delta m_{rel}) = (((m_{1front} + m_{1back}) - (m_{2front} + m_{2back})) \times 100)/(m_{1front} + m_{1back})$
5. Calculate and report Wet Immobilization (WI) as: $WI = 100\% - \Delta m_{rel}$ The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. An absorbent structure for an absorbent article, comprising a first substrate and an absorbent layer supported thereon; said absorbent layer comprising an absorbent material comprising a superabsorbent polymer material;
   wherein said absorbent structure comprises a fiberized net structure to at least partially immobilize said absorbent layer onto said first substrate;
   whereby said fiberized net structure has a storage modulus (G') at 21° C. of greater than about $1.2 \times 10^6$ Pa to $7.8 \times 10^6$.

2. The absorbent structure of claim 1, wherein said absorbent layer comprises at least two channels, said channels being substantially free of superabsorbent polymer material.

3. The absorbent structure of claim 1, wherein the structure is substantially cellulose-free.

4. The absorbent structure of claim 1, further comprising a hot melt adhesive.

5. The absorbent structure of claim 4, wherein the hot melt adhesive has a storage modulus (G') at 21° C. of greater than about $1.2 \times 10^6$ Pa to $7.8 \times 10^6$.

6. The absorbent structure of claim 4, wherein the fiberized net structure and/or the hot melt adhesive comprise a polyolefin.

7. The absorbent structure of claim 1, wherein the fiberized net structure is laid down onto the absorbent material such that the fiberized net structure is at least partially in contact with the absorbent material, the first substrate, and the absorbent layer.

8. The absorbent structure of claim 1, wherein the absorbent structure provides an absorbent material loss of no more than about 40%, according to the Wet Immobilization Test.

9. The absorbent structure of claim 1, wherein the fiberized net structure is a hot melt adhesive.

10. The absorbent structure of claim 1, wherein the first substrate is a nonwoven core cover.

11. The absorbent structure of claim 10, further comprising a second substrate.

12. The absorbent structure of claim 11, wherein the second substrate is at least partially bonded to the first substrate and wherein the second substrate is a nonwoven dusting layer.

13. The absorbent structure of claim 1, wherein an absorbent article comprises the absorbent structure.

14. The absorbent structure of claim 13, wherein the article further comprises a topsheet and a backsheet, and wherein the absorbent structure is disposed between the topsheet and the backsheet.

15. The absorbent structure of claim 1, wherein the fiberized net structure has a storage modulus (G') at 21° C. of greater than about $3.0 \times 10^6$ Pa to $7.8 \times 10^6$.

16. The absorbent structure of claim 1, wherein the fiberized net structure has a storage modulus (G') at 21° C. of greater than about $6.0 \times 10^6$ Pa to $7.8 \times 10^6$.

17. The absorbent structure of claim 1, wherein said fiberized net structure has a storage modulus (G') at 21° C. of from $3.63 \times 10^6$ to $7.8 \times 10^6$.

18. An absorbent structure for an absorbent article, comprising a first substrate and an absorbent layer supported thereon; said absorbent layer comprising an absorbent material comprising a superabsorbent polymer material;
   wherein said absorbent structure comprises an adhesive to at least partially immobilize said absorbent layer onto said first substrate;
   whereby said adhesive has a storage modulus (G') at 21° C. of greater than about $1.2 \times 10^6$ Pa to $7.8 \times 10^6$.

19. The absorbent structure of claim 18, wherein said absorbent layer comprises at least two channels, said channels being substantially free of superabsorbent polymer material.

20. The absorbent structure of claim 18, wherein the structure is substantially cellulose-free.

21. The absorbent structure of claim 18, further comprising a second adhesive.

22. The absorbent structure of claim 21, wherein the second adhesive has a storage modulus (G') at 21° C. of greater than about $1.2 \times 10^6$ Pa to $7.8 \times 10^6$.

23. The absorbent structure of claim 18, wherein the first substrate is a nonwoven core cover.

24. The absorbent structure of claim 23, further comprising a second substrate at least partially bonded to the first substrate, and wherein the second substrate is a nonwoven dusting layer.

25. The absorbent structure of claim 18, wherein an absorbent article comprises the absorbent structure, wherein the article further comprises a topsheet and a backsheet, and wherein the absorbent structure is disposed between the topsheet and the backsheet.

26. The absorbent structure of claim 18, wherein said adhesive has a storage modulus (G') at 21° C. of from $3.63 \times 10^6$ to $7.8 \times 10^6$.

\* \* \* \* \*